US006440730B1

(12) United States Patent
Von Laer et al.

(10) Patent No.: US 6,440,730 B1
(45) Date of Patent: Aug. 27, 2002

(54) RETROVIRAL HYBRID VECTORS PSEUDOTYPED WITH LCMV

(75) Inventors: Meike-Dorothee Von Laer, Hamburg (DE); Winfried Beyer, Hamburg (DE)

(73) Assignee: Heinrich-Pette-Institut, Hamburg (DE)

( * ) Notice: Subject to any disclaimer, the term of this patent is extended or adjusted under 35 U.S.C. 154(b) by 0 days.

(21) Appl. No.: 09/309,572

(22) Filed: May 11, 1999

(30) Foreign Application Priority Data

Nov. 26, 1998 (DE) .......................................... 198 56 463

(51) Int. Cl.$^7$ ............................. C12N 5/00; C12N 5/02; C12N 15/63; C12P 21/06; C12P 21/04
(52) U.S. Cl. .................... 435/325; 435/320.1; 435/455; 435/456; 435/69.1; 435/70.1
(58) Field of Search ...................... 424/93.21; 435/455, 435/320.1, 325, 366, 456, 69.1, 70.1

(56) References Cited

U.S. PATENT DOCUMENTS 5,591,624 A  *  1/1997  Barber et al. ............. 435/240.2

OTHER PUBLICATIONS

Dang et al. Clin. Cancer Res. 5:471–474, 1999.*
Gerson, S.L. Nature Med. 5:262–264, 1999.*
Wivel & Wilson. Hematol. Oncol. Clin. North Am. 12:483–501, 1998.*
Rudinger; Characteristics of the amino acids as components of a peptide hormone sequence, 1976, In Peptide Hormones (Parsons, J.A., ed), pp. 1–7.*
Ngo et al.; Computational Complexity, Protein Structure Prediction, and the Levinthal Paradox, 1994, In The Protein Folding Problem and Tertiary Structure Prediction (Merz et al., eds), pp. 491–494.*
Eck. et al.; Gene–Based Therapy, 1996, The Pharmacological Basis of Therapeutics: 77–101.*
Deonarian; Ligand–targeted receptor–mediated vectors for gene delivery, 1998, Exp. Opin. Ther. Patents 8(1): 53–69.*
Teng, M.N. et al: "A single amino acid change in the glycoprotein of lymphocytic choriomenengitis virus is associated with the ability to cause growth hormone deficiency syndrome", Journal of Virology, Bd. 70, Nr. 12, Dec. 1996, Seiten 8438–8443, XP002135672.
Villarete, L. et al: "Tissue–mediated selection of viral variants: Correlation between glycoprotein mutation and growth in neuronal cells", Journal of Virology, Bd. 68, Nr. 11, 1994, Seiten 7490–7496, XP002135673.
Miller, N. et al: "Targeted Vectors for Gene Therapy", FASEB Journal, US, Fed. of American Soc. for Experimental Biology, Bethesda, MD, Bd. 9, Nr. 2, Feb. 1, 1995, Seiten 190–199, XP000616414.
Blaese, R. Michael et al: "T Lymphocyte–Directed Gene Therapy for ADA SCID: Initial Trial Results after 4 Years", Science, vol. 270, Oct. 20, 1995, pp. 475–480.
Cavazana–Calvo, Marina et al: "Gene Therapy of Human Severe Combined Immunodeficiency (SCID)–X1 Disease", Science, vol. 288, Apr. 28, 2000, pp. 669–672.
Anderson, W. French, "The Best of Times, the Worst of Times", Science, vol. 288, Apr. 28, 2000, pp. 627–629.
Bonini, Chiara et al: "HSV–TK Gene Transfer into Donor Lymphocytes for Control of Allogeneic Graft–Versus–Leukemia", Science, vol. 276, Jun. 13, 1997, pp. 1719–1724.
Kohn, "T. lymphocytes with a normal ADA gene accumulate after transplantation of transduced autologous umbilical cord blood CD 34 $^+$ cells in ADA–deficient SCID neotates", Nature Medicine, vol. 4, No. 7, Jul. 1998, pp. 775–780.
Bruns, M. et al: "Lymphocytic choriomeningitis virus", Virology, Bd. 137, 1984, Seiten 49–57, XP000891881.
Miletic, H. et al: "Retroviral pseudotyped with lymphocytic choriomenengitis virus", Journal of Virology, Bd. 73, Nr. 7, Jul. 1999, Seiten 6114vectors –6116, XP002135674.
Miletic et al. "Infection of Hematopoietic Stem Cells with Pseudotyped Retroviral Vectors", Abstract, ASGT meeting, Seattle (May 28, 1998).

* cited by examiner

*Primary Examiner*—Dave T. Nguyen
*Assistant Examiner*—Quang Nguyen
(74) *Attorney, Agent, or Firm*—Nixon & Vanderhye P.C.

(57) ABSTRACT

The present invention relates in general to the pseudotyping of retroviruses with lymphocytic choriomeningitis virus. In particular, the invention relates to pseudotyping in MLV packaging cells which are optionally env-deleted, or in packaging cells derived from lentiviruses. Preferably, pseudotyping takes place by infection with LCMV or a preferably env-deleted mutant, or by transfection with an expression plasmid containing the gp gene of LCMV or a part thereof and optionally, in addition, the np, 1 and/or the z gene of LCMV. The invention also relates to the use of such pseudotypes for the infection of cells, particularly the use in gene therapy.

19 Claims, 7 Drawing Sheets

Ectopic expression of LCMV - GP

LCMV wild - type

EF1a - promoter alphavirus - vector

Figure 1:
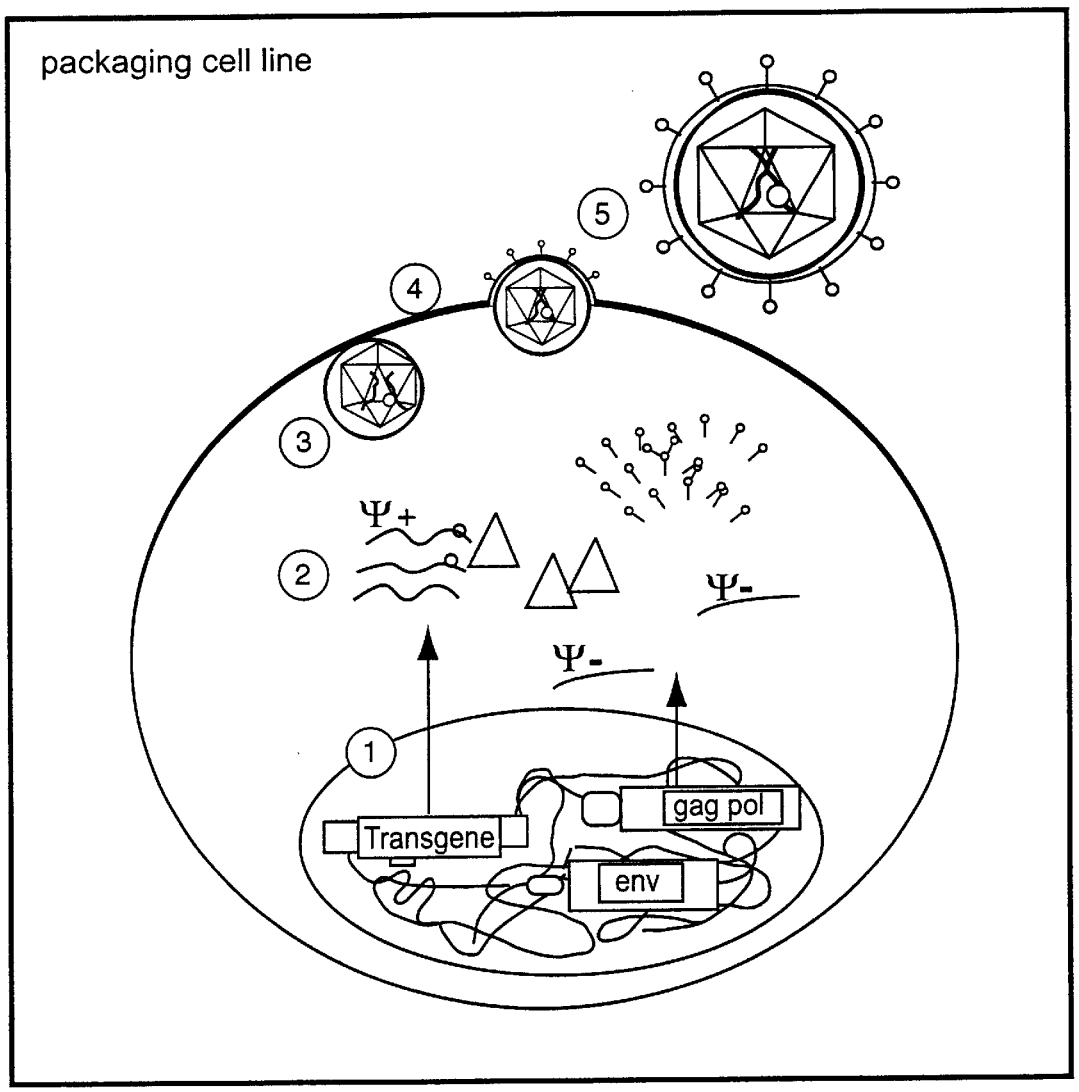
Figure 2:
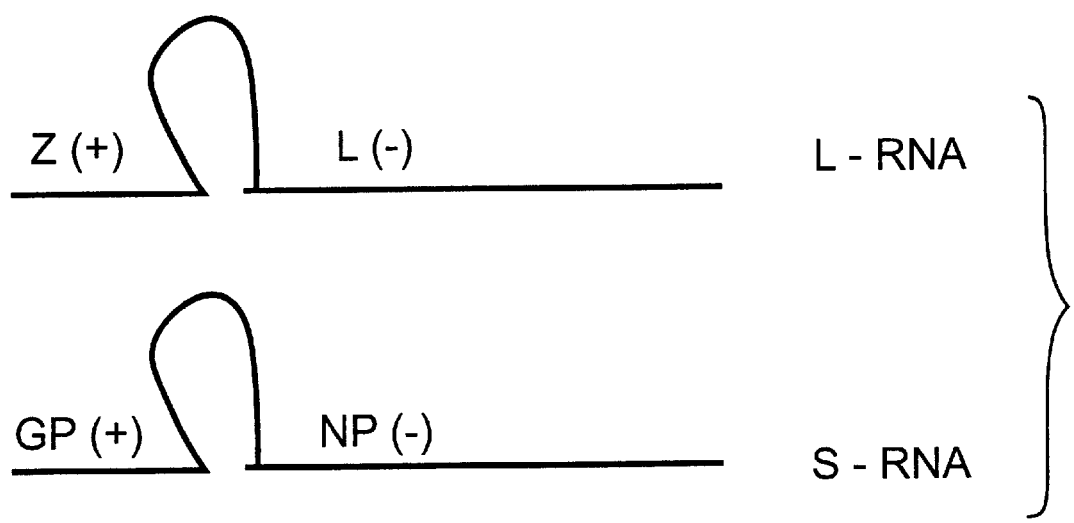
Figure 3:
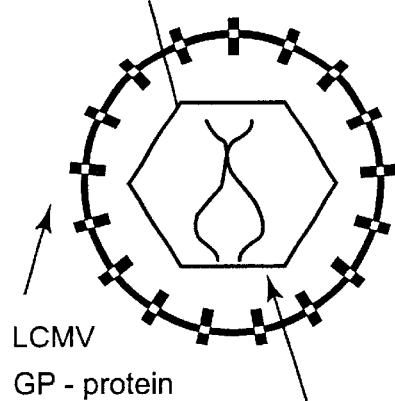
Figure 3:
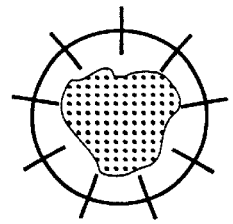
Figure 3:
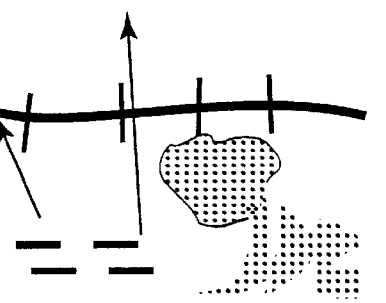

CMV - promoter + beta - globin Intron

Fig.4

SEQUENCE LISTING

<160> NUMBER OF SEQ ID NOS: 24

<210> SEQ ID NO 1
<211> LENGTH: 3375
<212> TYPE: DNA
<213> ORGANISM: Lymphocytic choriomeningitis virus

<400> SEQUENCE: 1

```
cgcaccgggg atcctaggct ttttggattg cgctttcctt taggacaact gggtgctgga      60
ttctatccag taaaaggatg ggtcagattg tgacaatgtt tgaggctttg cctcacatca     120
ttgatgaggt catcaacatt gtcattattg tgctcattat aatcacgagc atcaaagctg     180
tgtacaattt cgccacctgt gggatattag cactggtcag cttccttttt ctggctggta     240
ggtcctgtgg catgtacggc cttaatggtc ccgatatcta taagggggtt taccagttca     300
aatcagtgga gtttgatatg tctcacttaa atctgacgat gcccaatgcg tgctcagtca     360
acaactctca tcactacatc agtatgggaa gctctggact ggagccaact ttcaccaacg     420
actccatcct taatcacaac ttctgcaact taacctccgc tctcaacaaa aagtcttttg     480
accatacact catgagtata gtctcgagtc tacacctcag tatcagaggg aattccaact     540
acaaagcagt gtcttgtgat tttaacaatg gcatcaccat tcaatacaac ttgtcatctt     600
cggacccaca gagcgccatg agccagtgta ggactttcag aggtagagtc ttggacatgt     660
ttagaactgc ctttggagga aagtacatga aagtggctg gggctggaca ggttcagatg     720
gcaagaccac ttggtgcagc caaacaagct atcagtacct aatcatacaa acaggactt     780
gggaaaacca ctgtagatat gcaggccctt tgggatgtc tagaatcctc tttgctcagg     840
aaaagacaaa gtttctcact aggagacttt caggcacatt cacctggacc ctgtcagact     900
cctcaggagt agaaaatcca ggtggttatt gcctgaccaa atggatgatc cttgctgcag     960
agctcaaatg ttttgggaat acagctgttg caaaatgtaa tgtcaatcat gatgaagagt    1020
tctgtgacat gctacgacta attgattaca acaaggctgc cctgagtaag ttcaagcaag    1080
atgtagagtc tgccttgcat gtattcaaaa caacattaaa ttctctgatt tccgatcagc    1140
tgttgatgag gaatcatcta agagatctaa tggggtacc atactgtaat tactcaaagt    1200
tctggtatct ggaacatgct aagactggtg agactagtgt acccaagtgt tggcttgtca    1260
ctaatggctc ctacttgaat gagacccatt ttagtgatca aatcgaacaa gaagcagata    1320
acatgatcac agagatgttg aggaaggact acataaaag acaagggagt actccttag    1380
ccttaatgga tcttttgatg ttttcaacat cagcatactt gatcagcatc tttctgcatt    1440
ttgtgaggat accaacacat agacacataa agggcggttc atgtccaaag ccacatcgct    1500
tgaccaacaa ggggatctgt agttgtggtg cattcaaggt gcctggtgta aaactatct    1560
ggaaaagacg ctgatcagca gcgcctccct gactctccac ctcgaaagag gtggagagtc    1620
agggaggccc agcgggtctt agagtgtcac aacattgggt cctctgaaga tcaaatcatg    1680
tggcaggatg ttgtgaacgg tcttagatc agggagtctt gccttggaag cactctcaaa    1740
gatgatgcag tccatgagtg cacagtgtgg ggtgattct ttcttctttt tgtctctcac    1800
tacccagtg tgcatttgc atagccagcc atatttgtcc cacactttat cttcatattc    1860
```

-continued

```
tcttgaggcc tccttagtca tctcaacatc aatgagtttt atgtcccttc tattctgtga    1920
gtccagaagc tttctgatgt catcagaacc ttgacagctc aagaccatcc cttgtgggag    1980
agcacctata actgatgagg tcagcccagc ctgtgcattg aagaggtcag caagatccat    2040
gccgtgtgaa tacttggagt cctgcttgaa ttgcttctgg tccgtaggtt ctctgtaaaa    2100
atgtatgaat tgcccatttt gtggttgaaa tattgctatc tccactggat cattgaacct    2160
gccttcaatg tcaatccatg tgggagcatt gggatcaatc cctcccatca gtctttcaa     2220 cagcattgtt tgactgtaac tcaagcccac ctgaggtggg cctgctgctc caggcactgg    2280
cctagatgag ttggccacaa gttttcatt tgtgagatca attgtcgtgt ctcccatgc      2340 tctccccaca actgacgttc tacaggctat gtatggccat ccttcacctg aaagacagac    2400
tttataaagg atgttttcat aaggatttct atccccaact tgatctgaga caaacatgtt    2460
gagtttcttc ttggccccaa ggactgcttt taggagatcc tcactattgc ttggtttgat    2520
caaaatagat tccagcatgt tccctccatg tagcagagct gccccgctt tcacagccgc     2580 accaagactg aaattataac cagagatatt gatactagat tgctgttcag taatgacccc    2640
cagaactggg tgtttatctt ttagccttc taggtcactg agattcgggt atttgactgt     2700
gtaaagtaag ccaaggtctg tgagtgcctg cacaacatca ttgagtgggg tctgtgactg    2760
ttttgccatg caagccattg tcaggcttgg cattgtgccg aactgattgt tcagaagtga    2820
tgagtccttc acatcccaaa cccttactac accacttgca ccctgctgag gtcttctcat    2880
cccaaccatt tgcagtattt gggatctctg atcaagttgt tgtgctgtca aatttcccat    2940
gtagactcca gaagcttgag gcctctcagt tctcataatt ttggccttca gcttctcaag    3000
atcagctgca agggtcatca attcctctgc actaagtctt cccactttca gaacattttt    3060
ctttgatgta gacttcggat caacaagaga atgcacagtc tggttaagac tcctgagtct    3120
ctgcaagtct ttatcgtccc tcctttcctt tctcatgatc ctctgaacgt tgctgacttc    3180
agaaaagtcc aacccattta gaagactggt tgcgtccttg atgacggcag cctttacatc    3240
tgatgtaaaa ccctgcaact ccctcctcaa cgcctgtgtc cactgaaagc ttttgacttc    3300
tttggacaaa gacattttgt cacacaatga atttccaaat aaaagcgcaa tcaaatgcct    3360
aggatccact gtgcg                                                     3375
```

<210> SEQ ID NO 2
<211> LENGTH: 498
<212> TYPE: PRT
<213> ORGANISM: Lymphocytic choriomeningitis virus
<220> FEATURE:
<223> OTHER INFORMATION: S protein

<400> SEQUENCE: 2

```
Met Gly Gln Ile Val Thr Met Phe Glu Ala Leu Pro His Ile Ile Asp
  1               5                  10                  15

Glu Val Ile Asn Ile Val Ile Ile Val Leu Ile Ile Ile Thr Ser Ile
             20                  25                  30

Lys Ala Val Tyr Asn Phe Ala Thr Cys Gly Ile Leu Ala Leu Val Ser
         35                  40                  45

Phe Leu Phe Leu Ala Gly Arg Ser Cys Gly Met Tyr Gly Leu Asn Gly
     50                  55                  60

Pro Asp Ile Tyr Lys Gly Val Tyr Gln Phe Lys Ser Val Glu Phe Asp
 65                  70                  75                  80

Met Ser His Leu Asn Leu Thr Met Pro Asn Ala Cys Ser Val Asn Asn
                 85                  90                  95
```

```
Ser His His Tyr Ile Ser Met Gly Ser Ser Gly Leu Glu Pro Thr Phe
            100                 105                 110

Thr Asn Asp Ser Ile Leu Asn His Asn Phe Cys Asn Leu Thr Ser Ala
            115                 120             125

Leu Asn Lys Lys Ser Phe Asp His Thr Leu Met Ser Ile Val Ser Ser
        130             135             140

Leu His Leu Ser Ile Arg Gly Asn Ser Asn Tyr Lys Ala Val Ser Cys
145             150                 155                 160

Asp Phe Asn Asn Gly Ile Thr Ile Gln Tyr Asn Leu Ser Ser Ser Asp
                165             170             175

Pro Gln Ser Ala Met Ser Gln Cys Arg Thr Phe Arg Gly Arg Val Leu
            180             185             190

Asp Met Phe Arg Thr Ala Phe Gly Gly Lys Tyr Met Arg Ser Gly Trp
        195             200             205

Gly Trp Thr Gly Ser Asp Gly Lys Thr Thr Trp Cys Ser Gln Thr Ser
        210             215             220

Tyr Gln Tyr Leu Ile Ile Gln Asn Arg Thr Trp Glu Asn His Cys Arg
225             230             235             240

Tyr Ala Gly Pro Phe Gly Met Ser Arg Ile Leu Phe Ala Gln Glu Lys
            245             250             255

Thr Lys Phe Leu Thr Arg Arg Leu Ser Gly Thr Phe Thr Trp Thr Leu
            260             265             270

Ser Asp Ser Ser Gly Val Glu Asn Pro Gly Gly Tyr Cys Leu Thr Lys
            275             280             285

Trp Met Ile Leu Ala Ala Glu Leu Lys Cys Phe Gly Asn Thr Ala Val
        290             295             300

Ala Lys Cys Asn Val Asn His Asp Glu Glu Phe Cys Asp Met Leu Arg
305             310             315             320

Leu Ile Asp Tyr Asn Lys Ala Ala Leu Ser Lys Phe Lys Gln Asp Val
                325             330             335

Glu Ser Ala Leu His Val Phe Lys Thr Thr Leu Asn Ser Leu Ile Ser
            340             345             350

Asp Gln Leu Leu Met Arg Asn His Leu Arg Asp Leu Met Gly Val Pro
            355             360             365

Tyr Cys Asn Tyr Ser Lys Phe Trp Tyr Leu Glu His Ala Lys Thr Gly
        370             375             380

Glu Thr Ser Val Pro Lys Cys Trp Leu Val Thr Asn Gly Ser Tyr Leu
385             390             395             400

Asn Glu Thr His Phe Ser Asp Gln Ile Glu Gln Glu Ala Asp Asn Met
            405             410             415

Ile Thr Glu Met Leu Arg Lys Asp Tyr Ile Lys Arg Gln Gly Ser Thr
            420             425             430

Pro Leu Ala Leu Met Asp Leu Leu Met Phe Ser Thr Ser Ala Tyr Leu
            435             440             445

Ile Ser Ile Phe Leu His Phe Val Arg Ile Pro Thr His Arg His Ile
            450             455             460

Lys Gly Gly Ser Cys Pro Lys Pro His Arg Leu Thr Asn Lys Gly Ile
465             470             475             480

Cys Ser Cys Gly Ala Phe Lys Val Pro Gly Val Lys Thr Ile Trp Lys
            485             490             495

Arg Arg
```

<210> SEQ ID NO 3
<211> LENGTH: 3376
<212> TYPE: DNA
<213> ORGANISM: Lymphocytic choriomeningitis virus

<400> SEQUENCE: 3

| | | | | | |
|---|---|---|---|---|---|
| cgcaccgggg | atcctaggct | ttttggattg | cgctttcctc | tagatcaact | gggtgtcagg | 60 |
| ccctatccta | cagaaggatg | ggtcagattg | tgacaatgtt | tgaggctctg | cctcacatca | 120 |
| tcgatgaggt | gatcaacatt | gtcattattg | tgcttatcgt | gatcacgggt | atcaaggctg | 180 |
| tctacaattt | tgccacctgt | gggatattcg | cattgatcag | tttcctactt | ctggctggca | 240 |
| ggtcctgtgg | catgtacggt | cttaagggac | ccgacattta | caaggagtt | taccaattta | 300 |
| agtcagtgga | gtttgatatg | tcacatctga | acctgaccat | gcccaacgca | tgttcagcca | 360 |
| acaactccca | ccattacatc | agtatgggga | cttctggact | agaattgacc | ttcaccaatg | 420 |
| attccatcat | cagtcacaac | ttttgcaatc | tgacctctgc | cttcaacaaa | agacccttg | 480 |
| accacacact | catgagtata | gtttcgagcc | tacacctcag | tatcagaggg | aactccaact | 540 |
| ataaggcagt | atcctgcgac | ttcaacaatg | gcataaccat | ccaatacaac | ttgacattct | 600 |
| cagatcgaca | aagtgctcag | agccagtgta | gaaccttcag | aggtagagtc | ctagatatgt | 660 |
| ttagaactgc | cttcgggggg | aaatacatga | ggagtggctg | gggctggaca | ggctcagatg | 720 |
| gcaagaccac | ctggtgtagc | cagacgagtt | accaataccct | gattatacaa | aatagaacct | 780 |
| gggaaaacca | ctgcacatat | gcaggtcctt | ttgggatgtc | caggattctc | ctttcccaag | 840 |
| agaagactaa | gttcttcact | aggagactag | cgggcacatt | cacctggact | tgtcagact | 900 |
| cttcaggggt | ggagaatcca | ggtggttatt | gcctgaccaa | atggatgatt | cttgctgcag | 960 |
| agcttaagtg | tttcgggaac | acagcagttg | cgaaatgcaa | tgtaaatcat | gatgccgaat | 1020 |
| tctgtgacat | gctgcgacta | attgactaca | acaaggctgc | tttgagtaag | ttcaaagagg | 1080 |
| acgtagaatc | tgccttgcac | ttattcaaaa | caacagtgaa | ttctttgatt | tcagatcaac | 1140 |
| tactgatgag | gaaccacttg | agagatctga | tgggggtgcc | atattgcaat | tactcaaagt | 1200 |
| tttggtacct | agaacatgca | aagaccggcg | aaactagtgt | ccccaagtgc | tggcttgtca | 1260 |
| ccaatggttc | ttacttaaat | gagacccact | tcagtgatca | aatcgaacag | gaagccgata | 1320 |
| acatgattac | agagatgttg | aggaaggatt | acataaagag | gcagggagt | accccctag | 1380 |
| cattgatgga | ccttctgatg | ttttccacat | ctgcatatct | agtcagcatc | ttcctgcacc | 1440 |
| ttgtcaaaat | accaacacac | aggcacataa | aggtggctc | atgtccaaag | ccacaccgat | 1500 |
| taaccaacaa | aggaatttgt | agttgtggtg | catttaaggt | gcctggtgta | aaaccgtct | 1560 |
| ggaaaagacg | ctgaagaaca | gcgcctccct | gactctccac | ctcgaaagag | gtggagagtc | 1620 |
| agggaggccc | agagggtctt | agagtgtcac | aacatttggg | cctctaaaaa | ttaggtcatg | 1680 |
| tggcagaatg | ttgtgaacag | ttttcagatc | tgggagcctt | gctttggagg | cgctttcaaa | 1740 |
| aatgatgcag | tccatgagtg | cacagtgcgg | ggtgatctct | ttcttctttt | tgtcccttac | 1800 |
| tattccagta | tgcatcttac | acaaccagcc | atatttgtcc | cacactttgt | cttcatactc | 1860 |
| cctcgaagct | tccctggtca | tttcaacatc | gataagctta | atgtccttcc | tattctgtga | 1920 |
| gtccagaagc | tttctgatgt | catcggagcc | ttgacagctt | agaaccatcc | cctgcggaag | 1980 |
| agcacctata | actgacgagg | tcaacccggg | ttgcgcattg | aagaggtcgg | caagatccat | 2040 |
| gccgtgtgag | tacttggaat | cttgcttgaa | ttgttttga | tcaacgggtt | ccctgtaaaa | 2100 |
| gtgtatgaac | tgcccgttct | gtggttggaa | aattgctatt | tccactggat | cattaaatct | 2160 |

-continued

| | |
|---|---|
| accctcaatg tcaatccatg taggagcgtt ggggtcaatt cctcccatga ggtctttaa | 2220 |
| aagcattgtc tggctgtagc ttaagcccac ctgaggtgga cctgctgctc caggcgctgg | 2280 |
| cctgggtgaa ttgactgcag gtttctcgct tgtgagatca attgttgtgt tttcccatgc | 2340 |
| tctccccaca atcgatgttc tacaagctat gtatggccat ccttcacctg aaaggcaaac | 2400 |
| tttatagagg atgttttcat aagggttcct gtccccaact tggtctgaaa caaacatgtt | 2460 |
| gagttttctc ttggccccga gaactgcctt caagaggtcc tcgctgttgc ttggcttgat | 2520 |
| caaaattgac tctaacatgt taccccatc aacagggct gccctgcct tcacggcagc | 2580 |
| accaagacta aagttatagc cagaaatgtt gatgctggac tgctgttcag tgatgacccc | 2640 |
| cagaactggg tgcttgtctt tcagccttc aagatcatta agatttggat acttgactgt | 2700 |
| gtaaagcaag ccaaggtctg tgagcgcttg tacaacgtca ttgagcggag tctgtgactg | 2760 |
| tttggccata caagccatag ttagacttgg cattgtgcca aattgattgt tcaaaagtga | 2820 |
| tgagtctttc acatcccaaa ctcttaccac accacttgca ccctgctgag gctttctcat | 2880 |
| cccaactatc tgtaggatct gagatctttg gtctagttgc tgtgttgtta agttccccat | 2940 |
| atatacccct gaagcctggg gcctttcaga cctcatgatc ttggccttca gcttctcaag | 3000 |
| gtcagccgca agagacatca gttcttctgc actgagcctc cccactttca aaacattctt | 3060 |
| ctttgatgtt gactttaaat ccacaagaga atgtacagtc tggttgagac ttctgagtct | 3120 |
| ctgtaggtct tgtcatctc tcttttcctt cctcatgatc ctctgaacat tgctgacctc | 3180 |
| agagaagtcc aacccattca gaaggttggt tgcatcctta atgacagcag ccttcacatc | 3240 |
| tgatgtgaag ctctgcaatt ctcttctcaa tgcttgcgtc cattggaagc tcttaacttc | 3300 |
| cttagacaag gacatcttgt tgctcaatgg tttctcaaga caaatgcgca atcaaatgcc | 3360 |
| taggatccac tgtgcg | 3376 |

<210> SEQ ID NO 4
<211> LENGTH: 498
<212> TYPE: PRT
<213> ORGANISM: Lymphocytic choriomeningitis virus
<220> FEATURE:
<223> OTHER INFORMATION: envelope glycoprotein

<400> SEQUENCE: 4

Met Gly Gln Ile Val Thr Met Phe Glu Ala Leu Pro His Ile Ile Asp
 1               5                  10                  15

Glu Val Ile Asn Ile Val Ile Val Leu Ile Val Ile Thr Gly Ile
            20                  25                  30

Lys Ala Val Tyr Asn Phe Ala Thr Cys Gly Ile Phe Ala Leu Ile Ser
        35                  40                  45

Phe Leu Leu Leu Ala Gly Arg Ser Cys Gly Met Tyr Gly Leu Lys Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Thr Ser Gly Leu Glu Leu Thr Phe
            100                 105                 110

Thr Asn Asp Ser Ile Ile Ser His Asn Phe Cys Asn Leu Thr Ser Ala
        115                 120                 125

Phe Asn Lys Lys Thr Phe Asp His Thr Leu Met Ser Ile Val Ser Ser
    130                 135                 140

```
Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
            165                 170                 175

Arg Gln Ser Ala Gln Ser Gln Cys Arg Thr Phe Arg Gly Arg Val Leu
        180                 185                 190

Asp Met Phe Arg Thr Ala Phe Gly Gly Lys Tyr Met Arg Ser Gly Trp
    195                 200                 205

Gly Trp Thr Gly Ser Asp Gly Lys Thr Thr Trp Cys Ser Gln Thr Ser
210                 215                 220

Tyr Gln Tyr Leu Ile Ile Gln Asn Arg Thr Trp Glu Asn His Cys Thr
225                 230                 235                 240

Tyr Ala Gly Pro Phe Gly Met Ser Arg Ile Leu Leu Ser Gln Glu Lys
                245                 250                 255

Thr Lys Phe Phe Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Ala Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Val Ser Ile Phe Leu His Leu Val Lys Ile Pro Thr His Arg His Ile
450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Val Trp Lys
                485                 490                 495

Arg Arg

<210> SEQ ID NO 5
<211> LENGTH: 558
<212> TYPE: PRT
<213> ORGANISM: Lymphocytic choriomeningitis virus
<220> FEATURE:
<223> OTHER INFORMATION: nucleoprotein

<400> SEQUENCE: 5

Met Ser Leu Ser Lys Glu Val Lys Ser Phe Gln Trp Thr Gln Ala Leu
```

-continued

```
  1               5                   10                  15
Arg Arg Glu Leu Gln Ser Phe Thr Ser Asp Val Lys Ala Ala Val Ile
              20                  25              30

Lys Asp Ala Thr Asn Leu Leu Asn Gly Leu Asp Phe Ser Glu Val Ser
          35                  40              45

Asn Val Gln Arg Ile Met Arg Lys Glu Lys Arg Asp Asp Lys Asp Leu
      50                  55              60

Gln Arg Leu Arg Ser Leu Asn Gln Thr Val His Ser Leu Val Asp Leu
65                  70              75                      80

Lys Ser Thr Ser Lys Lys Asn Val Leu Lys Val Gly Arg Leu Ser Ala
              85                  90              95

Glu Glu Leu Met Ser Leu Ala Ala Asp Leu Glu Lys Leu Lys Ala Lys
              100                 105             110

Ile Met Arg Ser Glu Arg Pro Gln Ala Ser Gly Val Tyr Met Gly Asn
              115                 120             125

Leu Thr Thr Gln Gln Leu Asp Gln Arg Ser Gln Ile Leu Gln Ile Val
      130                 135             140

Gly Met Arg Lys Pro Gln Gln Gly Ala Ser Gly Val Val Arg Val Trp
145                 150             155                     160

Asp Val Lys Asp Ser Ser Leu Leu Asn Asn Gln Phe Gly Thr Met Pro
              165                 170             175

Ser Leu Thr Met Ala Cys Met Ala Lys Gln Ser Gln Thr Pro Leu Asn
              180                 185             190

Asp Val Val Gln Ala Leu Thr Asp Leu Gly Leu Leu Tyr Thr Val Lys
          195                 200             205

Tyr Pro Asn Leu Asn Asp Leu Glu Arg Leu Lys Asp Lys His Pro Val
      210                 215             220

Leu Gly Val Ile Thr Glu Gln Gln Ser Ser Ile Asn Ile Ser Gly Tyr
225                 230             235                     240

Asn Phe Ser Leu Gly Ala Ala Val Lys Ala Gly Ala Ala Leu Leu Asp
              245                 250             255

Gly Gly Asn Met Leu Glu Ser Ile Leu Ile Lys Pro Ser Asn Ser Glu
              260                 265             270

Asp Leu Leu Lys Ala Val Leu Gly Ala Lys Arg Lys Leu Asn Met Phe
          275                 280             285

Val Ser Asp Gln Val Gly Asp Arg Asn Pro Tyr Glu Asn Ile Leu Tyr
      290                 295             300

Lys Val Cys Leu Ser Gly Glu Gly Trp Pro Tyr Ile Ala Cys Arg Thr
305                 310             315                     320

Ser Ile Val Gly Arg Ala Trp Glu Asn Thr Thr Ile Asp Leu Thr Ser
              325                 330             335

Glu Lys Pro Ala Val Asn Ser Pro Arg Pro Ala Pro Gly Ala Ala Gly
              340                 345             350

Pro Pro Gln Val Gly Leu Ser Tyr Ser Gln Thr Met Leu Leu Lys Asp
      355                 360             365

Leu Met Gly Gly Ile Asp Pro Asn Ala Pro Thr Trp Ile Asp Ile Glu
      370                 375             380

Gly Arg Phe Asn Asp Pro Val Glu Ile Ala Ile Phe Gln Pro Gln Asn
385                 390             395                     400

Gly Gln Phe Ile His Phe Tyr Arg Glu Pro Val Asp Gln Lys Gln Phe
              405                 410             415

Lys Gln Asp Ser Lys Tyr Ser His Gly Met Asp Leu Ala Asp Leu Phe
              420                 425             430
```

Asn Ala Gln Pro Gly Leu Thr Ser Ser Val Ile Gly Ala Leu Pro Gln
            435                 440                 445

Gly Met Val Leu Ser Cys Gln Gly Ser Asp Asp Ile Arg Lys Leu Leu
        450                 455                 460

Asp Ser Gln Asn Arg Lys Asp Ile Lys Leu Ile Asp Val Glu Met Thr
465                 470                 475                 480

Arg Glu Ala Ser Arg Glu Tyr Glu Asp Lys Val Trp Asp Lys Tyr Gly
                485                 490                 495

Trp Leu Cys Lys Met His Thr Gly Ile Val Arg Asp Lys Lys Lys Lys
            500                 505                 510

Glu Ile Thr Pro His Cys Ala Leu Met Asp Cys Ile Ile Phe Glu Ser
            515                 520                 525

Ala Ser Lys Ala Arg Leu Pro Asp Leu Lys Thr Val His Asn Ile Leu
        530                 535                 540

Pro His Asp Leu Ile Phe Arg Gly Pro Asn Val Val Thr Leu
545                 550                 555

<210> SEQ ID NO 6
<211> LENGTH: 6680
<212> TYPE: DNA
<213> ORGANISM: Lymphocytic choriomeningitis virus

<400> SEQUENCE: 6
cgcaccgagg atcctaggct ttttgatgcg caatggatga atcatctca gaattgagag      60
agttatgttt aaactatata gaacaggatg agaggttgtc aaggcagaaa ctcaactttc    120
tgggacaaag gaacccaga atggttctga ttgaggact caagttgctg tcacgctgca    180
ttgaaataga cagtgcagac aagagtggct gcacacacaa ccacgacgat aagtctgtgg    240
aaacaatttt ggtggagtct ggaattgtat gcccaggact accacttatc attcctgatg    300
gttacaagct gatagacaat tctctcattc ttcttgagtg ttttgttagg agctcaccag    360
ccagttttga agaaaattt atagaggaca ctaacaaatt ggcatgcatc agggaagacc    420
ttgctgttgc gggtgtcaca ttagttccaa tagtagatgg tcgttgtgat tatgataata    480
gttttatgcc agagtgggca aacttcaaat ttagagacct tttattcaaa cttttggagt    540
attctaacca aaatgagaaa gtctttgaag agtctgaata ttttagactc tgtgagtccc    600
tgaagactac tatcgacaag cgctccggta tggactctat gaaaattctg aaagatgcga    660
ggtcaactca caatgatgaa attatgagga gtgtgccacga aggcatcaac cccaacatga    720
gctgtgatga tgtggttttt ggaataaact ctcttttcag caggtttaga agagatttag    780
aaagtgggaa attaaagaga aactttcaga agtaaaccc tgaaggcttg atcaaggaat    840
tctctgagct ctatgaaaac cttgctgata gtgatgatat cttaacatta agcagggagg    900
cagtcgaatc ctgtcctttg atgagattca taactgcaga gacccatggg cacgaaaggg    960
gaagtgagac tagcactgaa tatgagaggc tcctctctat gttaaacaaa gtcaagagtt   1020
tgaaactgtt gaatactaga aggagacagt tgttaaatct ggatgttttg tgtctttcct   1080
cattgataaa acagtcgaaa ttcaagggt taaaaatga taaacactgg gtgggttgtt   1140
gctatagtag tgtgaatgat aggctggtaa gctttcacag cactaaagag gagttcatta   1200
gacttttgag gaatagaaaa aagtcaaagg tgtttagaaa ggtgtctttt gaggaattgt   1260
ttagggcgtc tattagtgag ttcattgcaa aaattcaaaa atgcctgtta gtggtgggac   1320
tgagtttcga gcattacgga ctgtctgaac accttgagca agaatgccac ataccattca   1380

```
ctgaatttga gaactttatg aaaattggag ctcacccgat aatgtattat acgaagtttg    1440
aagattacaa tttccaaccc agcacagagc agctgaagaa catacagagc ctgagaagat    1500
tatcatctgt tgtctggcc ttaacaaaca gtatgaaaac tagctcagtt gctagactaa    1560
ggcaaaatca aatagggtct gtgagatatc aagtggtaga atgcaaagaa gtgttttgcc    1620
aagtaataaa actggactct gaagaatacc acctattata ccagaagact ggagaatctt    1680
caaggtgcta ctccatacaa ggcccggatg gtcatttaat ttccttctat gcagatccta    1740
aaaggttctt tttaccaatt tttcagatg aggtcttata caatatgata gacatcatga    1800
tttcatggat tagatcatgt cctgatttga aagactgtct caccgacatt gaggttgcac    1860
tgaggaccct attgttgcta atgctcacca acccaacaaa gagaaatcaa aagcaggtac    1920
agagtgtcag atatttggtg atggcaatag tgtcagattt ttcatctaca tcattaatgg    1980
ataagttgag ggaggatctg atcacacctg ctgagaaggt ggtgtataag ctgcttagat    2040
tcctaataaa aactattttt ggtactggtg agaaggtgtt gttgagtgca aaatttaaat    2100
ttatgttgaa tgtgtcatac ctgtgtcatt tgatcacaaa ggagacccct gacaggctaa    2160
cagatcagat aaaatgtttt gaaaagttct ttgagcccaa aagtcaattt ggttttttg    2220 tcaaccccaa ggaagcaatc actcctgagg aagaatgtgt gttctatgag caaatgaaga    2280
gattcactag taaagaaatt gactgtcagc atacaactcc agtgttaat ctggaagcct    2340 ttagcctaat ggtgtcttca tttaacaacg gcactttaat tttcaaagga gagaagaagc    2400
taaacagcct agatcccatg actaactctg atgtgcgac agcattagat cttgctagta    2460
acaaaagtgt ggtggttaat aagcatctaa atggagaacg acttctggaa tatgacttta    2520
acaaattgct tgttagtgct gtgagtcaaa ttacggagag tttcgtaaga aaacaaaagt    2580
ataagttgag ccactcagac tatgaatata agtttccaa gttagtctct agattggtca    2640
tcggttccaa gggagaagag acaggagat cggaagacaa cctggcagaa atatgttttg    2700
atggagaaga agagacaagc ttcttcaaaa gtctcgaaga aaaggtcaac accacaatag    2760
cacggtacag aagaggtagg agggccaatg acaaaggaga tggagaaaaa cttacaaata    2820
caaaaggact acatcatttta cagcttattc taacagggaa gatggctcac ttaagaaaag    2880
ttatcttgtc agaaatatct ttccatttag tagaagactt tgacccatca tgtctaacca    2940
atgatgacat gaaatttatc tgtgaggctg ttgagggttc cacagagctg tcacctttgt    3000
atttcacctc agtcattaaa gatcagtgtg gcctcgatga gatggcaaaa aaccttttgta    3060 gaaagttctt ttctgagaat gattggtttt cttgcatgaa gatgattctg ttgcaaatga    3120
atgcaaatgc gtactcaggg aaatacaggc atatgcaaag gcaaggcttg aatttcaaat    3180
ttgactggga caaactggaa gaagacgtga gaatcagtga gagggaaagt aattctgagt    3240
cccttagtaa agctctgtcg ttgacaaaat gtatgagtgc tgctttgaaa atctgtgct    3300 tctactcaga agaatcacca acatcataca cctcagtagg tcctgactct ggaaggctga    3360
aatttgcact atcttataaa gagcaggttg ggggaaatag agaactctat attggagatt    3420
tgaggacaaa aatgttcaca aggttaatag aagattattt tgagtctttt tcaagtttct    3480
tttcaggctc ctgtttaaac aatgataagg aatttgaaaa tgcaatcttg tcaatgacta    3540
tcaatgtgcg ggaagggttc ttaaactata gtatggatca cagcaaatgg ggaccaatga    3600
tgtgcccatt tttgttctta atgtttctac aaaatctcaa actaggtgat gaccagtatg    3660
tgcgttccgg gaaagatcat gttagcactt tgttaacttg gcacatgcat aagcttgtcg    3720 aggtccccttt tcctgttgtg aatgcaatga tgaaatcata tgtcaagtcg aagctaaaac    3780
```

```
ttctcagggg ttcagaaaca actgttactg agagaattt cagacaatat tttgaaatgg      3840
ggatagtgcc atcccatata tccagcctta ttgatatggg gcagggaatc ttgcataatg      3900
cttctgactt ctatggtttg cttagcgaga ggttcatcaa ctactgcatt ggtgttatct      3960
ttggcgaaag accagaggct tacacatcaa gtgatgatca gatcactta tttgatagga      4020 ggctgagtga cctggttgta agtgatccgg aggaagtcct tgtcctgttg gaattccaat      4080
ctcatctgag cggcttgtta aacaaattta tcagcccaaa agtgtggct gggaggttcg      4140 ctgcagaatt taaatctaga ttctatgtat gggggagga gtccctctt ctcacaaagt      4200 ttgtatctgc agcgctacac aatgtcaagt gtaagagcc acatcaactt tgtgaaacaa      4260
tagatacaat tgcagatcaa gccatcgcaa atggcgtccc agtctcccta gttaatagta      4320
tccaaaggag aacactggac tcctaaagt atgccaattt ccctttggat ccatttctac      4380
tgaataccaa cactgatgtg aaagattggc tggatggttc tagaggttac agaatacaaa      4440
gactcattga ggaactgtgt cctaatgaaa caaaggttgt aagaaagctt gtaaggaaac      4500
tgcatcataa gctcaaaaat ggtgaattta atgaagaatt ttcttagac ctatttaaca      4560 gagataaaac ggaggccatt cttcaattgg gagacctcct cggtcttgaa gaagatctga      4620
atcagttagc agatgttaac tggttgaatt tgaatgaaat gttcccatta aggatggttt      4680
taagacaaaa ggtggttat ccatcagtga tgactttcca agaggaaaga atcccatcat      4740
tgatcaagac actccagaac aactttgta gtaaattcac aaggggtgca cagaagctgc      4800
tgtcagaagc aatcaacaag tcagctttcc agagttgtat ctcatctggc tttataggcc      4860
tttgcaaaac tctaggaagc aggtgtgtga gaaacaaaaa tagggaaaat ctgtatatca      4920
aaaagctgct tgaggatcta accacagatg atcatgtgac aagagtttgc aatcgggatg      4980
gtataacgct gtacatttgt gacaaacagt ctcatccaga agcccaccgt gatcatatat      5040 gcctttaag gcctcttctt tgggactaca tttgtatttc attgagcaac tcttttgagt      5100
tgggtgtttg ggtcctagca gaaccgacca agggaaggaa taacagtgag aacctaactc      5160
ttaagcactt aaacccatgt gattatgtag caagaaagcc tgagagctca aggctactgg      5220
aggacaaagt gaatttgaac caagtgattc aatctgtgag gcggctatat cccaagatct      5280
ttgaggatca gcttcttcca tttatgtctg acatgagctc aaaaaacatg aggtggagtc      5340
ccagaattaa attccttgac ctctgtgttt taattgatat taactcagaa tccttgtcac      5400
tcatttctca tgttgttaag tggaaaaggg atgaacatta cactgttctg ttttctgacc      5460
ttgccaattc tcatcagcga tctgactcca gtcggttga tgaatttgtt gttagcacga      5520
gggatgtctg caagaacttc ttaaaacagg tgtattttga atcatttgtt cgagaatttg      5580
ttgcaacaac caggacatta ggcaattttt catggttccc tcataaagaa atgatgccat      5640
ctgaagatgg tgctgaggca ctgggcccct ttcaatcatt tgtctcaaag gtggtgaaca      5700
aaaatgtgga gaggcctatg tttaggaatg atttgcagtt tggttttggg tggttctctt      5760
accgaatggg agatgttgtg tgtaatgctg ccatgttgat taggcagggc ctgacaaacc      5820
caaaggcatt taaatcctta aggatctgt gggactacat gctcaactac acaaaagggg      5880
tattggagtt ttcaatttca gtggactta cgcacaatca gaataatact gactgtttaa      5940
ggaaattttc attgatattc ttggttaggt gccaattaca gaatccaggt gtggctgaac      6000
ttttatcatg ctctcacctc tttaagggtg agatagatag aagaatgttg gatgaatgcc      6060
tccacttact gaggacagac tctgtcttca aggtgaacga tggtgtcttt gatatcagat      6120
```

-continued

```
ctgaagagtt tgaggattac atggaagatc ccttgatact tggtgattct cttgagcttg   6180
agttgttggg ctccaaaaga atactggatg ggattagatc tattgacttt gagagagttg   6240
gacctgagtg ggagcctgtg ccactgactg taaagatggg tgcccttttt gaaggaagaa   6300
accttgtcca aaatatcatt gtgaagctgg agaccaagga catgaaagtc tttctagcag   6360
gacttgaggg ctatgaaaag attagtgatg tccttgggaa cctcttcctg catcgattca   6420
gaactggtga acatttgttg ggttcagaga taagtgtaat cctccaggaa ctatgtatag   6480
acagatctat tctgctgatt ccactgtcgc ttttgccaga ctggttcgcc tttaaggatt   6540
gcagactttg ttttagcaaa tctaggagca ctttgatgta tgaaatagtg gggggcaggt   6600
ttagactcaa ggggaggtcc tgcgacgatt ggctaggcgg gtcggtggcc gaggacatcg   6660
actgatgggc atctcctggg                                               6680
```

<210> SEQ ID NO 7
<211> LENGTH: 2210
<212> TYPE: PRT
<213> ORGANISM: Lymphocytic choriomeningitis virus
<220> FEATURE:
<223> OTHER INFORMATION: L protein

<400> SEQUENCE: 7

```
Met Asp Glu Ile Ile Ser Glu Leu Arg Glu Leu Cys Leu Asn Tyr Ile
  1               5                  10                  15

Glu Gln Asp Glu Arg Leu Ser Arg Gln Lys Leu Asn Phe Leu Gly Gln
             20                  25                  30

Arg Glu Pro Arg Met Val Leu Ile Glu Gly Leu Lys Leu Leu Ser Arg
         35                  40                  45

Cys Ile Glu Ile Asp Ser Ala Asp Lys Ser Gly Cys Thr His Asn His
     50                  55                  60

Asp Asp Lys Ser Val Glu Thr Ile Leu Val Glu Ser Gly Ile Val Cys
 65                  70                  75                  80

Pro Gly Leu Pro Leu Ile Ile Pro Asp Gly Tyr Lys Leu Ile Asp Asn
                 85                  90                  95

Ser Leu Ile Leu Leu Glu Cys Phe Val Arg Ser Ser Pro Ala Ser Phe
            100                 105                 110

Glu Lys Lys Phe Ile Glu Asp Thr Asn Lys Leu Ala Cys Ile Arg Glu
        115                 120                 125

Asp Leu Ala Val Ala Gly Val Thr Leu Val Pro Ile Val Asp Gly Arg
    130                 135                 140

Cys Asp Tyr Asp Asn Ser Phe Met Pro Glu Trp Ala Asn Phe Lys Phe
145                 150                 155                 160

Arg Asp Leu Leu Phe Lys Leu Leu Glu Tyr Ser Asn Gln Asn Glu Lys
                165                 170                 175

Val Phe Glu Glu Ser Glu Tyr Phe Arg Leu Cys Glu Ser Leu Lys Thr
            180                 185                 190

Thr Ile Asp Lys Arg Ser Gly Met Asp Ser Met Lys Ile Leu Lys Asp
        195                 200                 205

Ala Arg Ser Thr His Asn Asp Glu Ile Met Arg Met Cys His Glu Gly
    210                 215                 220

Ile Asn Pro Asn Met Ser Cys Asp Asp Val Val Phe Gly Ile Asn Ser
225                 230                 235                 240

Leu Phe Ser Arg Phe Arg Arg Asp Leu Glu Ser Gly Lys Leu Lys Arg
                245                 250                 255

Asn Phe Gln Lys Val Asn Pro Glu Gly Leu Ile Lys Glu Phe Ser Glu
```

```
                260                 265                 270
Leu Tyr Glu Asn Leu Ala Asp Ser Asp Ile Leu Thr Leu Ser Arg
            275                 280                 285
Glu Ala Val Glu Ser Cys Pro Leu Met Arg Phe Ile Thr Ala Glu Thr
290                 295                 300
His Gly His Glu Arg Gly Ser Glu Thr Ser Thr Glu Tyr Glu Arg Leu
305                 310                 315                 320
Leu Ser Met Leu Asn Lys Val Lys Ser Leu Lys Leu Leu Asn Thr Arg
                325                 330                 335
Arg Arg Gln Leu Leu Asn Leu Asp Val Leu Cys Leu Ser Ser Leu Ile
            340                 345                 350
Lys Gln Ser Lys Phe Lys Gly Leu Lys Asn Asp Lys His Trp Val Gly
            355                 360                 365
Cys Cys Tyr Ser Ser Val Asn Asp Arg Leu Val Ser Phe His Ser Thr
            370                 375                 380
Lys Glu Glu Phe Ile Arg Leu Leu Arg Asn Arg Lys Lys Ser Lys Val
385                 390                 395                 400
Phe Arg Lys Val Ser Phe Glu Glu Leu Phe Arg Ala Ser Ile Ser Glu
                405                 410                 415
Phe Ile Ala Lys Ile Gln Lys Cys Leu Leu Val Val Gly Leu Ser Phe
            420                 425                 430
Glu His Tyr Gly Leu Ser Glu His Leu Glu Gln Glu Cys His Ile Pro
            435                 440                 445
Phe Thr Glu Phe Glu Asn Phe Met Lys Ile Gly Ala His Pro Ile Met
            450                 455                 460
Tyr Tyr Thr Lys Phe Glu Asp Tyr Asn Phe Gln Pro Ser Thr Glu Gln
465                 470                 475                 480
Leu Lys Asn Ile Gln Ser Leu Arg Arg Leu Ser Ser Val Cys Leu Ala
                485                 490                 495
Leu Thr Asn Ser Met Lys Thr Ser Ser Val Ala Arg Leu Arg Gln Asn
            500                 505                 510
Gln Ile Gly Ser Val Arg Tyr Gln Val Val Glu Cys Lys Glu Val Phe
            515                 520                 525
Cys Gln Val Ile Lys Leu Asp Ser Glu Glu Tyr His Leu Leu Tyr Gln
            530                 535                 540
Lys Thr Gly Glu Ser Ser Arg Cys Tyr Ser Ile Gln Gly Pro Asp Gly
545                 550                 555                 560
His Leu Ile Ser Phe Tyr Ala Asp Pro Lys Arg Phe Phe Leu Pro Ile
                565                 570                 575
Phe Ser Asp Glu Val Leu Tyr Asn Met Ile Asp Ile Met Ile Ser Trp
            580                 585                 590
Ile Arg Ser Cys Pro Asp Leu Lys Asp Cys Leu Thr Asp Ile Glu Val
            595                 600                 605
Ala Leu Arg Thr Leu Leu Leu Met Leu Thr Asn Pro Thr Lys Arg
            610                 615                 620
Asn Gln Lys Gln Val Gln Ser Val Arg Tyr Leu Val Met Ala Ile Val
625                 630                 635                 640
Ser Asp Phe Ser Ser Thr Ser Leu Met Asp Lys Leu Arg Glu Asp Leu
                645                 650                 655
Ile Thr Pro Ala Glu Lys Val Val Tyr Lys Leu Leu Arg Phe Leu Ile
            660                 665                 670
Lys Thr Ile Phe Gly Thr Gly Glu Lys Val Leu Leu Ser Ala Lys Phe
            675                 680                 685
```

-continued

```
Lys Phe Met Leu Asn Val Ser Tyr Leu Cys His Leu Ile Thr Lys Glu
        690                 695                 700
Thr Pro Asp Arg Leu Thr Asp Gln Ile Lys Cys Phe Glu Lys Phe Phe
705                 710                 715                 720
Glu Pro Lys Ser Gln Phe Gly Phe Val Asn Pro Lys Glu Ala Ile
                725                 730                 735
Thr Pro Glu Glu Glu Cys Val Phe Tyr Glu Gln Met Lys Arg Phe Thr
                740                 745                 750
Ser Lys Glu Ile Asp Cys Gln His Thr Thr Pro Gly Val Asn Leu Glu
                755                 760                 765
Ala Phe Ser Leu Met Val Ser Ser Phe Asn Asn Gly Thr Leu Ile Phe
        770                 775                 780
Lys Gly Glu Lys Lys Leu Asn Ser Leu Asp Pro Met Thr Asn Ser Gly
785                 790                 795                 800
Cys Ala Thr Ala Leu Asp Leu Ala Ser Asn Lys Ser Val Val Val Asn
                805                 810                 815
Lys His Leu Asn Gly Glu Arg Leu Leu Glu Tyr Asp Phe Asn Lys Leu
                820                 825                 830
Leu Val Ser Ala Val Ser Gln Ile Thr Glu Ser Phe Val Arg Lys Gln
                835                 840                 845
Lys Tyr Lys Leu Ser His Ser Asp Tyr Glu Tyr Lys Val Ser Lys Leu
        850                 855                 860
Val Ser Arg Leu Val Ile Gly Ser Lys Gly Glu Glu Thr Gly Arg Ser
865                 870                 875                 880
Glu Asp Asn Leu Ala Glu Ile Cys Phe Asp Gly Glu Glu Thr Ser
                885                 890                 895
Phe Phe Lys Ser Leu Glu Glu Lys Val Asn Thr Thr Ile Ala Arg Tyr
                900                 905                 910
Arg Arg Gly Arg Arg Ala Asn Asp Lys Gly Asp Gly Glu Lys Leu Thr
                915                 920                 925
Asn Thr Lys Gly Leu His His Leu Gln Leu Ile Leu Thr Gly Lys Met
        930                 935                 940
Ala His Leu Arg Lys Val Ile Leu Ser Glu Ile Ser Phe His Leu Val
945                 950                 955                 960
Glu Asp Phe Asp Pro Ser Cys Leu Thr Asn Asp Asp Met Lys Phe Ile
                965                 970                 975
Cys Glu Ala Val Glu Gly Ser Thr Glu Leu Ser Pro Leu Tyr Phe Thr
                980                 985                 990
Ser Val Ile Lys Asp Gln Cys Gly Leu Asp Glu Met Ala Lys Asn Leu
        995                 1000                1005
Cys Arg Lys Phe Phe Ser Glu Asn Asp Trp Phe Ser Cys Met Lys Met
    1010                1015                1020
Ile Leu Leu Gln Met Asn Ala Asn Ala Tyr Ser Gly Lys Tyr Arg His
1025                1030                1035                1040
Met Gln Arg Gln Gly Leu Asn Phe Lys Phe Asp Trp Asp Lys Leu Glu
                1045                1050                1055
Glu Asp Val Arg Ile Ser Glu Arg Glu Ser Asn Ser Glu Ser Leu Ser
            1060                1065                1070
Lys Ala Leu Ser Leu Thr Lys Cys Met Ser Ala Ala Leu Lys Asn Leu
        1075                1080                1085
Cys Phe Tyr Ser Glu Glu Ser Pro Thr Ser Tyr Thr Ser Val Gly Pro
    1090                1095                1100
```

-continued

```
Asp Ser Gly Arg Leu Lys Phe Ala Leu Ser Tyr Lys Glu Gln Val Gly
1105                1110                1115                1120

Gly Asn Arg Glu Leu Tyr Ile Gly Asp Leu Arg Thr Lys Met Phe Thr
            1125                1130                1135

Arg Leu Ile Glu Asp Tyr Phe Glu Ser Phe Ser Ser Phe Ser Gly
        1140                1145                1150

Ser Cys Leu Asn Asn Asp Lys Glu Phe Glu Asn Ala Ile Leu Ser Met
    1155                1160                1165

Thr Ile Asn Val Arg Glu Gly Phe Leu Asn Tyr Ser Met Asp His Ser
1170                1175                1180

Lys Trp Gly Pro Met Met Cys Pro Phe Leu Phe Leu Met Phe Leu Gln
1185                1190                1195                1200

Asn Leu Lys Leu Gly Asp Asp Gln Tyr Val Arg Ser Gly Lys Asp His
            1205                1210                1215

Val Ser Thr Leu Leu Thr Trp His Met His Lys Leu Val Glu Val Pro
            1220                1225                1230

Phe Pro Val Val Asn Ala Met Met Lys Ser Tyr Val Lys Ser Lys Leu
        1235                1240                1245

Lys Leu Leu Arg Gly Ser Glu Thr Thr Val Thr Glu Arg Ile Phe Arg
1250                1255                1260

Gln Tyr Phe Glu Met Gly Ile Val Pro Ser His Ile Ser Ser Leu Ile
1265                1270                1275                1280

Asp Met Gly Gln Gly Ile Leu His Asn Ala Ser Asp Phe Tyr Gly Leu
        1285                1290                1295

Leu Ser Glu Arg Phe Ile Asn Tyr Cys Ile Gly Val Ile Phe Gly Glu
        1300                1305                1310

Arg Pro Glu Ala Tyr Thr Ser Ser Asp Asp Gln Ile Thr Leu Phe Asp
        1315                1320                1325

Arg Arg Leu Ser Asp Leu Val Val Ser Asp Pro Glu Glu Val Leu Val
    1330                1335                1340

Leu Leu Glu Phe Gln Ser His Leu Ser Gly Leu Leu Asn Lys Phe Ile
1345                1350                1355                1360

Ser Pro Lys Ser Val Ala Gly Arg Phe Ala Ala Glu Phe Lys Ser Arg
            1365                1370                1375

Phe Tyr Val Trp Gly Glu Glu Val Pro Leu Leu Thr Lys Phe Val Ser
            1380                1385                1390

Ala Ala Leu His Asn Val Lys Cys Lys Glu Pro His Gln Leu Cys Glu
        1395                1400                1405

Thr Ile Asp Thr Ile Ala Asp Gln Ala Ile Ala Asn Gly Val Pro Val
1410                1415                1420

Ser Leu Val Asn Ser Ile Gln Arg Arg Thr Leu Asp Leu Leu Lys Tyr
1425                1430                1435                1440

Ala Asn Phe Pro Leu Asp Pro Phe Leu Leu Asn Thr Asn Thr Asp Val
            1445                1450                1455

Lys Asp Trp Leu Asp Gly Ser Arg Gly Tyr Arg Ile Gln Arg Leu Ile
            1460                1465                1470

Glu Glu Leu Cys Pro Asn Glu Thr Lys Val Val Arg Lys Leu Val Arg
        1475                1480                1485

Lys Leu His His Lys Leu Lys Asn Gly Glu Phe Asn Glu Glu Phe Phe
    1490                1495                1500

Leu Asp Leu Phe Asn Arg Asp Lys Thr Glu Ala Ile Leu Gln Leu Gly
1505                1510                1515                1520

Asp Leu Leu Gly Leu Glu Glu Asp Leu Asn Gln Leu Ala Asp Val Asn
```

-continued

```
                1525                1530                1535
Trp Leu Asn Leu Asn Glu Met Phe Pro Leu Arg Met Val Leu Arg Gln
        1540                1545                1550

Lys Val Val Tyr Pro Ser Val Met Thr Phe Gln Glu Glu Arg Ile Pro
    1555                1560                1565

Ser Leu Ile Lys Thr Leu Gln Asn Lys Leu Cys Ser Lys Phe Thr Arg
    1570                1575                1580

Gly Ala Gln Lys Leu Leu Ser Glu Ala Ile Asn Lys Ser Ala Phe Gln
1585                1590                1595                1600

Ser Cys Ile Ser Ser Gly Phe Ile Gly Leu Cys Lys Thr Leu Gly Ser
            1605                1610                1615

Arg Cys Val Arg Asn Lys Asn Arg Glu Asn Leu Tyr Ile Lys Lys Leu
        1620                1625                1630

Leu Glu Asp Leu Thr Thr Asp Asp His Val Thr Arg Val Cys Asn Arg
    1635                1640                1645

Asp Gly Ile Thr Leu Tyr Ile Cys Asp Lys Gln Ser His Pro Glu Ala
    1650                1655                1660

His Arg Asp His Ile Cys Leu Leu Arg Pro Leu Leu Trp Asp Tyr Ile
1665                1670                1675                1680

Cys Ile Ser Leu Ser Asn Ser Phe Glu Leu Gly Val Trp Val Leu Ala
            1685                1690                1695

Glu Pro Thr Lys Gly Lys Asn Asn Ser Glu Asn Leu Thr Leu Lys His
        1700                1705                1710

Leu Asn Pro Cys Asp Tyr Val Ala Arg Lys Pro Glu Ser Ser Arg Leu
    1715                1720                1725

Leu Glu Asp Lys Val Asn Leu Asn Gln Val Ile Gln Ser Val Arg Arg
    1730                1735                1740

Leu Tyr Pro Lys Ile Phe Glu Asp Gln Leu Leu Pro Phe Met Ser Asp
1745                1750                1755                1760

Met Ser Ser Lys Asn Met Arg Trp Ser Pro Arg Ile Lys Phe Leu Asp
            1765                1770                1775

Leu Cys Val Leu Ile Asp Ile Asn Ser Glu Ser Leu Ser Leu Ile Ser
        1780                1785                1790

His Val Val Lys Trp Lys Arg Asp Glu His Tyr Thr Val Leu Phe Ser
    1795                1800                1805

Asp Leu Ala Asn Ser His Gln Arg Ser Asp Ser Ser Leu Val Asp Glu
    1810                1815                1820

Phe Val Val Ser Thr Arg Asp Val Cys Lys Asn Phe Leu Lys Gln Val
1825                1830                1835                1840

Tyr Phe Glu Ser Phe Val Arg Glu Phe Val Ala Thr Thr Arg Thr Leu
            1845                1850                1855

Gly Asn Phe Ser Trp Phe Pro His Lys Glu Met Met Pro Ser Glu Asp
        1860                1865                1870

Gly Ala Glu Ala Leu Gly Pro Phe Gln Ser Phe Val Ser Lys Val Val
    1875                1880                1885

Asn Lys Asn Val Glu Arg Pro Met Phe Arg Asn Asp Leu Gln Phe Gly
    1890                1895                1900

Phe Gly Trp Phe Ser Tyr Arg Met Gly Asp Val Val Cys Asn Ala Ala
1905                1910                1915                1920

Met Leu Ile Arg Gln Gly Leu Thr Asn Pro Lys Ala Phe Lys Ser Leu
            1925                1930                1935

Lys Asp Leu Trp Asp Tyr Met Leu Asn Tyr Thr Lys Gly Val Leu Glu
        1940                1945                1950
```

```
Phe Ser Ile Ser Val Asp Phe Thr His Asn Gln Asn Thr Asp Cys
        1955                1960                1965

Leu Arg Lys Phe Ser Leu Ile Phe Leu Val Arg Cys Gln Leu Gln Asn
    1970                1975                1980

Pro Gly Val Ala Glu Leu Leu Ser Cys Ser His Leu Phe Lys Gly Glu
1985                1990                1995                2000

Ile Asp Arg Arg Met Leu Asp Glu Cys Leu His Leu Leu Arg Thr Asp
            2005                2010                2015

Ser Val Phe Lys Val Asn Asp Gly Val Phe Asp Ile Arg Ser Glu Glu
                2020                2025                2030

Phe Glu Asp Tyr Met Glu Asp Pro Leu Ile Leu Gly Asp Ser Leu Glu
        2035                2040                2045

Leu Glu Leu Leu Gly Ser Lys Arg Ile Leu Asp Gly Ile Arg Ser Ile
    2050                2055                2060

Asp Phe Glu Arg Val Gly Pro Gly Trp Glu Pro Val Pro Leu Thr Val
2065                2070                2075                2080

Lys Met Gly Ala Leu Phe Glu Gly Arg Asn Leu Val Gln Asn Ile Ile
            2085                2090                2095

Val Lys Leu Glu Thr Lys Asp Met Lys Val Phe Leu Ala Gly Leu Glu
                2100                2105                2110

Gly Tyr Glu Lys Ile Ser Asp Val Leu Gly Asn Leu Phe Leu His Arg
        2115                2120                2125

Phe Arg Thr Gly Glu His Leu Leu Gly Ser Glu Ile Ser Val Ile Leu
    2130                2135                2140

Gln Glu Leu Cys Ile Asp Arg Ser Ile Leu Ile Pro Leu Ser Leu
2145                2150                2155                2160

Leu Pro Asp Trp Phe Ala Phe Lys Asp Cys Arg Leu Cys Phe Ser Lys
            2165                2170                2175

Ser Arg Ser Thr Leu Met Tyr Glu Ile Val Gly Gly Arg Phe Arg Leu
                2180                2185                2190

Lys Gly Arg Ser Cys Asp Asp Trp Leu Gly Gly Ser Val Ala Glu Asp
        2195                2200                2205

Ile Asp
  2210

<210> SEQ ID NO 8
<211> LENGTH: 95
<212> TYPE: PRT
<213> ORGANISM: Lymphocytic choriomeningitis virus
<220> FEATURE:
<223> OTHER INFORMATION: unknown protein

<400> SEQUENCE: 8

Met Ser Ser Ala Thr Asp Pro Pro Ser Gln Ser Ser Gln Asp Leu Pro
1               5                   10                  15

Leu Ser Leu Asn Leu Pro Pro Thr Ile Ser Tyr Ile Lys Val Leu Leu
            20                  25                  30

Asp Leu Leu Lys Gln Ser Leu Gln Ser Leu Lys Ala Asn Gln Ser Gly
        35                  40                  45

Lys Ser Asp Ser Gly Ile Ser Arg Ile Asp Leu Ser Ile His Ser Ser
    50                  55                  60

Trp Arg Ile Thr Leu Ile Ser Glu Pro Asn Lys Cys Ser Pro Val Leu
65                  70                  75                  80

Asn Arg Cys Arg Lys Arg Phe Pro Arg Thr Ser Leu Ile Phe Ser
            85                  90                  95
```

<210> SEQ ID NO 9
<211> LENGTH: 4695
<212> TYPE: DNA
<213> ORGANISM: Homo sapiens

<400> SEQUENCE: 9

```
cccgggctgg gctgagaccc gcagaggaag acgctctagg gatttgtccc ggactagcga      60
gatggcaagg ctgaggacgg gaggctgatt gagaggcgaa ggtacaccct aatctcaata     120
caacctttgg agctaagcca gcaatggtag agggaagatt ctgcacgtcc cttccaggcg     180
gcctccccgt caccaccccc cccaacccgc cccgaccgga gctgagagta attcatacaa     240
aaggactcgc ccctgccttg gggaatccca gggaccgtcg ttaaactccc actaacgtag     300
aacccagaga tcgctgcgtt cccgccccct cacccgcccg ctctcgtcat cactgaggtg     360
gagaagagca tgcgtgaggc tccggtgccc gtcagtgggc agagcgcaca tcgcccacag     420
tccccgagaa gttgggggga ggggtcggca attgaaccgg tgcctagaga aggtggcgcg     480
gggtaaactg ggaaagtgat gtcgtgtact ggctccgcct ttttcccgag ggtgggggag     540
aaccgtatat aagtgcagta gtcgccgtga acgttctttt tcgcaacggg tttgccgcca     600
gaacacaggt aagtgccgtg tgtggttccc gcgggcctgg cctctttacg ggttatggcc     660
cttgcgtgcc ttgaattact tccacgcccc tggctgcagt acgtgattct tgatcccgag     720
cttcggttg gaagtgggtg ggagagttcg aggccttgcg cttaaggagc cccttcgcct     780
cgtgcttgag ttgaggcctg gcctgggcgc tggggccgcc gcgtgcgaat ctggtggcac     840
cttcgcgcct gtctcgctgc tttcgataag tctctagcca tttaaaattt ttgatgacct     900
gctgcgacgc ttttttttctg gcaagatagt cttgtaaatg cgggccaaga tctgcacact     960
ggtatttcgg tttttggggc gcgggcggc gacggggccc gtgcgtccca gcgcacatgt    1020
tcggcgaggc ggggcctgcg agcgcggcca ccgagaatcg gacgggggta gtctcaagct    1080
ggccggcctg ctctggtgcc tggcctcgcg ccgccgtgta tcgccccgcc ctgggcggca    1140
aggctggccc ggtcggcacc agttgcgtga gcggaaagat ggccgcttcc cggccctgct    1200
gcagggagct caaaatggag gacgcggcgc tcgggagagc gggcgggtga gtcacccaca    1260
caaaggaaaa gggcctttcc gtcctcagcc gtcgcttcat gtgactccac ggagtaccgg    1320
gcgccgtcca ggcacctcga ttagttctcg agcttttgga gtacgtcgtc tttaggttgg    1380
ggggagggt tttatgcgat ggagtttccc cacactgagt gggtggagac tgaagttagg    1440
ccagcttggc acttgatgta attctccttg gaatttgccc tttttgagtt tggatcttgg    1500
ttcattctca agcctcagac agtggttcaa agttttttc ttccatttca ggtgtcgtga    1560
aaactacccc taaaagccaa aatgggaaag gaaaagactc atatcaacat tgtcgtcatt    1620
ggacacgtag attcgggcaa gtccaccact actggccatc tgatctataa atgcggtggc    1680
atcgacaaaa gaaccattga aaaatttgag aaggaggctg ctgaggtatg tttaatacca    1740
gaaagggaaa gatcaactaa aatgagtttt accagcagaa tcattaggtg atttccccag    1800
aactagtgag tggtttagat ctgaatgcta atagttaaga ccttacttat gaataatttt    1860
tgcttttggt gacttctgta atcgtattgc tagtgagtag atttggatgt taatagttaa    1920
gatcctactt ataaaagttt gattttggt tgcttctgta acccaaagtg accaaaatca    1980
ctttggactt ggagttgtaa agtggaaact gccaattaag ggctggggac aaggaaattg    2040
aagctggagt ttgtgttta gtaaccaagt aacgactctt aatccttaca gatgggaaag    2100
```

```
ggctccttca agtatgcctg ggtcttggat aaactgaaag ctgagcgtga acgtggtatc    2160
accattgata tctccttgtg gaaatttgag accagcaagt actatgtgac tatcattgat    2220
gccccaggac acagagactt tatcaaaaac atgattacag ggacatctca ggttgggatt    2280
aataattcta ggtttcttta tcccaaaagg cttgctttgt acactggttt tgtcatttgg    2340
agagttgaca gggatatgtc tttgctttct ttaaaggctg actgtgctgt cctgattgtt    2400
gctgctggtg ttggtgaatt tgaagctggt atctccaaga atgggcagac ccgagagcat    2460
gcccttctgg cttacacact gggtgtgaaa caactaattg tcggtgttaa caaaatggat    2520
tccactgagc caccctacag ccagaagaga tatgaggaaa ttgttaagga agtcagcact    2580
tacattaaga aaattggcta caccccgac acagtagcat ttgtgccaat ttctggttgg    2640
aatggtgaca acatgctgga gccaagtgct aacgtaagtg gctttcaaga ccattgttaa    2700
aaagctctgg gaatggcgat tcatgctta cacaaattgg catgcttgtg tttcagatgc    2760
cttggttcaa gggatggaaa gtcacccgta aggatggcaa tgccagtgga accacgctgc    2820
ttgaggctct ggactgcatc ctaccaccaa ctcgtccaac tgacaagccc ttgcgcctgc    2880
ctctccagga tgtctacaaa attggtggta agttggctgt aaacaaagtt gaatttgagt    2940
tgatagagta ctgtctgcct tcataggtat ttagtatgct gtaaatattt ttaggtattg    3000
gtactgttcc tgttggccga gtggagactg gtgttctcaa acccggtatg gtggtcacct    3060
ttgctccagt caacgttaca acggaagtaa aatctgtcga aatgcaccat gaagctttga    3120
gtgaagctct tcctggggac aatgtgggct tcaatgtcaa gaatgtgtct gtcaaggatg    3180
ttcgtcgtgg caacgttgct ggtgacagca aaaatgaccc accaatggaa gcagctggct    3240
tcactgctca ggtaacaatt taaagtaaca ttaacttatt gcagaggcta aagtcatttg    3300
agactttgga tttgcactga atgcaaatct ttttccaag gtgattatcc tgaaccatcc    3360
aggccaaata agcgccggct atgccctgt attggattgc cacacggctc acattgcatg    3420
caagtttgct gagctgaagg aaaagattga tcgccgttct ggtaaaaagc tggaagatgg    3480
ccctaaattc ttgaagtctg gtgatgctgc cattgttgat atggttcctg caagcccat    3540 gtgtgttgag agcttctcag actatccacc tttgggtaag gatgactact taaatgtaaa    3600
aaagttgtgt taaagatgaa aaatacaact gaacagtact ttgggtaata attaactttt    3660
tttttaatag gtcgctttgc tgttcgtgat atgagacaga cagttgcggt gggtgtcatc    3720
aaagcagtgg acaagaaggc tgctggagct ggcaaggtca ccaagtctgc ccagaaagct    3780
cagaaggcta aatgaatatt atccctaata cctgccaccc cactcttaat cagtggtgga    3840
agaacggtct cagaactgtt tgtttcaatt ggccattta gtttagtagt aaaagactgg    3900
ttaatgataa caatgcatcg taaaaccttc agaaggaaag gagaatgttt tgtggaccac    3960
tttggttttc tttttttgcgt gtggcagttt taagttatta gttttaaaa tcagtacttt    4020 ttaatggaaa caacttgacc aaaaatttgt cacagaattt tgagacccat taaaaaagtt    4080
aaatgagaaa cctgtgtgtt cctttggtca acaccgagac atttaggtga agacatcta    4140 attctggttt tacgaatctg gaaacttctt gaaaatgtaa ttcttgagtt aacacttctg    4200
ggtggagaat agggttgttt tcccccaca taattggaag gggaaggaat atcatttaaa    4260
gctatgggag ggtttctttg attacaacac tggagagaaa tgcagcatgt tgctgattgc    4320
ctgtcactaa aacaggccaa aaactgagtc cttgggttgc atagaaagct tcatgttgct    4380
aaaccaatgt taagtgaatc tttggaaaca aaatgttccc aaattactgg gatgtgcatg    4440
ttgaaacgtg ggttaaaatg actgggcagt gaaagttgac tatttgccat gacataagaa    4500
```

```
ataagtgtag tggctagtgt acaccctatg agtggaaggg tccattttga agtcagtgga      4560
gtaagcttta tgccattttg atggtttcac aagttctatt gagtgctatt cagaatagga      4620
acaaggttct aatagaaaaa gatggcaatt tgaagtagct ataaaattag actaattaca      4680
ttgcttttct ccgac                                                       4695
```

<210> SEQ ID NO 10
<211> LENGTH: 462
<212> TYPE: PRT
<213> ORGANISM: Homo sapiens
<220> FEATURE:
<223> OTHER INFORMATION: elongation factor EF-1-alpha

<400> SEQUENCE: 10

```
Met Gly Lys Glu Lys Thr His Ile Asn Ile Val Val Ile Gly His Val
  1               5                  10                  15

Asp Ser Gly Lys Ser Thr Thr Thr Gly His Leu Ile Tyr Lys Cys Gly
             20                  25                  30

Gly Ile Asp Lys Arg Thr Ile Glu Lys Phe Glu Lys Glu Ala Ala Glu
         35                  40                  45

Met Gly Lys Gly Ser Phe Lys Tyr Ala Trp Val Leu Asp Lys Leu Lys
     50                  55                  60

Ala Glu Arg Glu Arg Gly Ile Thr Ile Asp Ile Ser Leu Trp Lys Phe
 65                  70                  75                  80

Glu Thr Ser Lys Tyr Tyr Val Thr Ile Ile Asp Ala Pro Gly His Arg
                 85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
    130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser
    210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
            260                 265                 270

Lys Pro Gly Met Val Val Thr Phe Ala Pro Val Asn Val Thr Thr Glu
        275                 280                 285

Val Lys Ser Val Glu Met His His Glu Ala Leu Ser Glu Ala Leu Pro
    290                 295                 300

Gly Asp Asn Val Gly Phe Asn Val Lys Asn Val Ser Val Lys Asp Val
305                 310                 315                 320
```

-continued

```
Arg Arg Gly Asn Val Ala Gly Asp Ser Lys Asn Asp Pro Met Glu
            325                 330                 335

Ala Ala Gly Phe Thr Ala Gln Val Ile Ile Leu Asn His Pro Gly Gln
            340                 345                 350

Ile Ser Ala Gly Tyr Ala Pro Val Leu Asp Cys His Thr Ala His Ile
            355                 360                 365

Ala Cys Lys Phe Ala Glu Leu Lys Glu Lys Ile Asp Arg Arg Ser Gly
            370                 375             380

Lys Lys Leu Glu Asp Gly Pro Lys Phe Leu Lys Ser Gly Asp Ala Ala
385                 390                 395                 400

Ile Val Asp Met Val Pro Gly Lys Pro Met Cys Val Glu Ser Phe Ser
                    405                 410                 415

Asp Tyr Pro Pro Leu Gly Arg Phe Ala Val Arg Asp Met Arg Gln Thr
                420                 425                 430

Val Ala Val Gly Val Ile Lys Ala Val Asp Lys Lys Ala Ala Gly Ala
                    435                 440                 445

Gly Lys Val Thr Lys Ser Ala Gln Lys Ala Gln Lys Ala Lys
            450                 455                 460
```

<210> SEQ ID NO 11
<211> LENGTH: 8332
<212> TYPE: DNA
<213> ORGANISM: Moloney murine leukemia virus

<400> SEQUENCE: 11

| | | | | | |
|---|---|---|---|---|---|
| tatgcgcctg | cgtcggtact | agttagctaa | ctagctctgt | atctggcgga | cccgtggtgg | 60 |
| aactgacgag | ttcggaacac | ccggccgcaa | ccctgggaga | cgtcccaggg | acttcggggg | 120 |
| ccgtttttgt | ggcccgacct | gagtccaaaa | atcccgatcg | ttttggactc | tttggtgcac | 180 |
| cccccttaga | ggagggatat | gtggttctgg | taggagacga | gaacctaaaa | cagttcccgc | 240 |
| ctccgtctga | attttttgctt | tcggtttggg | accgaagccg | cgccgcgcgt | cttgtctgct | 300 |
| gcagcatcgt | tctgtgttgt | ctctgtctga | ctgtgtttct | gtatttgtct | gagaatatgg | 360 |
| gccagactgt | taccactccc | ttaagtttga | ccttaggtca | ctggaaagat | gtcgagcgga | 420 |
| tcgctcacaa | ccagtcggta | gatgtcaaga | agagacgttg | ggttaccttc | tgctctgcag | 480 |
| aatggccaac | ctttaacgtc | ggatggccgc | gagacggcac | ctttaaccga | gacctcatca | 540 |
| cccaggttaa | gatcaaggtc | ttttcacctg | gcccgcatgg | acacccagac | caggtcccct | 600 |
| acatcgtgac | ctgggaagcc | ttggcttttg | acccccctcc | ctgggtcaag | cccttttgtac | 660 |
| accctaagcc | tccgcctcct | cttcctccat | ccgcccgtc | tctccccctt | gaacctcctc | 720 |
| gttcgacccc | gcctcgatcc | tccctttatc | cagccctcac | tccttctcta | ggcgccaaac | 780 |
| ctaaacctca | agttctttct | gacagtgggg | ggccgctcat | cgacctactt | acagaagacc | 840 |
| ccccgcctta | tagggaccca | agaccacccc | cttccgacag | ggacgaaat | ggtggagaag | 900 |
| cgaccctgc | gggagaggca | ccggacccct | ccccaatggc | atctcgccta | cgtgggagac | 960 |
| gggagccccc | tgtggccgac | tccactacct | cgcaggcatt | cccctccgc | gcaggaggaa | 1020 |
| acggacagct | tcaatactgg | ccgttctcct | cttctgacct | ttacaactgg | aaaaataata | 1080 |
| acccttcttt | ttctgaagat | ccaggtaaac | tgacagctct | gatcgagtct | gttctcatca | 1140 |
| cccatcagcc | cacctgggac | gactgtcagc | agctgttggg | gactctgctg | accggagaag | 1200 |
| aaaaacaacg | ggtgctctta | gaggctgaa | aggcggtgcg | gggcgatgat | gggcgcccca | 1260 |
| ctcaactgcc | caatgaagtc | gatgccgctt | ttcccctcga | gcgcccagac | tgggattaca | 1320 |

-continued

```
ccacccaggc aggtaggaac cacctagtcc actatcgcca gttgctccta gcgggtctcc    1380
aaaacgcggg cagaagcccc accaatttgg ccaaggtaaa aggaataaca caagggccca    1440
atgagtctcc ctcggccttc ctagagagac ttaaggaagc ctatcgcagg tacactcctt    1500
atgaccctga ggacccaggg caagaaacta atgtgtctat gtctttcatt tggcagtctg    1560
ccccagacat tgggagaaag ttagagaggt tagaagattt aaaaaacaag acgcttggag    1620
atttggttag agaggcagaa aagatcttta ataaacgaga accccggaa gaaagagagg     1680 aacgtatcag gagagaaaca gaggaaaaag aagaacgccg taggacagag gatgagcaga    1740
aagagaaaga aagagatcgt aggagacata gagagatgag caagctattg ccactgtcg     1800 ttagtggaca gaaacaggat agacagggag gagaacgaag gaggtcccaa ctcgatcgcg    1860
accagtgtgc ctactgcaaa gaaaaggggc actgggctaa agattgtccc aagaaaccac    1920
gaggacctcg gggaccaaga ccccagacct ccctcctgac cctagatgac tagggaggtc    1980
agggtcagga gccccccct gaacccagga taaccctcaa agtcgggggg caacccgtca     2040
ccttcctggt agatactggg gcccaacact ccgtgctgac ccaaaatcct ggacccctaa    2100
gtgataagtc tgcctgggtc caaggggcta ctggaggaaa gcggtatcgc tggaccacgg    2160
atcgcaaagt acatctagct accggtaagg tcacccactc tttcctccat gtaccagact    2220
gtccctatcc tctgttagga agagatttgc tgactaaact aaaagcccaa atccactttg    2280
agggatcagg agctcaggtt atgggaccaa tggggcagcc cctgcaagtg ttgaccctaa    2340
atatagaaga tgagcatcgg ctacatgaga cctcaaaaga gccagatgtt tctctagggt    2400
ccacatggct gtctgatttt cctcaggcct gggcggaaac cggggcatg ggactggcag     2460 ttcgccaagc tcctctgatc atacctctga agcaacctc taccccgtg tccataaaac      2520 aatacccat gtcacaagaa gccagactgg ggatcaagcc ccacatacag agactgttgg     2580
accagggaat actggtaccc tgccagtccc cctggaacac gccctgcta cccgttaaga     2640 aaccagggac taatgattat aggcctgtcc aggatctgag agaagtcaac aagcgggtgg    2700
aagacatcca ccccaccgtg cccaacccctt acaacctctt gagcgggctc ccaccgtccc   2760
accagtggta cactgtgctt gatttaaagg atgccttttt ctgcctgaga ctccacccca    2820
ccagtcagcc tctcttcgcc tttgagtgga gagatccaga gatgggaatc tcaggacaat    2880
tgacctggac cagactccca cagggtttca aaaacagtcc caccctgttt gatgaggcac    2940
tgcacagaga cctagcagac ttccggatcc agcaccaga cttgatcctg ctacagtacg     3000
tggatgactt actgctggcc gccacttctg agctagactg ccaacaaggt actcgggccc    3060
tgttacaaac cctagggaac ctcgggtatc gggcctcggc caagaaagcc caaatttgcc    3120
agaaacaggt caagtatctg gggtatcttc taaaagaggg tcagagatgg ctgactgagg    3180
ccagaaaaga gactgtgatg gggcagccta ctccgaagac ccctcgacaa ctaagggagt    3240
tcctagggac ggcaggcttc tgtcgcctct ggatccctgg gtttgcagaa atggcagccc    3300
ccttgtaccc tctcaccaaa acggggactc tgtttaattg gggcccagac caacaaaagg    3360
cctatcaaga aatcaagcaa gctcttctaa ctgccccagc cctgggttg ccagatttga     3420 ctaagcccctt tgaactcttt gtcgacgaga agcaggcta cgccaaaggt gtcctaacgc    3480
aaaaactggg accttggcgt cggccggtgg cctacctgtc caaaaagcta gacccagtag    3540
cagctgggtg gccccttgc ctacggatgg tagcagccat tgccgtactg acaaaggatg     3600
caggcaagct aaccatggga cagccactag tcattctggc cccccatgca gtagaggcac    3660
tagtcaaaca accccccgac cgctggcttt ccaacgcccg gatgactcac tatcaggcct    3720
```

```
tgcttttgga cacggaccgg gtccagttcg gaccggtggt agccctgaac ccggctacgc    3780
tgctcccact gcctgaggaa gggctgcaac acaactgcct tgatatcctg gccgaagccc    3840
acggaacccg acccgaccta acggaccagc cgctcccaga cgccgaccac acctggtaca    3900
cggatggaag cagtctctta caagagggac agcgtaaggc gggagctgcg gtgaccaccg    3960
agaccgaggt aatctgggct aaagcccgtc cagccggac atccgctcag cgggctgaac     4020
tgatagcact cacccaggcc ctaaagatgg cagaaggtaa aagctaaat gtttatactg      4080
atagccgtta tgcttttgct actgcccata tccatggaga aatatacaga aggcgtgggt    4140
tgctcacatc agaaggcaaa gagatcaaaa ataaagacga gatcttggcc ctactaaaag    4200
ccctctttct gcccaaaaga cttagcataa tccattgtcc aggacatcaa aagggacaca    4260
gcgccgaggc tagaggcaac cggatggctg accaagcggc ccgaaaggca gccatcacag    4320
agactccaga cacctctacc ctcctcatag aaaattcatc accctacacc tcagaacatt    4380
ttcattacac agtgactgat ataaaggacc taaccaagtt gggggccatt tatgataaaa    4440
caaagaagta ttgggtctac caaggaaaac ctgtgatgcc tgaccagttt acttttgaat    4500
tattagactt tcttcatcag ctgactcacc tcagcttctc aaaaatgaag gctctcctag    4560
agagaagcca cagtccctac tacatgctga accgggatcg aacactcaaa atatcactg      4620
agacctgcaa agcttgtgca caagtcaacg ccagcaagtc tgccgttaaa cagggaacta    4680
gggtccgcgg gcatcggccc ggcactcatt gggagatcga tttcaccgag ataaagcccg    4740
gattgtatgg ctataaatat cttctagttt ttatagatac cttttctggc tggatagaag    4800
ccttcccaac caagaaagaa accgccaagg tcgtaaccaa gaagctacta gaggagatct    4860
tccccaggtt cggcatgcct caggtattgg gaactgacaa tgggcctgcc ttcgtctcca    4920
aggtgagtca gacagtggcc gatctgttgg ggattgattg gaaattacat tgtgcataca    4980
gaccccaaag ctcaggccag gtagaaagaa tgaatagaac catcaaggag actttaacta    5040
aattaacgct tgcaactggc tctagagact gggtgctcct actcccctta gccctgtacc    5100
gagcccgcaa cacgccgggc ccccatggcc tcaccccata tgagatctta tatggggcac    5160
ccccgcccct tgtaaacttc cctgaccctg acatgacaag agttactaac agccctctc     5220
tccaagctca cttacaggct ctctacttag tccagcacga agtctggaga cctctggcgg    5280
cagcctacca agaacaactg gaccgaccgg tggtacctca cccttaccga gtcggcgaca    5340
cagtgtgggt ccgccgacac cagactaaga acctagaacc tcgctggaaa ggaccttaca    5400
cagtcctgct gaccaccccc accgccctca agtagacgg catcgcagct tggatacacg     5460
ccgcccacgt gaaggctgcc gaccccgggg gtggaccatc tctagactg acatggcgcg      5520
ttcaacgctc tcaaaacccc ttaaaaataa ggttaacccg cgaggccccc taatcccctt    5580
aattcttctg atgctcagag gggtcagtac tgcttcgccc ggctccagtc ctcatcaagt    5640
ctataatatc acctgggagg taaccaatgg agatcgggag acggtatggg caacttctgg    5700
caaccaccct ctgtggacct ggtggcctga ccttacccca gatttatgta tgttagccca    5760
ccatggacca tcttattggg ggctagaata tcaatcccct ttttcttctc cccgggggcc    5820
cccttgttgc tcagggggca gcagcccagg ctgttccaga gactgcgaag aacctttaac    5880
ctccctcacc cctcggtgca acactgcctg gaacagactc aagctagacc agacaactca    5940
taaatcaaat gagggatttt atgtttgccc cgggccccac cgcccccgag aatccaagtc    6000
atgtgggggt ccagactcct tctactgtgc ctattggggc tgtgagacaa ccggtagagc    6060
```

-continued

```
ttactggaag ccctcctcat catgggattt catcacagta aacaacaatc tcacctctga    6120
ccaggctgtc caggtatgca agataataa gtggtgcaac cccttagtta ttcggtttac    6180
agacgccggg agacgggtta cttcctggac cacaggacat tactgggct tacgtttgta    6240 tgtctccgga caagatccag ggcttacatt tgggatccga ctcagatacc aaaatctagg    6300
accccgcgtc ccaatagggc caaaccccgt tctggcagac caacagccac tctccaagcc    6360
caaacctgtt aagtcgcctt cagtcaccaa accacccagt gggactcctc tctccctac     6420 ccaacttcca ccggcgggaa cggaaaatag gctgctaaac ttagtagacg gagcctacca    6480
agccctcaac ctcaccagtc ctgacaaaac ccaagagtgc tggttgtgtc tagtagcggg    6540 accccctac tacgaagggg ttgccgtcct gggtacctac tccaaccata cctctgctcc     6600
agccaactgc tccgtggcct cccaacacaa gttgaccctg tccgaagtga ccggacaggg    6660
actctgcata ggagcagttc ccaaaacaca tcaggcccta tgtaatacca cccagacaag    6720
cagtcgaggg tcctattatc tagttgcccc tacaggtacc atgtgggctt gtagtaccgg    6780
gcttactcca tgcatctcca ccaccatact gaaccttacc actgattatt gtgttcttgt    6840
cgaactctgg ccaagagtca cctatcattc ccccagctat gtttacggcc tgtttgagag    6900
atccaaccga cacaaaagag aaccggtgtc gttaaccctg gccctattat tgggtggact    6960
aaccatgggg ggaattgccg ctggaatagg aacaggact actgctctaa tggccactca    7020
gcaattccag cagctccaag ccgcagtaca ggatgatctc agggaggttg aaaaatcaat    7080
ctctaaccta gaaaagtctc tcacttccct gtctgaagtt gtcctacaga atcgaagggg    7140
cctagacttg ttatttctaa agaaggagg gctgtgtgct gctctaaaag aagaatgttg    7200
cttctatgcg gaccacacag gactagtgag agacagcatg gccaaattga gagagaggct    7260
taatcagaga cagaaactgt ttgagtcaac tcaaggatgg tttgagggac tgtttaacag    7320 atcccccttgg tttaccacct tgatatctac cattatggga cccctcattg tactcctaat    7380
gattttgctc ttcggaccct gcattcttaa tcgattagtc caatttgtta aagacaggat    7440
atcagtggtc caggctctag ttttgactca acaatatcac cagctgaagc ctatagagta    7500
cgagccatag ataaaataaa agattttatt tagtctccag aaaaagggg gaatgaaaga    7560 ccccaccctgt aggtttggca agctagctta agtaacgcca ttttgcaagg catggaaaaa    7620
tacataactg agaatagaga agttcagatc aaggtcagga acagatggaa cagctgaata    7680
tgggccaaac aggatatctg tggtaagcag ttcctgcccc ggctcagggc caagaacaga    7740
tggaacagct gaatatgggc caaacaggat atctgtggta agcagttcct gccccggctc    7800
agggccaaga acagatggtc cccagatgcg gtccagccct cagcagtttc tagagaacca    7860
tcagatgttt ccaggtgcc ccaaggacct gaaatgaccc tgtgccttat ttgaactaac    7920
caatcagttc gcttctcgct tctgttcgcg cgcttctgct ccccgagctc aataaaagag    7980
cccacaaccc ctcactcggg gcgccagtcc tccgattgac tgagtcgccc gggtacccgt    8040
gtatccaata aaccctcttg cagttgcagc gccagtcctc cgattgactg agtcgcccgg    8100
gtacccgtgt atccaataaa ccctcttgca gttgcatccg acttgtggtc tcgctgttcc    8160
ttgggagggt ctcctctgag tgattgacta cccgtcagcg ggggtctttc atttgggggc    8220
tcgtccggga tcgggagacc cctgcccagg gaccaccgac ccaccaccgg gaggtaagct    8280
ggccagcaac ttatctgtgt ctgtccgatt gtctagtgtc tatgactgat tt            8332
```

<210> SEQ ID NO 12
<211> LENGTH: 538

<212> TYPE: PRT
<213> ORGANISM: Moloney murine leukemia virus
<220> FEATURE:
<223> OTHER INFORMATION: gag protein

<400> SEQUENCE: 12

```
Met Gly Gln Thr Val Thr Thr Pro Leu Ser Leu Thr Leu Gly His Trp
 1               5                  10                  15

Lys Asp Val Glu Arg Ile Ala His Asn Gln Ser Val Asp Val Lys Lys
                20                  25                  30

Arg Arg Trp Val Thr Phe Cys Ser Ala Glu Trp Pro Thr Phe Asn Val
         35                  40                  45

Gly Trp Pro Arg Asp Gly Thr Phe Asn Arg Asp Leu Ile Thr Gln Val
     50                  55                  60

Lys Ile Lys Val Phe Ser Pro Gly Pro His Gly His Pro Asp Gln Val
 65                  70                  75                  80

Pro Tyr Ile Val Thr Trp Glu Ala Leu Ala Phe Asp Pro Pro Pro Trp
                 85                  90                  95

Val Lys Pro Phe Val His Pro Lys Pro Pro Pro Leu Pro Pro Ser
                100                 105                 110

Ala Pro Ser Leu Pro Leu Glu Pro Pro Arg Ser Thr Pro Pro Arg Ser
             115                 120                 125

Ser Leu Tyr Pro Ala Leu Thr Pro Ser Leu Gly Ala Lys Pro Lys Pro
 130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
        195                 200                 205

Ser Thr Thr Ser Gln Ala Phe Pro Leu Arg Ala Gly Gly Asn Gly Gln
210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                245                 250                 255

Glu Ser Val Leu Ile Thr His Gln Pro Thr Trp Asp Asp Cys Gln Gln
            260                 265                 270

Leu Leu Gly Thr Leu Leu Thr Gly Glu Glu Lys Gln Arg Val Leu Leu
        275                 280                 285

Glu Ala Arg Lys Ala Val Arg Gly Asp Asp Gly Arg Pro Thr Gln Leu
290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
        355                 360                 365

Leu Glu Arg Leu Lys Glu Ala Tyr Arg Arg Tyr Thr Pro Tyr Asp Pro
370                 375                 380
```

-continued

```
Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
            405                 410                 415

Asn Lys Thr Leu Gly Asp Leu Val Arg Glu Ala Glu Lys Ile Phe Asn
            420                 425                 430

Lys Arg Glu Thr Pro Glu Glu Arg Glu Arg Ile Arg Arg Glu Thr
        435                 440                 445

Glu Glu Lys Glu Glu Arg Arg Thr Glu Asp Glu Gln Lys Glu Lys
    450                 455                 460

Glu Arg Asp Arg Arg His Arg Glu Met Ser Lys Leu Leu Ala Thr
465                 470                 475                 480

Val Val Ser Gly Lys Gln Asp Arg Gln Gly Gly Glu Arg Arg Arg
            485                 490                 495

Ser Gln Leu Asp Arg Asp Gln Cys Ala Tyr Cys Lys Glu Lys Gly His
            500                 505                 510

Trp Ala Lys Asp Cys Pro Lys Lys Pro Arg Gly Pro Arg Gly Pro Arg
            515                 520                 525

Pro Gln Thr Ser Leu Leu Thr Leu Asp Asp
            530                 535
```

<210> SEQ ID NO 13
<211> LENGTH: 1737
<212> TYPE: PRT
<213> ORGANISM: Moloney murine leukemia virus
<220> FEATURE:
<223> OTHER INFORMATION: gag-pol protein

<400> SEQUENCE: 13

```
Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Pro Pro Ser
            100                 105                 110

Ala Pro Ser Leu Pro Leu Glu Pro Pro Arg Ser Thr Pro Pro Arg Ser
            115                 120                 125

Ser Leu Tyr Pro Ala Leu Thr Pro Ser Leu Gly Ala Lys Pro Lys Pro
    130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
            195                 200                 205
```

-continued

```
Ser Thr Thr Ser Gln Ala Phe Pro Leu Arg Ala Gly Gly Asn Gly Gln
        210                 215                 220

Leu Gln Tyr Trp Pro Phe Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                    245                 250                 255

Glu Ser Val Leu Ile Thr His Gln Pro Thr Trp Asp Asp Cys Gln Gln
                260                 265                 270

Leu Leu Gly Thr Leu Leu Thr Gly Glu Glu Lys Gln Arg Val Leu Leu
            275                 280                 285

Glu Ala Arg Lys Ala Val Arg Gly Asp Asp Gly Arg Pro Thr Gln Leu
290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
            355                 360                 365

Leu Glu Arg Leu Lys Glu Ala Tyr Arg Arg Tyr Thr Pro Tyr Asp Pro
370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                405                 410                 415

Asn Lys Thr Leu Gly Asp Leu Val Arg Glu Ala Glu Lys Ile Phe Asn
                420                 425                 430

Lys Arg Glu Thr Pro Glu Glu Arg Glu Glu Arg Ile Arg Arg Glu Thr
            435                 440                 445

Glu Glu Lys Glu Glu Arg Arg Arg Thr Glu Asp Glu Gln Lys Glu Lys
450                 455                 460

Glu Arg Asp Arg Arg Arg His Arg Glu Met Ser Lys Leu Leu Ala Thr
465                 470                 475                 480

Val Val Ser Gly Gln Lys Gln Asp Arg Gln Gly Gly Glu Arg Arg Arg
                485                 490                 495

Ser Gln Leu Asp Arg Asp Gln Cys Ala Tyr Cys Lys Glu Lys Gly His
                500                 505                 510

Trp Ala Lys Asp Cys Pro Lys Lys Pro Arg Gly Pro Arg Gly Pro Arg
            515                 520                 525

Pro Gln Thr Ser Leu Leu Thr Leu Asp Asp Gly Gly Gln Gly Gln Glu
            530                 535                 540

Pro Pro Pro Glu Pro Arg Ile Thr Leu Lys Val Gly Gly Gln Pro Val
545                 550                 555                 560

Thr Phe Leu Val Asp Thr Gly Ala Gln His Ser Val Leu Thr Gln Asn
                565                 570                 575

Pro Gly Pro Leu Ser Asp Lys Ser Ala Trp Val Gln Gly Ala Thr Gly
                580                 585                 590

Gly Lys Arg Tyr Arg Trp Thr Thr Asp Arg Lys Val His Leu Ala Thr
            595                 600                 605

Gly Lys Val Thr His Ser Phe Leu His Val Pro Asp Cys Pro Tyr Pro
            610                 615                 620

Leu Leu Gly Arg Asp Leu Leu Thr Lys Leu Lys Ala Gln Ile His Phe
```

```
                625                 630                 635                 640
        Glu Gly Ser Gly Ala Gln Val Met Gly Pro Met Gly Gln Pro Leu Gln
                            645                 650                 655
        Val Leu Thr Leu Asn Ile Glu Asp Glu His Arg Leu His Glu Thr Ser
                        660                 665                 670
        Lys Glu Pro Asp Val Ser Leu Gly Ser Thr Trp Leu Ser Asp Phe Pro
                    675                 680                 685
        Gln Ala Trp Ala Glu Thr Gly Gly Met Gly Leu Ala Val Arg Gln Ala
                690                 695                 700
        Pro Leu Ile Ile Pro Leu Lys Ala Thr Ser Thr Pro Val Ser Ile Lys
        705                 710                 715                 720
        Gln Tyr Pro Met Ser Gln Glu Ala Arg Leu Gly Ile Lys Pro His Ile
                            725                 730                 735
        Gln Arg Leu Leu Asp Gln Gly Ile Leu Val Pro Cys Gln Ser Pro Trp
                        740                 745                 750
        Asn Thr Pro Leu Leu Pro Val Lys Lys Pro Gly Thr Asn Asp Tyr Arg
                    755                 760                 765
        Pro Val Gln Asp Leu Arg Glu Val Asn Lys Arg Val Glu Asp Ile His
                770                 775                 780
        Pro Thr Val Pro Asn Pro Tyr Asn Leu Leu Ser Gly Leu Pro Pro Ser
        785                 790                 795                 800
        His Gln Trp Tyr Thr Val Leu Asp Leu Lys Asp Ala Phe Phe Cys Leu
                            805                 810                 815
        Arg Leu His Pro Thr Ser Gln Pro Leu Phe Ala Phe Glu Trp Arg Asp
                        820                 825                 830
        Pro Glu Met Gly Ile Ser Gly Gln Leu Thr Trp Thr Arg Leu Pro Gln
                    835                 840                 845
        Gly Phe Lys Asn Ser Pro Thr Leu Phe Asp Glu Ala Leu His Arg Asp
                850                 855                 860
        Leu Ala Asp Phe Arg Ile Gln His Pro Asp Leu Ile Leu Leu Gln Tyr
        865                 870                 875                 880
        Val Asp Asp Leu Leu Leu Ala Ala Thr Ser Glu Leu Asp Cys Gln Gln
                            885                 890                 895
        Gly Thr Arg Ala Leu Leu Gln Thr Leu Gly Asn Leu Gly Tyr Arg Ala
                        900                 905                 910
        Ser Ala Lys Lys Ala Gln Ile Cys Gln Lys Gln Val Lys Tyr Leu Gly
                    915                 920                 925
        Tyr Leu Leu Lys Glu Gly Gln Arg Trp Leu Thr Glu Ala Arg Lys Glu
                930                 935                 940
        Thr Val Met Gly Gln Pro Thr Pro Lys Thr Pro Arg Gln Leu Arg Glu
        945                 950                 955                 960
        Phe Leu Gly Thr Ala Gly Phe Cys Arg Leu Trp Ile Pro Gly Phe Ala
                            965                 970                 975
        Glu Met Ala Ala Pro Leu Tyr Pro Leu Thr Lys Thr Gly Thr Leu Phe
                        980                 985                 990
        Asn Trp Gly Pro Asp Gln Gln Lys Ala Tyr Gln Glu Ile Lys Gln Ala
                    995                 1000                1005
        Leu Leu Thr Ala Pro Ala Leu Gly Leu Pro Asp Leu Thr Lys Pro Phe
            1010                1015                1020
        Glu Leu Phe Val Asp Glu Lys Gln Gly Tyr Ala Lys Gly Val Leu Thr
        1025                1030                1035                1040
        Gln Lys Leu Gly Pro Trp Arg Arg Pro Val Ala Tyr Leu Ser Lys Lys
                            1045                1050                1055
```

-continued

```
Leu Asp Pro Val Ala Ala Gly Trp Pro Pro Cys Leu Arg Met Val Ala
        1060                1065                1070

Ala Ile Ala Val Leu Thr Lys Asp Ala Gly Lys Leu Thr Met Gly Gln
    1075                1080                1085

Pro Leu Val Ile Leu Ala Pro His Ala Val Glu Ala Leu Val Lys Gln
    1090                1095                1100

Pro Pro Asp Arg Trp Leu Ser Asn Ala Arg Met Thr His Tyr Gln Ala
1105                1110                1115                1120

Leu Leu Leu Asp Thr Asp Arg Val Gln Phe Gly Pro Val Ala Leu
            1125                1130                1135

Asn Pro Ala Thr Leu Leu Pro Leu Pro Glu Glu Gly Leu Gln His Asn
        1140                1145                1150

Cys Leu Asp Ile Leu Ala Glu Ala His Gly Thr Arg Pro Asp Leu Thr
    1155                1160                1165

Asp Gln Pro Leu Pro Asp Ala Asp His Thr Trp Tyr Thr Asp Gly Ser
    1170                1175                1180

Ser Leu Leu Gln Glu Gly Gln Arg Lys Ala Gly Ala Ala Val Thr Thr
1185                1190                1195                1200

Glu Thr Glu Val Ile Trp Ala Lys Ala Leu Pro Ala Gly Thr Ser Ala
        1205                1210                1215

Gln Arg Ala Glu Leu Ile Ala Leu Thr Gln Ala Leu Lys Met Ala Glu
        1220                1225                1230

Gly Lys Lys Leu Asn Val Tyr Thr Asp Ser Arg Tyr Ala Phe Ala Thr
    1235                1240                1245

Ala His Ile His Gly Glu Ile Tyr Arg Arg Arg Gly Leu Leu Thr Ser
    1250                1255                1260

Glu Gly Lys Glu Ile Lys Asn Lys Asp Glu Ile Leu Ala Leu Leu Lys
1265                1270                1275                1280

Ala Leu Phe Leu Pro Lys Arg Leu Ser Ile Ile His Cys Pro Gly His
        1285                1290                1295

Gln Lys Gly His Ser Ala Glu Ala Arg Gly Asn Arg Met Ala Asp Gln
    1300                1305                1310

Ala Ala Arg Lys Ala Ala Ile Thr Glu Thr Pro Asp Thr Ser Thr Leu
    1315                1320                1325

Leu Ile Glu Asn Ser Ser Pro Tyr Thr Ser Glu His Phe His Tyr Thr
        1330                1335                1340

Val Thr Asp Ile Lys Asp Leu Thr Lys Leu Gly Ala Ile Tyr Asp Lys
1345                1350                1355                1360

Thr Lys Lys Tyr Trp Val Tyr Gln Gly Lys Pro Val Met Pro Asp Gln
        1365                1370                1375

Phe Thr Phe Glu Leu Leu Asp Phe Leu His Gln Leu Thr His Leu Ser
        1380                1385                1390

Phe Ser Lys Met Lys Ala Leu Leu Glu Arg Ser His Ser Pro Tyr Tyr
    1395                1400                1405

Met Leu Asn Arg Asp Arg Thr Leu Lys Asn Ile Thr Glu Thr Cys Lys
    1410                1415                1420

Ala Cys Ala Gln Val Asn Ala Ser Lys Ser Ala Val Lys Gln Gly Thr
1425                1430                1435                1440

Arg Val Arg Gly His Arg Pro Gly Thr His Trp Glu Ile Asp Phe Thr
            1445                1450                1455

Glu Ile Lys Pro Gly Leu Tyr Gly Tyr Lys Tyr Leu Leu Val Phe Ile
        1460                1465                1470
```

-continued

Asp Thr Phe Ser Gly Trp Ile Glu Ala Phe Pro Thr Lys Lys Glu Thr
1475                1480                1485

Ala Lys Val Val Thr Lys Lys Leu Leu Glu Glu Ile Phe Pro Arg Phe
1490                1495                1500

Gly Met Pro Gln Val Leu Gly Thr Asp Asn Gly Pro Ala Phe Val Ser
1505                1510                1515                1520

Lys Val Ser Gln Thr Val Ala Asp Leu Leu Gly Ile Asp Trp Lys Leu
         1525                1530                1535

His Cys Ala Tyr Arg Pro Gln Ser Ser Gly Gln Val Glu Arg Met Asn
         1540                1545                1550

Arg Thr Ile Lys Glu Thr Leu Thr Lys Leu Thr Leu Ala Thr Gly Ser
         1555                1560                1565

Arg Asp Trp Val Leu Leu Pro Leu Ala Leu Tyr Arg Ala Arg Asn
     1570                1575                1580

Thr Pro Gly Pro His Gly Leu Thr Pro Tyr Glu Ile Leu Tyr Gly Ala
1585                1590                1595                1600

Pro Pro Pro Leu Val Asn Phe Pro Asp Pro Asp Met Thr Arg Val Thr
             1605                1610                1615

Asn Ser Pro Ser Leu Gln Ala His Leu Gln Ala Leu Tyr Leu Val Gln
             1620                1625                1630

His Glu Val Trp Arg Pro Leu Ala Ala Ala Tyr Gln Glu Gln Leu Asp
         1635                1640                1645

Arg Pro Val Val Pro His Pro Tyr Arg Val Gly Asp Thr Val Trp Val
     1650                1655                1660

Arg Arg His Gln Thr Lys Asn Leu Glu Pro Arg Trp Lys Gly Pro Tyr
1665                1670                1675                1680

Thr Val Leu Leu Thr Thr Pro Thr Ala Leu Lys Val Asp Gly Ile Ala
             1685                1690                1695

Ala Trp Ile His Ala Ala His Val Lys Ala Ala Asp Pro Gly Gly Gly
             1700                1705                1710

Pro Ser Ser Arg Leu Thr Trp Arg Val Gln Arg Ser Gln Asn Pro Leu
         1715                1720                1725

Lys Ile Arg Leu Thr Arg Glu Ala Pro
     1730                1735

<210> SEQ ID NO 14
<211> LENGTH: 665
<212> TYPE: PRT
<213> ORGANISM: Moloney murine leukemia virus
<220> FEATURE:
<223> OTHER INFORMATION: env protein

<400> SEQUENCE: 14

Met Ala Arg Ser Thr Leu Ser Lys Pro Leu Lys Asn Lys Val Asn Pro
1               5                   10                  15

Arg Gly Pro Leu Ile Pro Leu Ile Leu Leu Met Leu Arg Gly Val Ser
             20                  25                  30

Thr Ala Ser Pro Gly Ser Ser Pro His Gln Val Tyr Asn Ile Thr Trp
         35                  40                  45

Glu Val Thr Asn Gly Asp Arg Glu Thr Val Trp Ala Thr Ser Gly Asn
     50                  55                  60

His Pro Leu Trp Thr Trp Trp Pro Asp Leu Thr Pro Asp Leu Cys Met
65                  70                  75                  80

Leu Ala His His Gly Pro Ser Tyr Trp Gly Leu Glu Tyr Gln Ser Pro
                 85                  90                  95

-continued

```
Phe Ser Ser Pro Pro Gly Pro Pro Cys Cys Ser Gly Gly Ser Ser Pro
            100                 105                 110

Gly Cys Ser Arg Asp Cys Glu Glu Pro Leu Thr Ser Leu Thr Pro Arg
            115                 120                 125

Cys Asn Thr Ala Trp Asn Arg Leu Lys Leu Asp Gln Thr Thr His Lys
            130                 135                 140

Ser Asn Glu Gly Phe Tyr Val Cys Pro Gly Pro His Arg Pro Arg Glu
145                     150                 155                 160

Ser Lys Ser Cys Gly Gly Pro Asp Ser Phe Tyr Cys Ala Tyr Trp Gly
                    165                 170                 175

Cys Glu Thr Thr Gly Arg Ala Tyr Trp Lys Pro Ser Ser Ser Trp Asp
                    180                 185                 190

Phe Ile Thr Val Asn Asn Leu Thr Ser Asp Gln Ala Val Gln Val
                195                 200                 205

Cys Lys Asp Asn Lys Trp Cys Asn Pro Leu Val Ile Arg Phe Thr Asp
            210                 215                 220

Ala Gly Arg Arg Val Thr Ser Trp Thr Gly His Tyr Trp Gly Leu
225                     230                 235                 240

Arg Leu Tyr Val Ser Gly Gln Asp Pro Gly Leu Thr Phe Gly Ile Arg
                    245                 250                 255

Leu Arg Tyr Gln Asn Leu Gly Pro Arg Val Pro Ile Gly Pro Asn Pro
            260                 265                 270

Val Leu Ala Asp Gln Gln Pro Leu Ser Lys Pro Lys Pro Val Lys Ser
            275                 280                 285

Pro Ser Val Thr Lys Pro Pro Ser Gly Thr Pro Leu Ser Pro Thr Gln
            290                 295                 300

Leu Pro Pro Ala Gly Thr Glu Asn Arg Leu Leu Asn Leu Val Asp Gly
305                     310                 315                 320

Ala Tyr Gln Ala Leu Asn Leu Thr Ser Pro Asp Lys Thr Gln Glu Cys
                    325                 330                 335

Trp Leu Cys Leu Val Ala Gly Pro Pro Tyr Tyr Glu Gly Val Ala Val
                    340                 345                 350

Leu Gly Thr Tyr Ser Asn His Thr Ser Ala Pro Ala Asn Cys Ser Val
            355                 360                 365

Ala Ser Gln His Lys Leu Thr Leu Ser Glu Val Thr Gly Gln Gly Leu
            370                 375                 380

Cys Ile Gly Ala Val Pro Lys Thr His Gln Ala Leu Cys Asn Thr Thr
385                     390                 395                 400

Gln Thr Ser Ser Arg Gly Ser Tyr Tyr Leu Val Ala Pro Thr Gly Thr
                    405                 410                 415

Met Trp Ala Cys Ser Thr Gly Leu Thr Pro Cys Ile Ser Thr Thr Ile
                    420                 425                 430

Leu Asn Leu Thr Thr Asp Tyr Cys Val Leu Val Glu Leu Trp Pro Arg
            435                 440                 445

Val Thr Tyr His Ser Pro Ser Tyr Val Tyr Gly Leu Phe Glu Arg Ser
450                     455                 460

Asn Arg His Lys Arg Glu Pro Val Ser Leu Thr Leu Ala Leu Leu Leu
465                     470                 475                 480

Gly Gly Leu Thr Met Gly Gly Ile Ala Ala Gly Ile Gly Thr Gly Thr
                    485                 490                 495

Thr Ala Leu Met Ala Thr Gln Gln Phe Gln Gln Leu Gln Ala Ala Val
                500                 505                 510

Gln Asp Asp Leu Arg Glu Val Glu Lys Ser Ile Ser Asn Leu Glu Lys
```

-continued

```
                515                 520                 525

Ser Leu Thr Ser Leu Ser Glu Val Leu Gln Asn Arg Arg Gly Leu
        530                 535                 540

Asp Leu Leu Phe Leu Lys Glu Gly Gly Leu Cys Ala Ala Leu Lys Glu
545                 550                 555                 560

Glu Cys Cys Phe Tyr Ala Asp His Thr Gly Leu Val Arg Asp Ser Met
                565                 570                 575

Ala Lys Leu Arg Glu Arg Leu Asn Gln Arg Gln Lys Leu Phe Glu Ser
            580                 585                 590

Thr Gln Gly Trp Phe Glu Gly Leu Phe Asn Arg Ser Pro Trp Phe Thr
        595                 600                 605

Thr Leu Ile Ser Thr Ile Met Gly Pro Leu Ile Val Leu Leu Met Ile
        610                 615                 620

Leu Leu Phe Gly Pro Cys Ile Leu Asn Arg Leu Val Gln Phe Val Lys
625                 630                 635                 640

Asp Arg Ile Ser Val Val Gln Ala Leu Val Leu Thr Gln Gln Tyr His
                645                 650                 655

Gln Leu Lys Pro Ile Glu Tyr Glu Pro
            660                 665

<210> SEQ ID NO 15
<211> LENGTH: 9709
<212> TYPE: DNA
<213> ORGANISM: Human immunodeficiency virus type 1

<400> SEQUENCE: 15
tggaagggct aatttggtcc caaaaaagac aagagatcct tgatctgtgg atctaccaca      60
cacaaggcta cttccctgat tggcagaact acacaccagg gccagggatc agatatccac     120
tgacctttgg atggtgcttc aagttagtac cagttgaacc agagcaagta gaagaggcca     180
aataaggaga gaagaacagc ttgttacacc ctatgagcca gcatgggatg gaggacccgg     240
agggagaagt attagtgtgg aagtttgaca gcctcctagc atttcgtcac atggcccgag     300
agctgcatcc ggagtactac aaagactgct gacatcgagc tttctacaag ggactttccg     360
ctggggactt tccagggagg tgtggcctgg gcgggactgg ggagtggcga gccctcagat     420
gctacatata agcagctgct ttttgcctgt actgggtctc tctggttaga ccagatctga     480
gcctgggagc tctctggcta actagggaac ccactgctta agcctcaata aagcttgcct     540
tgagtgctca aagtagtgtg tgcccgtctg ttgtgtgact ctggtaacta gagatccctc     600 agacccttt t agtcagtgtg gaaaatctct agcagtggcg cccgaacagg gacttgaaag     660
cgaaagtaaa gccagaggag atctctcgac gcaggactcg gcttgctgaa gcgcgcacgg     720
caagaggcga gggcggcga ctggtgagta cgccaaaaat tttgactagc ggaggctaga     780
aggagagaga tgggtgcgag agcgtcggta ttaagcgggg gagaattaga taatgggaa     840 aaaattcggt taaggccagg gggaagaaa caatataaac taaaacatat agtatgggca     900
agcagggagc tagaacgatt cgcagttaat cctggccttt tagagacatc agaaggctgt     960
agacaaatac tgggacagct acaaccatcc cttcagacag gatcagaaga acttagatca    1020
ttatataata caatagcagt cctctattgt gtgcatcaaa ggatagatgt aaaagacacc    1080
aaggaagcct tagataagat agaggaagag caaaacaaaa gtaagaaaaa ggcacagcaa    1140
gcagcagctg acacaggaaa caacagccag gtcagccaaa attaccctat agtgcagaac    1200
ctccaggggc aaatggtaca tcaggccata tcacctagaa ctttaaatgc atgggtaaaa    1260
```

-continued

| | | |
|---|---|---|
| gtagtagaag agaaggcttt cagcccagaa gtaatacccca tgttttcagc attatcagaa | 1320 |
| ggagccaccc cacaagattt aaataccatg ctaaacacag tgggggggaca tcaagcagcc | 1380 |
| atgcaaatgt taaaagagac catcaatgag gaagctgcag aatgggatag attgcatcca | 1440 |
| gtgcatgcag ggcctattgc accaggccag atgagagaac caaggggaag tgacatagca | 1500 |
| ggaactacta gtaccttca ggaacaaata ggatggatga cacataatcc acctatccca | 1560 |
| gtaggagaaa tctataaaag atggataatc ctgggattaa ataaaatagt aagaatgtat | 1620 |
| agccctacca gcattctgga cataagacaa ggaccaaagg aacccttag agactatgta | 1680 |
| gaccgattct ataaaactct aagagccgag caagcttcac aagaggtaaa aaattggatg | 1740 |
| acagaaacct tgttggtcca aaatgcgaac ccagattgta agactatttt aaaagcattg | 1800 |
| ggaccaggag cgacactaga agaaatgatg acagcatgtc agggagtggg gggacccggc | 1860 |
| cataaagcaa gagttttggc tgaagcaatg agccaagtaa caaatccagc taccataatg | 1920 |
| atacagaaag gcaattttag gaaccaaaga aagactgtta agtgtttcaa ttgtggcaaa | 1980 |
| gaagggcaca tagccaaaaa ttgcagggcc cctaggaaaa agggctgttg gaaatgtgga | 2040 |
| aaggaaggac accaaatgaa agattgtact gagagacagg ctaatttttt agggaagatc | 2100 |
| tggccttccc acaagggaag gccagggaat tttcttcaga gcagaccaga gccaacagcc | 2160 |
| ccaccagaag agagcttcag gtttggggaa gagacaacaa ctccctctca gaagcaggag | 2220 |
| ccgatagaca aggaactgta tcctttagct tccctcagat cactctttgg cagcgacccc | 2280 |
| tcgtcacaat aaagataggg gggcaattaa aggaagctct attagataca ggagcagatg | 2340 |
| atacagtatt agaagaaatg aatttgccag gaagatggaa accaaaaatg ataggggggaa | 2400 |
| ttggaggttt tatcaaagta ggacagtatg atcagatact catagaaatc tgcggacata | 2460 |
| aagctatagg tacagtatta gtaggaccta cacctgtcaa cataattgga agaaatctgt | 2520 |
| tgactcagat tggctgcact ttaaattttc ccattagtcc tattgagact gtaccagtaa | 2580 |
| aattaaagcc aggaatggat ggcccaaaag ttaaacaatg gccattgaca gaagaaaaaa | 2640 |
| taaaagcatt agtagaaatt tgtacagaaa tggaaaagga aggaaaaatt tcaaaaattg | 2700 |
| ggcctgaaaa tccatacaat actccagtat ttgccataaa gaaaaaagac agtactaaat | 2760 |
| ggagaaaatt agtagatttc agagaactta ataagagaac tcaagatttc tgggaagttc | 2820 |
| aattaggaat accacatcct gcagggttaa aacagaaaaa atcagtaaca gtactggatg | 2880 |
| tgggcgatgc atatttttca gttcccttag ataaagactt caggaagtat actgcattta | 2940 |
| ccatacctag tataaacaat gagacaccag ggattagata tcagtacaat gtgcttccac | 3000 |
| agggatggaa aggatcacca gcaatattcc agtgtagcat gacaaaaatc ttagagcctt | 3060 |
| ttagaaaaca aaatccagac atagtcatct atcaatacat ggatgatttg tatgtaggat | 3120 |
| ctgacttaga aatagggcag catagaacaa aaatagagga actgagacaa catctgttga | 3180 |
| ggtggggatt taccacacca gacaaaaaac atcagaaaga acctccattc ctttggatgg | 3240 |
| gttatgaact ccatcctgat aaatggacag tacagcctat agtgctgcca gaaaaggaca | 3300 |
| gctggactgt caatgacata cagaaattag tgggaaaatt gaattgggca agtcagattt | 3360 |
| atgcagggat taaagtaagg caattatgta aacttcttag gggaaccaaa gcactaacag | 3420 |
| aagtagtacc actaacagaa gaagcagagc tagaactggc agaaaacagg gagattctaa | 3480 |
| aagaaccggt acatggagtg tattatgacc catcaaaaga cttaatagca gaaatacaga | 3540 |
| agcaggggca aggccaatgg acatatcaaa tttatcaaga gccatttaaa aatctgaaaa | 3600 |
| caggaaaata tgcaagaatg aagggtgccc acactaatga tgtgaaacaa ttaacagagg | 3660 |

```
cagtacaaaa aatagccaca gaaagcatag taatatgggg aaagactcct aaatttaaat    3720
tacccataca aaaggaaaca tgggaagcat ggtggacaga gtattggcaa gccacctgga    3780
ttcctgagtg ggagtttgtc aatacccctc ccttagtgaa gttatggtac cagttagaga    3840
aagaacccat aataggagca gaaactttct atgtagatgg ggcagccaat agggaaacta    3900
aattaggaaa agcaggatat gtaactgaca gaggaagaca aaaagttgtc ccctaacgg     3960
acacaacaaa tcagaagact gagttacaag caattcatct agctttgcag gattcgggat    4020
tagaagtaaa catagtgaca gactcacaat atgcattggg aatcattcaa gcacaaccag    4080
ataagagtga atcagagtta gtcagtcaaa taatagagca gttaataaaa aaggaaaaag    4140
tctacctggc atgggtacca gcacacaaag gaattggagg aaatgaacaa gtagatgggt    4200
tggtcagtgc tggaatcagg aaagtactat ttttagatgg aatagataag gcccaagaag    4260
aacatgagaa atatcacagt aattggagag caatggctag tgattttaac ctaccacctg    4320
tagtagcaaa agaaatagta gccagctgtg ataaatgtca gctaaaaggg gaagccatgc    4380
atggacaagt agactgtagc ccaggaatat ggcagctaga ttgtacacat ttagaaggaa    4440
aagttatctt ggtagcagtt catgtagcca gtggatatat agaagcagaa gtaattccag    4500
cagagacagg gcaagaaaca gcatacttcc tcttaaaatt agcaggaaga tggccagtaa    4560
aaacagtaca tacagacaat ggcagcaatt tcaccagtac tacagttaag gccgcctgtt    4620
ggtgggcggg gatcaagcag gaatttggca ttccctacaa tccccaaagt caaggagtaa    4680
tagaatctat gaataaagaa ttaaagaaaa ttataggaca ggtaagagat caggctgaac    4740
atcttaagac agcagtacaa atggcagtat tcatccacaa ttttaaaaga aaaggggggga   4800
ttggggggta cagtgcaggg gaaagaatag tagacataat agcaacagac atacaaacta    4860
aagaattaca aaaacaaatt acaaaaattc aaaattttcg ggtttattac agggacagca    4920
gagatccagt ttggaaagga ccagcaaagc tcctctggaa aggtgaaggg gcagtagtaa    4980
tacaagataa tagtgacata aaagtagtgc caagaagaaa agcaaagatc atcagggatt    5040
atggaaaaca gatggcaggt gatgattgtg tggcaagtag acaggatgag gattaacaca    5100
tggaaaagat tagtaaaaca ccatatgtat atttcaagga agctaaggga ctggttttat    5160
agacatcact atgaaagtac taatccaaaa ataagttcag aagtacacat cccactaggg    5220
gatgctaaat tagtaataac aacatattgg ggtctgcata caggagaaag agactggcat    5280
ttgggtcagg gagtctccat agaatggagg aaaaagagat atagcacaca agtagaccct    5340
gacctagcag accaactaat tcatctgcac tattttgatt gtttttcaga atctgctata    5400
agaaatacca tattaggacg tatagttagt cctaggtgtg aatatcaagc aggacataac    5460
aaggtaggat ctctacagta cttggcacta gcagcattaa taaaaccaaa acagataaag    5520
ccacctttgc ctagtgttag gaaactgaca gaggacagat ggaacaagcc ccagaagacc    5580
aagggccaca gagggagcca tacaatgaat ggacactaga gcttttagag gaacttaaga    5640
gtgaagctgt tagacatttt cctaggatat ggctccataa cttaggacaa catatctatg    5700
aaacttacgg ggatacttgg gcaggagtgg aagccataat aagaattctg caacaactgc    5760
tgtttatcca tttcagaatt gggtgtcgac atagcagaat aggcgttact cgacagagga    5820
gagcaagaaa tggagccagt agatcctaga ctagagccct ggaagcatcc aggaagtcag    5880
cctaaaactg cttgtaccaa ttgctattgt aaaaagtgtt gctttcattg ccaagtttgt    5940
ttcatgacaa aagccttagg catctcctat ggcaggaaga agcggagaca gcgacgaaga    6000
```

```
gctcatcaga acagtcagac tcatcaagct tctctatcaa agcagtaagt agtacatgta    6060
atgcaaccta taatagtagc aatagtagca ttagtagtag caataataat agcaatagtt    6120
gtgtggtcca tagtaatcat agaatatagg aaaatattaa gacaaagaaa aatagacagg    6180
ttaattgata gactaataga aagagcagaa gacagtggca atgagagtga aggagaagta    6240
tcagcacttg tggagatggg ggtggaaatg gggcaccatg ctccttggga tattgatgat    6300
ctgtagtgct acagaaaaat tgtgggtcac agtctattat ggggtacctg tgtggaagga    6360
agcaaccacc actctatttt gtgcatcaga tgctaaagca tatgatacag aggtacataa    6420
tgtttgggcc acacatgcct gtgtacccac agaccccaac ccacaagaag tagtattggt    6480
aaatgtgaca gaaaatttta acatgtggaa aaatgacatg gtagaacaga tgcatgagga    6540
tataatcagt ttatgggatc aaagcctaaa gccatgtgta aaattaaccc cactctgtgt    6600
tagtttaaag tgcactgatt tgaagaatga tactaatacc aatagtagta gcgggagaat    6660
gataatggag aaaggagaga taaaaaactg ctctttcaat atcagcacaa gcataagaga    6720
taaggtgcag aaagaatatg cattctttta taaacttgat atagtaccaa tagataatac    6780
cagctatagg ttgataagtt gtaacacctc agtcattaca caggcctgtc caaaggtatc    6840
ctttgagcca attcccatac attattgtgc cccggctggt tttgcgattc taaaatgtaa    6900
taataagacg ttcaatggaa caggaccatg tacaaatgtc agcacagtac aatgtacaca    6960
tggaatcagg ccagtagtat caactcaact gctgttaaat ggcagtctag cagaagaaga    7020
tgtagtaatt agatctgcca atttcacaga caatgctaaa accataatag tacagctgaa    7080
cacatctgta gaaattaatt gtacaagacc caacaacaat acaagaaaaa gtatccgtat    7140
ccagagggga ccagggagag catttgttac aataggaaaa ataggaaata tgagacaagc    7200
acattgtaac attagtagag caaaatggaa tgccacttta aaacagatag ctagcaaatt    7260
aagagaacaa tttggaaata ataaaacaat aatctttaag caatcctcag gaggggaccc    7320
agaaattgta acgcacagtt ttaattgtgg aggggaattt ttctactgta attcaacaca    7380
actgtttaat agtacttggt ttaatagtac ttggagtact gaagggtcaa ataacactga    7440
aggaagtgac acaatcacac tcccatgcag aataaaacaa tttataaaca tgtggcagga    7500
agtaggaaaa gcaatgtatg cccctcccat cagtggacaa attagatgtt catcaaatat    7560
tactgggctg ctattaacaa gagatggtgg taataacaac aatgggtccg agatcttcag    7620
acctggagga ggcgatatga gggacaattg gagaagtgaa ttatataaat ataaagtagt    7680
aaaaattgaa ccattaggag tagcacccac caaggcaaag agaagagtgg tgcagagaga    7740
aaaaagagca gtgggaatag gagctttgtt ccttgggttc ttgggagcag caggaagcac    7800
tatgggctgc acgtcaatga cgctgacggt acaggccaga caattattgt ctgatatagt    7860
gcagcagcag aacaatttgc tgagggctat tgaggcgcaa cagcatctgt tgcaactcac    7920 agtctgggc atcaaacagc tccaggcaag aatcctggct gtggaaagat acctaaagga    7980
tcaacagctc ctggggattt ggggttgctc tggaaaactc atttgcacca ctgctgtgcc    8040
ttggaatgct agttggagta taaatctct ggaacagatt tggaataaca tgacctggat    8100
ggagtgggac agagaaatta acaattacac aagcttaata cactccttaa ttgaagaatc    8160
gcaaaaccag caagaaaaga atgaacaaga attattggaa ttagataaat gggcaagttt    8220
gtggaattgg tttaacataa caattggctg gtggtatata aaattattca taatgatagt    8280
aggaggcttg gtaggtttaa gaatagtttt tgctgtactt tctatagtga atagagttag    8340
gcagggatat tcaccattat cgtttcagac ccacctccca atcccgaggg gacccgacag    8400
```

```
gcccgaagga atagaagaag aaggtggaga gagagacaga gacagatcca ttcgattagt    8460
gaacggatcc ttagcactta tctgggacga tctgcggagc ctgtgcctct tcagctacca    8520
ccgcttgaga gacttactct tgattgtaac gaggattgtg gaacttctgg gacgcagggg    8580
gtgggaagcc ctcaaatatt ggtggaatct cctacagtat tggagtcagg aactaaagaa    8640
tagtgctgtt aacttgctca atgccacagc catagcagta gctgagggga cagataggat    8700
tatagaagta ttacaagcag cttatagagc tattcgccac ataccctagaa gaataagaca    8760 gggcttggaa aggattttgc tataagatgg gtggcaagtg gtcaaaaagt agtgtgattg    8820
gatggcctgc tgtaagggaa agaatgagac gagctgagcc agcagcagat ggggtgggag    8880
cagtatctcg agacctagaa aaacatggag caatcacaag tagcaataca gcagctaaca    8940
atgctgcttg tgcctggcta gaagcacaag aggaggaaga ggtgggtttt ccagtcacac    9000
ctcaggtacc tttaagacca atgacttaca aggcagctgt agatcttagc cacttttaa    9060 aagaaaaggg gggactggaa gggctaattc actcccaaag aagacaagat atccttgatc    9120
tgtggatcta ccacacacaa ggctacttcc ctgattggca gaactacaca ccagggccag    9180
gggtcagata tccactgacc tttggatggt gctacaagct agtaccagtt gagccagata    9240
aggtagaaga ggccaataaa ggagagaaca ccagcttgtt acaccctgtg agcctgcatg    9300
gaatggatga ccctgagaga gaagtgttag agtggaggtt tgacagccgc ctagcatttc    9360
atcacgtggc ccgagagctg catccggagt acttcaagaa ctgctgacat cgagcttgct    9420
acaagggact ttccgctggg gactttccag ggaggcgtgg cctgggcggg actggggagt    9480
ggcgagccct cagatgctgc atataagcag ctgcttttttg cctgtactgg gtctctctgg    9540
ttagaccaga tctgagcctg ggagctctct ggctaactag ggaacccact gcttaagcct    9600
caataaagct tgccttgagt gcttcaagta gtgtgtgccc gtctgttgtg tgactctggt    9660
aactagagat ccctcagacc cttttagtca gtgtggaaaa tctctagca              9709
```

<210> SEQ ID NO 16
<211> LENGTH: 500
<212> TYPE: PRT
<213> ORGANISM: Human immunodeficiency virus type 1
<220> FEATURE:
<223> OTHER INFORMATION: gag polyprotein

<400> SEQUENCE: 16

```
Met Gly Ala Arg Ala Ser Val Leu Ser Gly Gly Glu Leu Asp Lys Trp
 1               5                  10                  15

Glu Lys Ile Arg Leu Arg Pro Gly Gly Lys Lys Gln Tyr Lys Leu Lys
             20                  25                  30

His Ile Val Trp Ala Ser Arg Glu Leu Glu Arg Phe Ala Val Asn Pro
         35                  40                  45

Gly Leu Leu Glu Thr Ser Glu Gly Cys Arg Gln Ile Leu Gly Gln Leu
     50                  55                  60

Gln Pro Ser Leu Gln Thr Gly Ser Glu Glu Leu Arg Ser Leu Tyr Asn
 65                  70                  75                  80

Thr Ile Ala Val Leu Tyr Cys Val His Gln Arg Ile Asp Val Lys Asp
                 85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly Asn Asn Ser Gln Val
        115                 120                 125
```

```
Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Pro Ala Thr Ile Met Ile Gln Lys Gly Asn Phe Arg
370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Glu Glu Ser Phe Arg
450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500

<210> SEQ ID NO 17
<211> LENGTH: 1003
<212> TYPE: PRT
<213> ORGANISM: Human immunodeficiency virus type 1
<220> FEATURE:
<223> OTHER INFORMATION: pol polyprotein
```

-continued

<400> SEQUENCE: 17

```
Phe Phe Arg Glu Asp Leu Ala Phe Pro Gln Gly Lys Ala Arg Glu Phe
 1               5                  10                  15

Ser Ser Glu Gln Thr Arg Ala Asn Ser Pro Thr Arg Arg Glu Leu Gln
             20                  25                  30

Val Trp Gly Arg Asp Asn Asn Ser Leu Ser Glu Ala Gly Ala Asp Arg
         35                  40                  45

Gln Gly Thr Val Ser Phe Ser Phe Pro Gln Ile Thr Leu Trp Gln Arg
     50                  55                  60

Pro Leu Val Thr Ile Lys Ile Gly Gly Gln Leu Lys Glu Ala Leu Leu
 65                  70                  75                  80

Asp Thr Gly Ala Asp Asp Thr Val Leu Glu Glu Met Asn Leu Pro Gly
                 85                  90                  95

Arg Trp Lys Pro Lys Met Ile Gly Gly Ile Gly Gly Phe Ile Lys Val
             100                 105                 110

Gly Gln Tyr Asp Gln Ile Leu Ile Glu Ile Cys Gly His Lys Ala Ile
         115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
    210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Gln Lys Lys Ser Val Thr Val Leu Asp Val Gly Asp Ala Tyr Phe Ser
            260                 265                 270

Val Pro Leu Asp Lys Asp Phe Arg Lys Tyr Thr Ala Phe Thr Ile Pro
        275                 280                 285

Ser Ile Asn Asn Glu Thr Pro Gly Ile Arg Tyr Gln Tyr Asn Val Leu
    290                 295                 300

Pro Gln Gly Trp Lys Gly Ser Pro Ala Ile Phe Gln Cys Ser Met Thr
305                 310                 315                 320

Lys Ile Leu Glu Pro Phe Arg Lys Gln Asn Pro Asp Ile Val Ile Tyr
                325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
        355                 360                 365

Phe Thr Thr Pro Asp Lys Lys His Gln Lys Glu Pro Pro Phe Leu Trp
    370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
```

```
                    405                 410                 415
Gly Lys Leu Asn Trp Ala Ser Gln Ile Tyr Ala Gly Ile Lys Val Arg
                420                 425                 430
Gln Leu Cys Lys Leu Leu Arg Gly Thr Lys Ala Leu Thr Glu Val Val
            435                 440                 445
Pro Leu Thr Glu Glu Ala Glu Leu Glu Leu Ala Glu Asn Arg Glu Ile
        450                 455                 460
Leu Lys Glu Pro Val His Gly Val Tyr Tyr Asp Pro Ser Lys Asp Leu
465                 470                 475                 480
Ile Ala Glu Ile Gln Lys Gln Gly Gln Gly Gln Trp Thr Tyr Gln Ile
                485                 490                 495
Tyr Gln Glu Pro Phe Lys Asn Leu Lys Thr Gly Lys Tyr Ala Arg Met
            500                 505                 510
Lys Gly Ala His Thr Asn Asp Val Lys Gln Leu Thr Glu Ala Val Gln
        515                 520                 525
Lys Ile Ala Thr Glu Ser Ile Val Ile Trp Gly Lys Thr Pro Lys Phe
    530                 535                 540
Lys Leu Pro Ile Gln Lys Glu Thr Trp Glu Ala Trp Trp Thr Glu Tyr
545                 550                 555                 560
Trp Gln Ala Thr Trp Ile Pro Glu Trp Glu Phe Val Asn Thr Pro Pro
                565                 570                 575
Leu Val Lys Leu Trp Tyr Gln Leu Glu Lys Glu Pro Ile Ile Gly Ala
            580                 585                 590
Glu Thr Phe Tyr Val Asp Gly Ala Ala Asn Arg Glu Thr Lys Leu Gly
        595                 600                 605
Lys Ala Gly Tyr Val Thr Asp Arg Gly Arg Gln Lys Val Val Pro Leu
    610                 615                 620
Thr Asp Thr Thr Asn Gln Lys Thr Glu Leu Gln Ala Ile His Leu Ala
625                 630                 635                 640
Leu Gln Asp Ser Gly Leu Glu Val Asn Ile Val Thr Asp Ser Gln Tyr
                645                 650                 655
Ala Leu Gly Ile Ile Gln Ala Gln Pro Asp Lys Ser Glu Ser Glu Leu
            660                 665                 670
Val Ser Gln Ile Ile Glu Gln Leu Ile Lys Lys Glu Lys Val Tyr Leu
        675                 680                 685
Ala Trp Val Pro Ala His Lys Gly Ile Gly Gly Asn Glu Gln Val Asp
    690                 695                 700
Gly Leu Val Ser Ala Gly Ile Arg Lys Val Leu Phe Leu Asp Gly Ile
705                 710                 715                 720
Asp Lys Ala Gln Glu Glu His Glu Lys Tyr His Ser Asn Trp Arg Ala
                725                 730                 735
Met Ala Ser Asp Phe Asn Leu Pro Pro Val Val Ala Lys Glu Ile Val
            740                 745                 750
Ala Ser Cys Asp Lys Cys Gln Leu Lys Gly Glu Ala Met His Gly Gln
        755                 760                 765
Val Asp Cys Ser Pro Gly Ile Trp Gln Leu Asp Cys Thr His Leu Glu
    770                 775                 780
Gly Lys Val Ile Leu Val Ala Val His Val Ala Ser Gly Tyr Ile Glu
785                 790                 795                 800
Ala Glu Val Ile Pro Ala Glu Thr Gly Gln Glu Thr Ala Tyr Phe Leu
                805                 810                 815
Leu Lys Leu Ala Gly Arg Trp Pro Val Lys Thr Val His Thr Asp Asn
            820                 825                 830
```

-continued

```
Gly Ser Asn Phe Thr Ser Thr Thr Val Lys Ala Ala Cys Trp Trp Ala
            835                 840                 845
Gly Ile Lys Gln Glu Phe Gly Ile Pro Tyr Asn Pro Gln Ser Gln Gly
    850                 855                 860
Val Ile Glu Ser Met Asn Lys Glu Leu Lys Lys Ile Ile Gly Gln Val
865                 870                 875                 880
Arg Asp Gln Ala Glu His Leu Lys Thr Ala Val Gln Met Ala Val Phe
                885                 890                 895
Ile His Asn Phe Lys Arg Lys Gly Gly Ile Gly Gly Tyr Ser Ala Gly
            900                 905                 910
Glu Arg Ile Val Asp Ile Ile Ala Thr Asp Ile Gln Thr Lys Glu Leu
            915                 920                 925
Gln Lys Gln Ile Thr Lys Ile Gln Asn Phe Arg Val Tyr Tyr Arg Asp
    930                 935                 940
Ser Arg Asp Pro Val Trp Lys Gly Pro Ala Lys Leu Leu Trp Lys Gly
945                 950                 955                 960
Glu Gly Ala Val Val Ile Gln Asp Asn Ser Asp Ile Lys Val Val Pro
                965                 970                 975
Arg Arg Lys Ala Lys Ile Ile Arg Asp Tyr Gly Lys Gln Met Ala Gly
            980                 985                 990
Asp Asp Cys Val Ala Ser Arg Gln Asp Glu Asp
            995                 1000

<210> SEQ ID NO 18
<211> LENGTH: 192
<212> TYPE: PRT
<213> ORGANISM: Human immunodeficiency virus type 1
<220> FEATURE:
<223> OTHER INFORMATION: vif protein

<400> SEQUENCE: 18

Met Glu Asn Arg Trp Gln Val Met Ile Val Trp Gln Val Asp Arg Met
  1               5                  10                  15
Arg Ile Asn Thr Trp Lys Arg Leu Val Lys His His Met Tyr Ile Ser
            20                  25                  30
Arg Lys Ala Lys Asp Trp Phe Tyr Arg His His Tyr Glu Ser Thr Asn
        35                  40                  45
Pro Lys Ile Ser Ser Glu Val His Ile Pro Leu Gly Asp Ala Lys Leu
    50                  55                  60
Val Ile Thr Thr Tyr Trp Gly Leu His Thr Gly Glu Arg Asp Trp His
65                  70                  75                  80
Leu Gly Gln Gly Val Ser Ile Glu Trp Arg Lys Lys Arg Tyr Ser Thr
                85                  90                  95
Gln Val Asp Pro Asp Leu Ala Asp Gln Leu Ile His Leu His Tyr Phe
            100                 105                 110
Asp Cys Phe Ser Glu Ser Ala Ile Arg Asn Thr Ile Leu Gly Arg Ile
        115                 120                 125
Val Ser Pro Arg Cys Glu Tyr Gln Ala Gly His Asn Lys Val Gly Ser
    130                 135                 140
Leu Gln Tyr Leu Ala Leu Ala Ala Leu Ile Lys Pro Lys Gln Ile Lys
145                 150                 155                 160
Pro Pro Leu Pro Ser Val Arg Lys Leu Thr Glu Asp Arg Trp Asn Lys
                165                 170                 175
Pro Gln Lys Thr Lys Gly His Arg Gly Ser His Thr Met Asn Gly His
            180                 185                 190
```

```
<210> SEQ ID NO 19
<211> LENGTH: 96
<212> TYPE: PRT
<213> ORGANISM: Human immunodeficiency virus type 1
<220> FEATURE:
<223> OTHER INFORMATION: vpr protein

<400> SEQUENCE: 19

Met Glu Gln Ala Pro Glu Asp Gln Gly Pro Gln Arg Glu Pro Tyr Asn
 1               5                  10                  15

Glu Trp Thr Leu Glu Leu Leu Glu Glu Leu Lys Ser Glu Ala Val Arg
                20                  25                  30

His Phe Pro Arg Ile Trp Leu His Asn Leu Gly Gln His Ile Tyr Glu
            35                  40                  45

Thr Tyr Gly Asp Thr Trp Ala Gly Val Glu Ala Ile Ile Arg Ile Leu
        50                  55                  60

Gln Gln Leu Leu Phe Ile His Phe Arg Ile Gly Cys Arg His Ser Arg
 65                  70                  75                  80

Ile Gly Val Thr Arg Gln Arg Arg Ala Arg Asn Gly Ala Ser Arg Ser
                85                  90                  95

<210> SEQ ID NO 20
<211> LENGTH: 86
<212> TYPE: PRT
<213> ORGANISM: Human immunodeficiency virus type 1
<220> FEATURE:
<223> OTHER INFORMATION: tat protein

<400> SEQUENCE: 20

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
                20                  25                  30

His Cys Gln Val Cys Phe Met Thr Lys Ala Leu Gly Ile Ser Tyr Gly
            35                  40                  45

Arg Lys Lys Arg Arg Gln Arg Arg Ala His Gln Asn Ser Gln Thr
        50                  55                  60

His Gln Ala Ser Leu Ser Lys Gln Pro Thr Ser Gln Ser Arg Gly Asp
 65                  70                  75                  80

Pro Thr Gly Pro Lys Glu
                85

<210> SEQ ID NO 21
<211> LENGTH: 116
<212> TYPE: PRT
<213> ORGANISM: Human immunodeficiency virus type 1
<220> FEATURE:
<223> OTHER INFORMATION: rev protein

<400> SEQUENCE: 21

Met Ala Gly Arg Ser Gly Asp Ser Asp Glu Glu Leu Ile Arg Thr Val
 1               5                  10                  15

Arg Leu Ile Lys Leu Leu Tyr Gln Ser Asn Pro Pro Asn Pro Glu
                20                  25                  30

Gly Thr Arg Gln Ala Arg Arg Asn Arg Arg Arg Trp Arg Glu Arg
            35                  40                  45

Gln Arg Gln Ile His Ser Ile Ser Glu Arg Ile Leu Ser Thr Tyr Leu
        50                  55                  60
```

-continued

Gly Arg Ser Ala Glu Pro Val Pro Leu Gln Leu Pro Pro Leu Glu Arg
65                  70                  75                  80

Leu Thr Leu Asp Cys Asn Glu Asp Cys Gly Thr Ser Gly Thr Gln Gly
                85                  90                  95

Val Gly Ser Pro Gln Ile Leu Val Glu Ser Pro Thr Val Leu Glu Ser
            100                 105                 110

Gly Thr Lys Glu
        115

<210> SEQ ID NO 22
<211> LENGTH: 81
<212> TYPE: PRT
<213> ORGANISM: Human immunodeficiency virus type 1
<220> FEATURE:
<223> OTHER INFORMATION: vpu protein

<400> SEQUENCE: 22

Met Gln Pro Ile Ile Val Ala Ile Val Ala Leu Val Val Ala Ile Ile
1               5                   10                  15

Ile Ala Ile Val Val Trp Ser Ile Val Ile Ile Glu Tyr Arg Lys Ile
            20                  25                  30

Leu Arg Gln Arg Lys Ile Asp Arg Leu Ile Asp Arg Leu Ile Glu Arg
        35                  40                  45

Ala Glu Asp Ser Gly Asn Glu Ser Glu Gly Glu Val Ser Ala Leu Val
    50                  55                  60

Glu Met Gly Val Glu Met Gly His His Ala Pro Trp Asp Ile Asp Asp
65                  70                  75                  80

Leu

<210> SEQ ID NO 23
<211> LENGTH: 854
<212> TYPE: PRT
<213> ORGANISM: Human immunodeficiency virus type 1
<220> FEATURE:
<223> OTHER INFORMATION: envelope polyprotein

<400> SEQUENCE: 23

Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

-continued

```
Ile Ser Thr Ser Ile Arg Asp Lys Val Gln Lys Glu Tyr Ala Phe Phe
            165                 170                 175

Tyr Lys Leu Asp Ile Val Pro Ile Asp Asn Thr Ser Tyr Arg Leu Ile
            180                 185                 190

Ser Cys Asn Thr Ser Val Ile Thr Gln Ala Cys Pro Lys Val Ser Phe
            195                 200                 205

Glu Pro Ile Pro Ile His Tyr Cys Ala Pro Ala Gly Phe Ala Ile Leu
    210                 215                 220

Lys Cys Asn Asn Lys Thr Phe Asn Gly Thr Gly Pro Cys Thr Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Asp Val Val Ile Arg Ser
            260                 265                 270

Ala Asn Phe Thr Asp Asn Ala Lys Thr Ile Ile Val Gln Leu Asn Thr
            275                 280                 285

Ser Val Glu Ile Asn Cys Thr Arg Pro Asn Asn Asn Thr Arg Lys Ser
    290                 295                 300

Ile Arg Ile Gln Arg Gly Pro Gly Arg Ala Phe Val Thr Ile Gly Lys
305                 310                 315                 320

Ile Gly Asn Met Arg Gln Ala His Cys Asn Ile Ser Arg Ala Lys Trp
                325                 330                 335

Asn Ala Thr Leu Lys Gln Ile Ala Ser Lys Leu Arg Glu Gln Phe Gly
            340                 345                 350

Asn Asn Lys Thr Ile Ile Phe Lys Gln Ser Ser Gly Gly Asp Pro Glu
            355                 360                 365

Ile Val Thr His Ser Phe Asn Cys Gly Gly Glu Phe Phe Tyr Cys Asn
    370                 375                 380

Ser Thr Gln Leu Phe Asn Ser Thr Trp Phe Asn Ser Thr Trp Ser Thr
385                 390                 395                 400

Glu Gly Ser Asn Asn Thr Glu Gly Ser Asp Thr Ile Thr Leu Pro Cys
                405                 410                 415

Arg Ile Lys Gln Phe Ile Asn Met Trp Gln Glu Val Gly Lys Ala Met
            420                 425                 430

Tyr Ala Pro Pro Ile Ser Gly Gln Ile Arg Cys Ser Ser Asn Ile Thr
            435                 440                 445

Gly Leu Leu Leu Thr Arg Asp Gly Gly Asn Asn Asn Asn Gly Ser Glu
    450                 455                 460

Ile Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Arg Arg Val Val Gln Arg Glu Lys Arg Ala Val Gly
            500                 505                 510

Ile Gly Ala Leu Phe Leu Gly Phe Leu Gly Ala Ala Gly Ser Thr Met
            515                 520                 525

Gly Cys Thr Ser Met Thr Leu Thr Val Gln Ala Arg Gln Leu Leu Ser
530                 535                 540

Asp Ile Val Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
                565                 570                 575

Arg Ile Leu Ala Val Glu Arg Tyr Leu Lys Asp Gln Gln Leu Leu Gly
```

```
                       580                 585                 590
Ile Trp Gly Cys Ser Gly Lys Leu Ile Cys Thr Thr Ala Val Pro Trp
            595                 600                 605

Asn Ala Ser Trp Ser Asn Lys Ser Leu Glu Gln Ile Trp Asn Asn Met
            610                 615                 620

Thr Trp Met Glu Trp Asp Arg Glu Ile Asn Asn Tyr Thr Ser Leu Ile
625                 630                 635                 640

His Ser Leu Ile Glu Glu Ser Gln Asn Gln Gln Glu Lys Asn Glu Gln
                645                 650                 655

Glu Leu Leu Glu Leu Asp Lys Trp Ala Ser Leu Trp Asn Trp Phe Asn
            660                 665                 670

Ile Thr Asn Trp Leu Trp Tyr Ile Lys Leu Phe Ile Met Ile Val Gly
            675                 680                 685

Gly Leu Val Gly Leu Arg Ile Val Phe Ala Val Leu Ser Ile Val Asn
            690                 695                 700

Arg Val Arg Gln Gly Tyr Ser Pro Leu Ser Phe Gln Thr His Leu Pro
705                 710                 715                 720

Ile Pro Arg Gly Pro Asp Arg Pro Glu Gly Ile Glu Glu Glu Gly Gly
                725                 730                 735

Glu Arg Asp Arg Asp Arg Ser Ile Arg Leu Val Asn Gly Ser Leu Ala
            740                 745                 750

Leu Ile Trp Asp Asp Leu Arg Ser Leu Cys Leu Phe Ser Tyr His Arg
            755                 760                 765

Leu Arg Asp Leu Leu Leu Ile Val Thr Arg Ile Val Glu Leu Leu Gly
            770                 775                 780

Arg Arg Gly Trp Glu Ala Leu Lys Tyr Trp Trp Asn Leu Leu Gln Tyr
785                 790                 795                 800

Trp Ser Gln Glu Leu Lys Asn Ser Ala Val Asn Leu Leu Asn Ala Thr
                805                 810                 815

Ala Ile Ala Val Ala Glu Gly Thr Asp Arg Val Ile Glu Val Leu Gln
            820                 825                 830

Ala Ala Tyr Arg Ala Ile Arg His Ile Pro Arg Arg Ile Arg Gln Gly
            835                 840                 845

Leu Glu Arg Ile Leu Leu
    850

<210> SEQ ID NO 24
<211> LENGTH: 206
<212> TYPE: PRT
<213> ORGANISM: Human immunodeficiency virus type 1
<220> FEATURE:
<223> OTHER INFORMATION: nef protein

<400> SEQUENCE: 24

Met Gly Gly Lys Trp Ser Lys Ser Ser Val Ile Gly Trp Pro Ala Val
 1               5                  10                  15

Arg Glu Arg Met Arg Arg Ala Glu Pro Ala Ala Asp Gly Val Gly Ala
                20                  25                  30

Val Ser Arg Asp Leu Glu Lys His Gly Ala Ile Thr Ser Ser Asn Thr
            35                  40                  45

Ala Ala Asn Asn Ala Ala Cys Ala Trp Leu Glu Ala Gln Glu Glu Glu
        50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
```

-continued

```
                    85                      90                      95
Leu Glu Gly Leu Ile His Ser Gln Arg Arg Gln Asp Ile Leu Asp Leu
            100                     105                 110
Trp Ile Tyr His Thr Gln Gly Tyr Phe Pro Asp Trp Gln Asn Tyr Thr
        115                     120                 125
Pro Gly Pro Gly Val Arg Tyr Pro Leu Thr Phe Gly Trp Cys Tyr Lys
    130                     135                 140
Leu Val Pro Val Glu Pro Asp Lys Val Glu Glu Ala Asn Lys Gly Glu
145                     150                 155                 160
Asn Thr Ser Leu Leu His Pro Val Ser Leu His Gly Met Asp Asp Pro
                165                 170                 175
Glu Arg Glu Val Leu Glu Trp Arg Phe Asp Ser Arg Leu Ala Phe His
            180                     185                 190
His Val Ala Arg Glu Leu His Pro Glu Tyr Phe Lys Asn Cys
        195                     200                 205
```

RETROVIRAL HYBRID VECTORS PSEUDOTYPED WITH LCMV

The present invention relates in general to the pseudotyping of retroviruses with lymphocytic choriomeningitis virus. In particular, the invention relates to pseudotyping in MLV packaging cells which are optionally env-deleted, or in packaging cells derived from lentiviruses. Preferably, pseudotyping is carried out by infection with LCMV or a preferably env-deleted mutant, or by transfection with an expression plasmid containing the gp-gene of LCMV or a part thereof and optionally, in addition, the np-, the 1- and/or the z-gene of LCMV. The invention also relates to the use of such pseudotypes for the infection of cells, particularly the use in gene therapy.

Retroviral vectors are increasingly being used in the state of the art, for example, for gene transfer in genetic engineering and medical research or in gene therapy approaches (cf. e.g. C. Baum et al. in *Seminars in Oncology: Gene Therapy of Cancer: Translational approaches from preclinical studies to clinical implementations.*, eds. Gerson & Lattime, Academic Press, 1998). The retroviral vectors are mostly derived from murine leukaemia viruses (MLV) and contain all the sequences of the LTR regions required for integration and the ψ-element responsible for packaging. The regions coding for the virus proteins are replaced by foreign genes and the control sequences thereof which it would be desirable to introduce into human cells. The vectors are expressed in so-called helper cell lines (packaging cell lines) which contain a copy of a complete retrovirus genome. It synthesises all the proteins required for replication and infection, but is unable to package its genomic virus-RNA into particles because it has a defect in the ψ-sequences. If the retroviral vectors are inserted into these helper cells and transcribed, the transgenic mRNA formed is able, by means of the ψ-region which is characteristic of it, to interact with the structure proteins of the helper virus and be packaged to particles. The recombinant virions, which possess no genetic information at all for virus components, adsorb on cells by way of their surface proteins, the capsids are taken up in the cytoplasm, and the transgenic RNA is converted to double-stranded DNA and integrated into the host cell genome. The advantage of this system is the stable integration of the foreign genes which are passed on to the daughter cells on division. The non-specific integration at arbitrary sites of the cell genome, which is characteristic of retroviruses, is a disadvantage.

Retroviral vectors impart a stable colinear integration (i.e. without recombinations and rearrangement of the coding sequences in the vector genome) and thereby a long-term expression of the transgene. Long-term gene expression has otherwise been possible hitherto only by means of the episomal herpes virus vectors or the adeno-associated virus vectors (AAV vectors). The packaging systems (packaging cell lines) have not yet, however, been optimised for the latter vector systems. Moreover, AAV vectors have a lower packaging capacity (about 5 kb for AAV compared with about 10–12 kb for retroviral vectors).

In addition to the gene to be transferred, the transgene, packaging lines also express the vector genome which contains retroviral cis elements. The genomic vector transcript does not, therefore, code for retroviral proteins but is inserted in the packaging lines with the aid of the gag-, pol- and env-gene products into a virion which is infectious but not capable of replication. This virion may then be used as a retroviral vector for transferring the transgene integrated into the vector genome into the desired target cells without further proliferation of the vector occurring there. In other words, the viral vector is only able to infect the target cells but is unable to proliferate any further therein.

The development of retroviral packaging systems is already well advanced and vector supernatants that are free from viruses capable of replication can be produced in large quantities under GMP conditions (Good Manufacturing Practice; Directive of the Commission for laying down principles and guidelines of good manufacturing practice (GMP) for certain medicaments for use in humans (91/356/EEC) of 13.6.91). Vectors based on murine leukaemia virus (MLV vectors) have already been used repeatedly in clinical trials (P. Chu et al., J. Mol. Med. 76 (1998) 184–192).

Two fundamental types of retroviral packaging systems are known in the prior art (J. M. Wilson, Clin. Exp. Immunol. 107 Suppl. 1 (1997) 31–32; C. Baum et al. 1998), loc cit.).

MLV packaging cell lines contain the retroviral genes gag, pol and env (FIG. 1) and the sequences required for packaging the retroviral RNA are deleted (C. Baum et al., (1998), loc. cit.).

The second type of known packaging systems is derived from the lentiviruses (R. Carroll et al., J. Virol. 68 (1994) 6047–6051; P. Corbeau et al., Proc. Natl. Acad. Sci. USA 93 (1996) 14070–14075; L. Naldini et al., Science 272 (1996) 263–267; C. Parolin et al., J. Virol. 68 (1994) 3888–3895; J. Reiser et al., Proc. Natl. Acad. Sci. USA 93 (1996) 15266–15271; J. H. Richardson et al., J. Gen. Virol. 76 (1995) 691–696; T. Shimada et al., J. Clin. Invest. 88 (1991) 1043–1047). Lentiviruses are complex retroviruses which, in addition to the gag, pol and env gene products also express a series of regulatory genes. Examples of lentiviruses from which packaging systems were derived are the human immunodeficiency virus (HIV), the "simian immunodeficiency virus" (SIV) and the "feline immunodeficiency virus" (FIV). The structure of the lentiviral packaging systems is similar, in principle, to that of the MLV vectors.

An advantage of lentiviral vectors is that they are also able to infect resting cells. In the case of MLV vectors, on the other hand, the vector genome can be transported into the cell nucleus only during cell division, i.e. when the nuclear membrane is dissolved. However, in view of the complex structure of the lentiviral genome, packaging systems derived from lentiviruses have disadvantages which are manifested in a comparatively low titre and relatively poor stability. Due to the complex genome structure, cis and trans elements in the genome cannot be separated clearly from one another. In the packaging constructs that express lentiviral gag, pol and env genes there are also to be found, therefore, important cis-regulatory sequences (e.g. parts of the packaging signal) which must also be contained in the vector genome. Due to these homologies, recombinations between vector genome and the packaging constructs may occur and thus the release of retroviruses capable of replication (e.g. an HIV wild virus which would be highly undesirable), so these systems are not comparable with MLV packaging lines.

All the vector systems known hitherto in the prior art also have some crucial shortcomings which prevent successful use in gene therapy: 1. Retroviral vectors are mostly produced only in inadequate titres and cannot be concentrated any further due to the instability of their envelope proteins. 2. Vector particles cannot be purified without loss of infectiousness due to the instability of their envelope proteins. Such purification is essential, however, as the cell culture supernatants from which vectors are harvested are contaminated by cellular constituents. 3. Due to their envelope proteins, retroviral vectors are inactivated by human serum complement. 4. The receptor for the envelope protein of the classic amphotrophic vectors is expressed on virtually all the cell lines considered. However, many primary human cells such as hepatocytes and haematopoietic stem cells which are attractive targets of gene therapy are deficient in functional amphotrophic receptors, as a result of which transduction is rendered difficult or prevented.

The object of the present invention is, therefore, to provide retroviral packaging systems which do not have the disadvantages of the packaging cell lines known in the prior art.

In particular, the object of the present invention is to provide packaging systems which permit a stable retroviral transfer of transgenes into the target cells, i.e. which lead to stable integration of the transgene into the genome of the target or host cells followed by stable expression of this gene.

The object according to the invention is achieved in that retroviruses are pseudotyped with lymphocytic choriomeningitis virus (LCMV).

The present invention relates, therefore, to a recombinant virion which is preferably transfected with one or more foreign genes, which may be obtained by pseudotyping the virus particle with lymphocytic choriomeningitis virus (LCMV).

The tropism and also the stability of a virus is determined primarily by the envelope protein. Murine retroviruses are able to incorporate not only the MLV-env coded glycoproteins but also envelope proteins of other types of virus into their virus coat. As a result, so-called pseudotypes are produced. Retroviral pseudotype vectors are produced by expression of foreign viral envelope proteins in MLV packaging lines. Conventional MLV packaging cell lines contain the retroviral genes gag, pol and env. Sequences which are necessary for the packaging of retroviral genomic RNA were deleted. A vector is introduced into such packaging lines which contains not only the gene which is to be transferred but also the retroviral packaging sequence and other retroviral cis elements (LTR, leader). The retroviral RNA genome is inserted with the aid of the gag, pol and env gene products into a virion which is infectious but not capable of replication. This virion can then be used as a retroviral vector for the transduction of cells. Pseudotype packaging lines also contain the envelope protein gene of a foreign virus. The pseudotype packaging lines according to the invention contain the envelope protein gene of LCMV, and expression of the LCMV glycoproteins takes place.

The present invention provides for the first time vector systems which may be produced in high titres and concentrated. The vector particles according to the invention can also be purified without or without any substantial loss of infectiousness. Surprisingly, it has become apparent within the scope of the present invention that the pseudotyping according to the invention is not cytotoxic for the packaging cells. Stable packaging cell lines (packaging systems) are thus provided for the first time which permit a stable retroviral transfer of transgenes into the target cells, i.e. which lead to a stable integration of the transgene into the genome of the target or host cells followed by stable expression of this gene.

The cell lines according to the invention are also characterised by a broad, trans-species host cell spectrum (cell tropism). A crucial advantage of the present invention is the fact that individual mutations in the envelope protein of LCMV can lead to a modification of the tropism of LCMV. That is, due to individual point mutations in gp, viruses that are more likely to infect nerve cells become viruses that are more likely to infect lymphocytes or those that are more likely to infect monocytes.

Within the scope of the present invention, LCMV is used for pseudotyping. It is possible or it may even be preferable to use other strains of LCMV instead of the LCMV wild-type. Slight variations in the gp nucleic acid sequence or in the amino acid sequence of the expressed envelope protein in various strains of LCMV may thus alter substantially the cell tropism (host cell spectrum) of LCMV (M. Matloubian et al., J. Virol. 67 (1993) 7340–7349; M. N. Teng, J. Virol. 70 (1996) 8438–8443; King et al., J. Virol 64; 1990, 5611–5616). No such tropism variants in the glycoprotein are found for any of the other retroviral vector systems known hitherto, and a more targeted transduction of the desired cell type is made possible for the first time according to the invention. According to a preferred embodiment of the invention, it may therefore be advantageous to provide packaging systems with various glycoprotein variants (GP variants) for different applications.

Within the scope of the present invention, the starting material is the gp genes of the neurotropic LCMV strain Armstrong, L(ARM) (L. Villarete et al., J. Virol. 68 (1994) 7490–7496) (region coding for SEQ ID NO: 4; compare appendix to the sequence protocol, re SEQ ID NO: 3), and of the haematotropic strain WE (V. Romanowski et al., Virus Res. 3, (1985) 101–114) (SEQ ID NO: 1). Also included according to the invention are variants (tropism variants) of these two strains in which individual amino acids are exchanged in the gp gene product, since the tropism of the virus can thereby be altered.

It is rather probable that "cryptic splice regions" are located in the RNA sequence, since LCMV is an RNA virus without a nuclear phase during the propagation cycle. The removal of such regions (correction for aberrant splicing) can be utilised to achieve an improved expression. Such "splice-corrected" variants are also, therefore, included according to the invention.

Pseudotyping can be improved by such optimisation of GP expression, whereby it is possible to dispense with an additional support by means of at least one further LCMV protein. Generally speaking, expression vectors which permit a high, stable gene expression in eukaryotic cells are suitable for the expression of LCMV. The choice of expression vector is, however, crucial for the packaging of the retroviral LCMV pseudotypes only insofar as it must guarantee a high and stable level of expression, i.e. a level of expression which is high enough to permit the formation of pseudotypes and which is durable (stable) without switching off of the promoter occurring.

The following two expression cassettes are particularly preferred according to the invention:
(CMV promoter)—(β-globin-intron-2)—(gp)—(SV40 poly A-signal) and
(EF-1alpha promoter)—(gp)—(poly-A signal of the G-CSF gene)
(S. Mizushima, Nucleic Acids Res. 18 (1990) 5322, T. Uetsuki, J. Biol. Chem. 264 (1989) 5791–5798).

The sequences for the constituents of the expression cassettes are shown in the sequence protocol or are generally well known:
cytomegalovirus promoter (CMV promoter):
  (M. Boshart et al., Cell 41 (1958) 521–530; F.
  Langle-Rouault et al., Virol. 72 (7) 6181–5 (1998))
betaglobin-intron-2:
  (Jeffreys, A. J. et al., Cell 12 (1977) 1097–1108)

SV40 poly A signal:
(M. Boshart et al., Cell 41 (1958) 521–530; F.
Langle-Rouault et al., Virol. 72 (7) 6181–5 (1998))
EF-1alpha promoter: SEQ ID NO: 9
(S. Mizushima, Nucleic Acids Res. 18 (1990) 5322, T.
Uetsuki, J. Biol. Chem. 264 (1989) 5791–5798).
G-CSF poly A signal:
(S. Mizushima, Nucleic Acids Res. 18 (1990) 5322, T.
Uetsuki, J. Biol. Chem. 264 (1989) 5791–5798).
gp (LCMV): compare SEQ ID NO: 1, 3, region coding for SEQ ID NO: 4 (see also Appendix to the sequence listing).

Within the scope of the present invention, the above-mentioned expression cassettes are also therefore included, changes in the relevant nucleic acid sequences being possible as long as the functionality of the expression cassettes remains intact, i.e. their use according to the invention permits pseudotyping of the packaging cells and also does not prevent the transfection of the target cells and the stable integration of the transgenes into the host genome.

Moreover, an episomal EBV expression vector (Epstein-Barr-Virus; cf. F. Langle-Rouault et al., Virol. 72 (7) 6181–5 (1998)) (pCep4) from Invitrogen also exhibits high expression and is therefore preferred within the scope of the present invention.

The present invention also provides, therefore, a packaging cell which contains the retroviral genes gag (region coding for SEQ ID NO: 12; cf. Appendix to the sequence listing, re SEQ ID NO: 11), pol (region coding for SEQ ID NO: 13; cf. Appendix to the sequence listing, re SEQ ID NO: 11) and optionally the retroviral gene env (region coding for SEQ ID NO: 14; cf. Appendix to the sequence listing, re SEQ ID NO: 11) and/or regulatory retroviral genes (in the case of lentiviral packaging systems, see below, e.g. the gene coding for the lentiviral Rev protein which prevents splicing of the retroviral genomic RNA) and also contains the gene gp coding for the glycoproteins GP-1 and GP-2 of LCMV (region coding for SEQ ID NO: 4; cf. Appendix to the sequence listing, re SEQ ID NO: 3) or a part thereof. Also included are nucleic acid sequences which exhibit modifications or deviations (mutations, deletions etc.) in the sequences as long as, when used according to the invention, the pseudotyping of the packaging cells is guaranteed and the transfection of the target cells and the stable integration of the transgenes into the host genome is not impeded. This includes fragments of the named sequences. These derivatives should always be included hereinafter when any gene as such is mentioned.

Within the scope of the present invention, "GP" or "GP protein" denotes the GP-C precursor protein from which GP-1 and GP-2 are then produced by proteolytic cleavage, these being denoted hereinafter simply "LCMV glycoprotein".

According to the invention, moreover, pseudotype packaging systems are provided in which, apart from the gp gene product (SEQ ID NO: 4), one or more other genes of LCMV are expressed such as, for example, the gene np coding for the nucleoprotein (region coding for SEQ ID NO: 5; cf. Appendix to the sequence listing, re SEQ ID NO: 3), the gene z coding for a protein with an unknown function (region coding for SEQ ID NO: 8; cf. Appendix to the sequence listing, re SEQ ID NO: 6) and the gene 1 coding for RNA polymerase (region coding for SEQ ID NO: 7; cf. Appendix to the sequence listing, re SEQ ID NO: 6). According to a particular embodiment of the invention, these genes may stem either from the WE or Armstrong strain of LCMV. In this connection, either the complete sequences of the genes np, z and/or 1 (SEQ ID NOs: see above) or parts thereof may be used. Sequences included according to the invention are nucleic acid sequences which exhibit modifications or deviations (mutations, deletions etc.) in the sequences (derivatives), as long as pseudotyping of the packaging cells is guaranteed and the transfection of the target cells and the stable integration of the transgenes into the host genome is not impeded. This includes fragments of the named sequences. These derivatives should always be included hereinafter when any gene as such is mentioned.

The invention also provides, therefore, a packaging cell which, in addition to the gp gene of LCMV, contains at least one gene from the group comprising the gene np coding for the nucleoprotein, the gene 1 coding for RNA polymerase and the gene z of LCMV coding for a protein of unknown function.

The MLV/LCMV pseudotypes, i.e. recombinant retroviral virions which contain the LCMV glycoprotein incorporated in their coat, are produced by the packaging cells according to the invention.

For the production of the recombinant virions, the starting materials for the viral packaging cell lines within the scope of the present invention are preferably all the cell lines that produce high titres of retroviral vectors. Cell lines used in preference are NIH3T3, Te671, 293T, HT1080 (F. L. Cosset et al., J. Virol. 69 (1995) 7430–7436; D. Markowitz et al., Virology 167 (1988) 400–406); W. S. Pear et al., PNAS 90 (1993) 8392–8396). The choice of cell line is not important, however, for the specific advantages of the invention because it has become apparent that GP does not have a toxic effect in any cell line examined hitherto. If, therefore, lines should be found in the future which permit a more efficient vector production (i.e. more stable titre which is at least as high as in the above-mentioned lines, >$10^6$/ml), these may also be used.

The gag and pol genes of the Moloney strain of murine leukaemia viruses (MOMLV) are expressed in the packaging systems used in preference for pseudotyping according to the invention (gag: region coding for SEQ ID NO: 12, pol: SEQ ID NO: 11, Nukleotide 1970–5573; cf. Appendix to the sequence listing, re SEQ ID NO: 11). According to the invention, however, other gag and pol variants of MLV are also included as long as they exhibit the above-mentioned advantages for vector production. In particular, the above-mentioned gene derivatives are included according to the invention.

It was ascertained within the scope of the present invention that LCMV-GP also pseudotypes lentiviral nucleocapsids (see examples). According to a particular embodiment, the packaging systems may also therefore contain the gag and pol gene products of lentiviruses, i.e. lentiviral packaging systems (packaging cell lines) may be used. It is immaterial from which lentivirus the packaging system is derived. Suitable lentiviral packaging cells within the scope of the present invention include, for example, cell lines derived from human immunodeficiency virus (HIV), simian immunodeficiency virus (SIV) or feline immunodeficiency virus (FIV). In this connection, it could be necessary for an efficient production of infectious lentivirus vectors to express, in addition, accessory lentiviral genes such as rev (region coding for SEQ ID NO: 21; cf. Appendix to the sequence listing, re SEQ ID NO: 15) or tat (region coding for SEQ ID NO: 20; cf. Appendix to the sequence listing, re SEQ ID NO: 15) in the case of HIV vectors. Within the scope of the present invention, LCMV proteins may be used for pseudotyping in all the lentiviral packaging systems.

The present invention also provides a (viral) packaging cell or a pseudotyped virion in which the virus is selected from the family of retroviridiae, particularly the MLV-related viruses and the lentiviruses. According to a particular embodiment of the invention, the retroviral packaging cell is selected from the group comprising packaging cells derived from MLV, HIV, SIV and FIV.

According to the invention, moreover, a pseudotyped virion is provided which can be obtained by pseudotyping a retroviral cell of MLV which does not express an ENV protein, the defective mutant L(ARM) of LCMV being used for pseudotyping. Alternatively, other variants of LCMV may also be used.

The present invention also provides a process for the production of the packaging cells/packaging cell lines according to the invention, wherein a retroviral packaging cell line transfected with one or more foreign genes is infected with LCMV according to known methods (cf. e.g. Maniatis, Sambrook, Fritsch: Molecular cloning, a laboratory manual; Cold Spring Harbor Laboratory Press, 1982). The virions which contain LCMV glycoprotein incorporated in their coat are expressed by the packaging lines. According to a particular embodiment of the invention, the pseudotype-producing packaging cells may be produced by transfecting a retroviral packaging cell line transfected with one or more foreign genes with an expression plasmid which contains the gp gene of LCMV or a part thereof and optionally, in addition, one or more genes from the group comprising np, 1 and z of LCMV.

The present invention also relates, therefore, to a process for the production of retroviral pseudotype vectors wherein retroviral packaging cells containing at least the gp gene of LCMV or a part thereof (see above) are produced initially and these are then cultivated under conditions that are suitable for the production of virions.

Within the scope of the present invention, the retroviral packaging cell line used is preferably an MLV packaging cell line which does not express a functional ENV protein and the LCMV used for pseudotyping is the deleted mutant L(ARM). The cell line described by von Laer et al. (J. Virol. 72 (1998) 1424–1430) may also be used as the ENV-negative packaging cell line.

The virions or packaging cells lines according to the invention may be used advantageously for producing viral pseudotype vectors which may be used advantageously for the transduction of cell lines but also of primary eukaryotic cells for research purposes (in vitro) or within the context of gene therapy.

The use of virions/packaging cells for gene therapy also comes into consideration, however, within the scope of the present invention. In this connection, gene therapy may include the treatment of infectious diseases such as AIDS and neoplasms such as breast cancer or melanoma and other diseases accessible by gene therapy. The transduction of haematopoietic stem cells also comes into consideration within the scope of the present invention.

The recombinant virion or the recombinant packaging cell (cell line) of the present invention comprises one or more transgenes. Preferably, said transgenes are selected from the group comprising marker genes such as, e.g. neo, lacZ or enhanced green fluorescent protein (EGFP) and/or genes which may be used therapeutically, such as, e.g. the suicide gene herpes simplex virus thymidine kinase (HSV-tk), cytosine deaminase (CD) and sequences with an antiviral effect such as ribozymes, antisense sequences and transdominant-negative genes and genes that may be used in tumour therapy such as mdr-1 for the protection of haemato-poietic cells in chemotherapy, and cytokine genes. Moreover, all transgenes which could be of interest within the context of a targeted gene transfer and the expression of the transgene(s) in cells in vitro or within the context of gene therapy may, however, be used.

The invention also includes a process for the preparation of a pharmaceutical preparation for gene therapy wherein viral pseudotype vectors or retroviral packaging cells according to the invention are formulated optionally with pharmaceutically compatible excipients and/or carriers. The present invention also provides a pharmaceutical preparation for gene therapy which comprises retroviral packaging cells according to the invention and optionally pharmaceutically compatible excipients and/or carriers.

The present invention provides for the first time vector systems which may be produced in high titres and concentrated. The vector particles according to the invention may also be purified without or without any substantial loss of infectiousness. The cell lines according to the invention are also characterised by a broad, trans-species host cell spectrum (cell tropism). Surprisingly, it has become apparent within the scope of the present invention that the pseudotyping according to the invention is not cytotoxic for the packaging cells. Stable packaging cell lines (packaging systems) are thus provided for the first time which permit stable retroviral transfer of transgenes into the target cells, i.e. which lead to a stable integration of the transgene in the genome of the target or host cells followed by stable expression of this gene.

The present invention will be explained below on the basis of examples, figures and a sequence listing.

EXAMPLES

Materials and Methods

Cells and Viruses

The env-negative packaging cell line TELCeB was provided by F.-L. Cosset (F. L. Cosset et al. J. Virol. 69 (1995) 7430–7436). The env-negative cell line 293gp2 has already been described (D. Von Laer et al., J. Virol. 72 (1997) 1424–1430). The mouse fibroblast cell line Sc-1 was cultivated in Minimal Essential Medium (Sigma, Deisenhofen, Germany) which had been enriched with 10% foetal calf serum (FCS, PAN Systems, Aidenbach, Germany). The human kidney cell line 293, the human hepatoma line HUH-7, the human fibroblast cell line Te671 and TELCeB and the mouse fibroblast cell line L-929 were cultivated in Dulbecco's Minimal Essential Medium (DMEM, Gibco, Paisley, Great Britain) which had been enriched with 10% FCS. The human haematopoietic precursor cell line TF-1 was kept in Iscove's Modified Dulbecco's Medium (Gibco, Paisley, Great Britain) which had been enriched with 10% FCS and IL-3. Conditioned medium of NIH3T3 cells which had been transfected with a BPV vector carrying the IL-3 gene were used as the source of IL-3 in concentrations that are required for maximum growth of TF-1 (H. Karasuyama et al., Eur. J. Immunol 18 (1988) 97–104). The human precursor cell line K562 was kept in RPMI (Gibco) which had been enriched with 10% FCS.

LCMV was deposited on 10.11.1998 at the European Collection of Cell Cultures (ECACC), Salisbury, Wiltshire SP4 OJG, Great Britain under the access number V98111005 according to the Budapest Treaty.

The MESV-type retroviral vector which carries the neomycin phosphotransferase gene (MP1N) has already been described (H.-G. Eckert, Blood 88 (1996) 3407–3415). The amphotrophic helper was a recombinant Moloney MLV capable of replication in which parts of the pol and the majority of the env gene had been replaced with that of the MLV strain 4070A [Mo-Ampho-MP, R320 (C. Münk, Proc. Natl. Acad. Sci. USA 94 (1997) 5837–5842)] as a SalI to ClaI fragment. The virus was propagated in Sc-1. The plaque-purified WE strain of the LCM virus was propagated in L-929 cells (T. M. Rivers, Virology 26 (1965) 270–282).

Continuous Flow Cytometric Analysis of LCMV-GP Expression

In order to analyse the expression of the LCMV glycoprotein, $3 \times 10^5$ to $10^6$ cells were harvested, pelleted and resuspended in 50 µl of a 1:40 dilution of mouse ascites which contained a murine monoclonal antibody against LCMV GP-1 (M. Bruns et al., Virology 130 (1983) 247–251). After 20 minutes' incubation on ice, the cells were washed three times with phosphate-buffered saline (PBS) and then incubated for a further 20 minutes in a 1:80 dilution of an FITC labelled goat anti-mouse antibody (Dako, Glostrup, Denmark). After three final wash stages in PBS, the cells were analysed using an FACScalibur device (Becton Dickinson, Heidelberg).

Titration of the Viruses

In order to determine the vector titre, $5 \times 10^4$ Sc-1 cells were inoculated with a five-fold dilution of the supernatants in 24-well tissue culture plates. For the retroviral neovector the selection was initiated after 24 hours with 400 µg G418 per ml (dry weight GIBCO). The medium was replaced every four days. The colonies were evaluated after ten days. The titre was expressed as G418 resistance transfer units per ml (GTU/ml). For the retroviral MFGnlsLacZ vector, X-gal (5-bromo-4-chloro-3-indolyl-β-D-galactopyranoside) staining was carried out two days after inoculation as described earlier (G. R. McGregor, Methods Mol. Biol. 7 (1989) 1–19). The titre was expressed in LacZ transfer units (LTU) per ml. Plaque-forming units of LCMV were assayed on L-929 cells as described previously (F. Lehmann-Grube, J. Gen. Virol. 37 (1977) 85–92).

MLV (LCMV) pseudotypes were neutralised by preincubation of an equal volume of a virus-positive supernatant with an anti-LCMV gp44-neutralising monoclonal antibody which was diluted 1:100 (M. Bruns et al., Virology 130 (1983) 247–251). The titres were then determined in LTU per ml as described.

DNA Analysis

The production of DNA and Southern blot analysis were carried out as described earlier (C. Stocking et al., Cell 53 (1988) 869–879). The genomic DNA was digested with HINDIII which makes a single cut at the 3' end of the neo gene in the MPLN vector. A fragment which contains the complete neo gene was used as a probe.

Production and Purification of the Virus

The virions were purified by gradient ultracentrifugation as described in detail earlier (L. Martinez-Peralta et al., J. Gen. Virol. 55 (1981) 475–479). In short, infectious cell culture supernatants were purified by centrifugation at low and high speeds. The virus was pelleted by ultracentrifugation and then purified in a 0–40% Urografin gradient (Schering AG, Berlin, Germany).

Example 1

Infection of TeLCeb with LCMV-LacZ Gene Transfer to Target Cells with Neutralisation of the Vector by Anti-GP Mab and Concentration of the Vector in the Gradient Rescue of an envelope protein-negative murine leukaemia virus vector with lymphocytic choriomeningitis virus: In order to find out whether LCMV is able to rescue (mobilise, complete) an envelope protein-negative retroviral vector, the env-negative packaging cell line TELCeB was infected with the LCMV WE strain in an m.o.i. of 0.01 (m.o.i.: multiplicity of infection; denotes the number of virus particles with which a cell is infected). TELCeB stem from the human fibroblast cell line Te671 and contain gag and pol genes as well as the retroviral vector MFGnlsLacZ (G. M. Crooks et al., Blood 82 (1993) 3290–3297). After infection with LCMV, the titre of LacZ transferring units (LTU) and of LCMV wild-type virus was measured by X-gal staining of the mouse fibroblast target cells (Sc-1) and by a plaque test (in plaque-forming units, PFU). In addition, the expression of LCMV glycoproteins in the infected TELCeB was measured by continuous flow cytometric analysis. The results are shown in FIG. 6. LTU were prepared for six days with a maximum of $5\times10^4$ LTU per ml on day 3. The highest titre for LCMV wild-type virus was $3\times10^8$ on day 2. The production of PFU had already decreased on day 3 when the maximum production of LTU together with the highest expression of LCMV glycoprotein was to be seen. The reason for this discrepancy could lie in the production of defective interfering LCMV particles which inhibit the replication of LCMV wild-type, but in all probability not the release of infectious retroviral vector particles. No obvious cytopathic effect was to be observed during the replication of LCMV in the packaging cell lines, although high levels of LCMV glycoproteins were expressed (data not shown).

A test was then carried out to find out whether the infectious virus which was produced by the LCMV-infected TELCeB mediated the LacZ gene transfer specifically by way of LCMV glycoproteins. The supernatants were incubated for one hour with a neutralising anti-LCMV gp44 monoclonal antibody. This led to a more than threefold log reduction of the LTU titre. The amphotrophic pseudotype of the same retroviral vector was not neutralised by the anti-LCMV antibody (Tab. 1). These data show that the MLV/LCMV chimeric virions actually carried LCMV glycoproteins on their surface which are able to mediate gene transfer in the absence of retroviral envelope proteins by means of the LCMV receptor.

TABLE 1

Infectious retroviral vector particles which are produced by LCMV-infected packaging cell lines can be neutralised by anti-LCMV glycoprotein monoclonal antibodies (mab).

| Virus | anti-LCMV mab | Titre (LTU/ml) |
|---|---|---|
| Amphotrophic helper | no | $2 \cdot 10^5$. |
| Amphotrophic helper | yes | $2 \cdot 10^5$ |
| LCMV | no | $7 \cdot 10^4$ |
| LCMV | yes | $3 \cdot 10^1$ |

MLV (LCMV) pseudotypes retain infectiousness during concentration by gradient ultracentrifugation: amphotrophic retroviruses lose infectiousness after centrifugation, in all probability due to the lability of the retroviral envelope glycoproteins (V. Moenning et al., Virology 61 (1974) 100–111). A test was carried out to find out whether the MLV(LCMV) pseudotypes are more stable. TELCeB were infected with LCMV or with amphotrophic helper virus. Titres of the viral vector in the direct supernatant were $5\times10^4$ LTU per ml for both pseudotypes. Viruses were pelleted from 60 ml supernatant and purified by centrifugation through a 0–40% Urografin gradient. The pseudotype titres (in LTU per ml) are shown in FIG. 7. The total expected yield of $3\times10^6$ LTU for the LCMV pseudotype was obtained in full, in contrast to $1\times10^3$ LTU for the amphotrophic virus. The reverse transcriptase activity in the bands showed that the amount of virus particles which was obtained from the gradient was similar for both pseudotypes (data not shown). Compared with the amphotrophic virions, the infectiousness of MLV(LCMV) pseudotypes during ultracentrifugation was, however, more stable at least by a factor of 1000.

LCMV pseudotypes were also stable during storage at 4° C. Within the period of observation of three days, the loss of titre was twice as low (compared with the starting titre of MLV (LCMV)). A deep freeze cycle (−80° C.) and thawing led to a loss of pseudotype titre, which was twice as low.

Example 2
Gag and Pol Gene Products are Required for Packaging Retroviral RNA into the LCMV Qlycoprotein Pseudotypes A test was carried out to find out whether the retroviral RNA alone could be packaged into the LCMV or whether gag and pol gene products were required. 293 cells and 293gp2 cells, the latter containing gag and pol of MLV, were transfected with a retroviral vector based on MLV which contained the neo gene (MPlN), and cell lines which contained the stably integrated vector were prepared by G418 selection (293MP1N and 293gp2MP1N; a clone of the cell line 293gp2MP1N denoted SF23 was deposited at the Deutsche Sammlung von Mikroorganismen und Zellkulturen (German Collection of Microorganisms and Cell Cultures; DSMZ), Mascheroder Weg 1b, 38124 Braunschweig, Germany under the access number DSM ACC2374 according to the Budapest Treaty). These cells (mass cultures) were then infected either with an amphotrophic helper capable of replication or with the LCMV wild-type virus. The results are shown in Tab. 2. Infectious vector which transferred neomycin resistance was obtained from both cell lines after infection with the amphotrophic helper. After infection with LCMV, however, only 293gpMP1N produced infectious retroviral particles whereas 293MP1N, which expressed no retroviral Gag or Pol, did not. Retroviral genomic RNA was not, therefore, packaged into infectious virions by LCMV in the absence of gag and pol gene products.

TABLE 2 gag and/or pol gene products are essential for the rescue of a retroviral vector by LCMV

| | Vector titre* released after infection with | | |
|---|---|---|---|
| Cell line | LCMV | amphotrophic helper | (control) |
| 293MP1N | 0 | $1 \cdot 10^4$ | 0 |
| 293gp2MP1N | $2 \cdot 10^3$ | $6 \cdot 10^4$ | 0 |

*Vector titres are expressed in G418-resistant cell colonies which were obtained after inoculation of Sc-1 with the viral supernatants (G418 transfer units/ml).

Example 3
Infection of 293qpMP1N with LCMV and Stable Gene Transfer to L929—detection by Southern Blotting MLV (LCMV) pseudotypes mediate transfer and stable integration of the retroviral vector genome: the transfer of G418 resistance by the retroviral LCMV pseudotype showed that the marker gene had been stably integrated into the host genome. In order to verify that MLV (LCMV) pseudotypes are able to mediate stable transduction with integration of the transgene into the target cell genome, a retroviral vector which contained the neomycin resistance gene (neo) was rescued by LCMV infection of the env-negative packaging cell line 293gp2MP1N. The titres were measured by transfer of G418 resistance to Sc-1 cells and lay between $1 \times 10^3$ and $1 \times 10^4$ G418 transfer units (GTU) per ml. Resistant cell clones appeared after eight days' selection and were cultivated for a further three weeks. The DNA of 12 G418-resistant clones underwent a Southern blot analysis after restriction with HindIII, a single-cut enzyme, using a Neo probe. One copy of the integrated retroviral vector genome per cell was detected in 10 clones, and two copies in the other two clones (data not shown). Transduction with the MLV(LCMV) pseudotype therefore led to stable integration of the transgene.

Example 4

Expression of LCMV Glycoprotein (LCMV-GP) in TeLCeB-L(Arm)

Material and Methods

The preparation of the env-negative packaging line TeLCeb, which contains gag and pol of MLV as well as a retroviral vector genome with LacZ as the transgene, has already been described in detail (F. L. Cosset et al., J. Virol. 69 (1995) 7430–7436). The titration of the vector supernatants was carried out on 293-cells by X-Gal staining as has already been described (G. R. McGregor, Methods Mol. Biol. 7 (1989) 1–19). The cells were cultivated in DMEM with 10% FCS. The L(Arm) strain of LCMV is produced after several passages of LCMV in L929 cells (M. Bruns et al., Virology 177 (1990) 615–624). LCMV nucleoprotein (LCMV-NP) of L(Arm) was detected by immunofluorescence staining of the cells on slides with a polyclonal anti-LCMV rabbit serum. This standard method has already been described in detail (M. Bruns et al., Virology 177 (1990) 615–624). For the expression of LCMV-GP, the gp gene was cloned into the episomal EBV vector pCep4 (Invitrogen) which carries a hygromycin resistance gene.

Results

In the experiments for pseudotyping by the sole expression of LCMV-GP in env-negative retroviral packaging lines, a higher GP-mRNA expression was obtained with the expression plasmids than with LCM wild virus infection (FIG. 4). This result shows that the simultaneous presence of at least one further LCMV gene product in addition to the LCMV glycoprotein brings about an increase in glycoprotein production and promotes the formation of pseudotypes. In order to substantiate this conclusion directly, the ectopically expressed (from a plasmid) LCMV-GP was complemented with the LCMV proteins of the L(ARM) strain of LCMV. This defective strain lacks the functional glycoprotein and it therefore forms no plaques, is not pathogenic for mice and proliferates within a cell culture only over several weeks (whereas LCM wild virus does so within 24 hours). All the other gene products of L(ARM) (NP, L and Z) exhibit no detectable defects.

TeLCeb were infected with L(Arm)-containing cell culture supernatant and passages were then run for 5 weeks. Experience has shown that this is the time that the defective virus requires to infect all the cells of a culture. The complete infection of all the cells was verified by immunofluorescence staining with an anti-LCMV serum. TeLCeb-L(Arm) were transfected with pCep-GP by electroporation (electroporator from Dr. Fischer, Heidelberg) and selected for 2 weeks with hygromycin. As a control, cells were transfected with pCep4 (without GP gene). In TeLCeb-L(Arm) which were transfected with pCep-GP, pseudotypes which transferred lacZ to 293-cells were produced after selection. The titre lay between $10^2$ and $10^3$/ml. This result shows clearly that the LCMV-GP in the expression plasmid described was functional and is able to pseudotype retroviral vectors.

Example 5

Pseudotyping of an HIV Vector which Expresses the Green Fluorescent Protein (GFP)

Material and Methods

Figure 5:
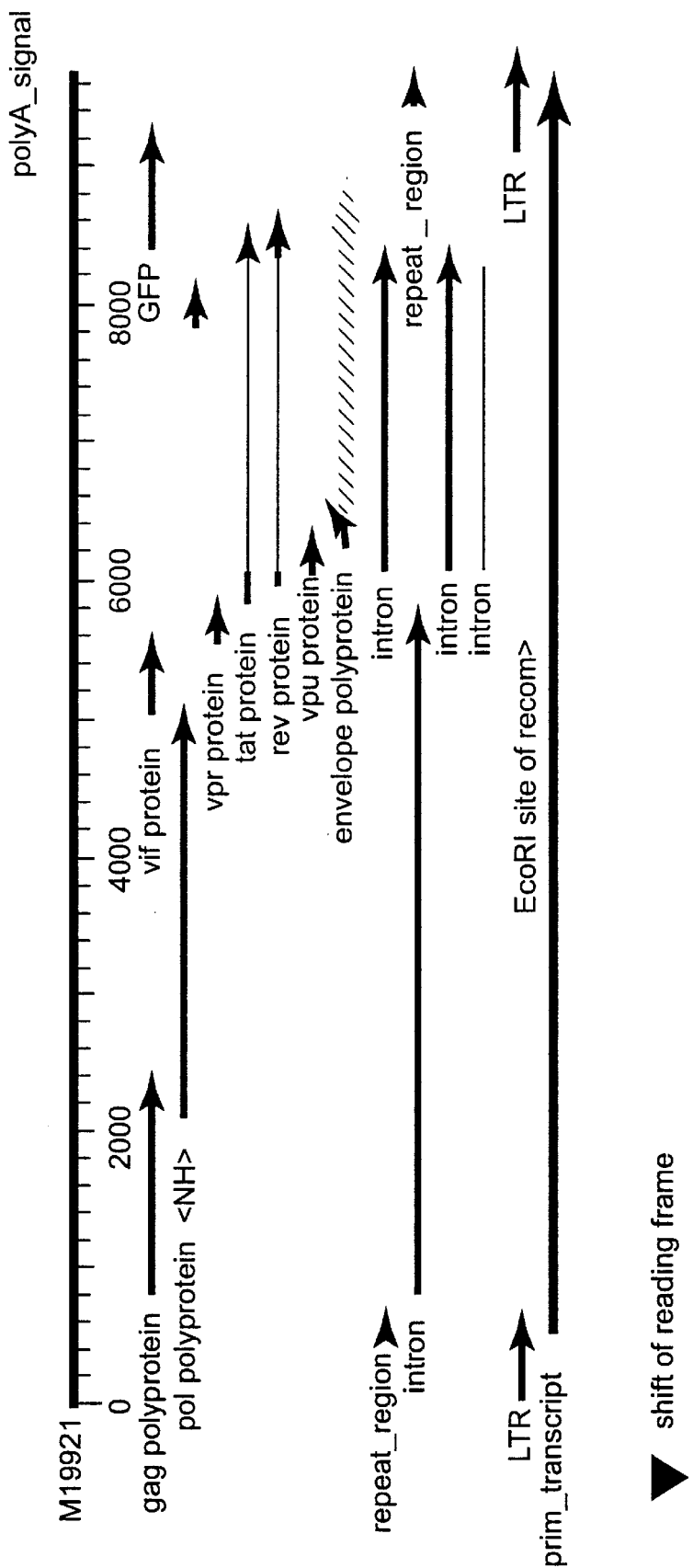
Figure 6:
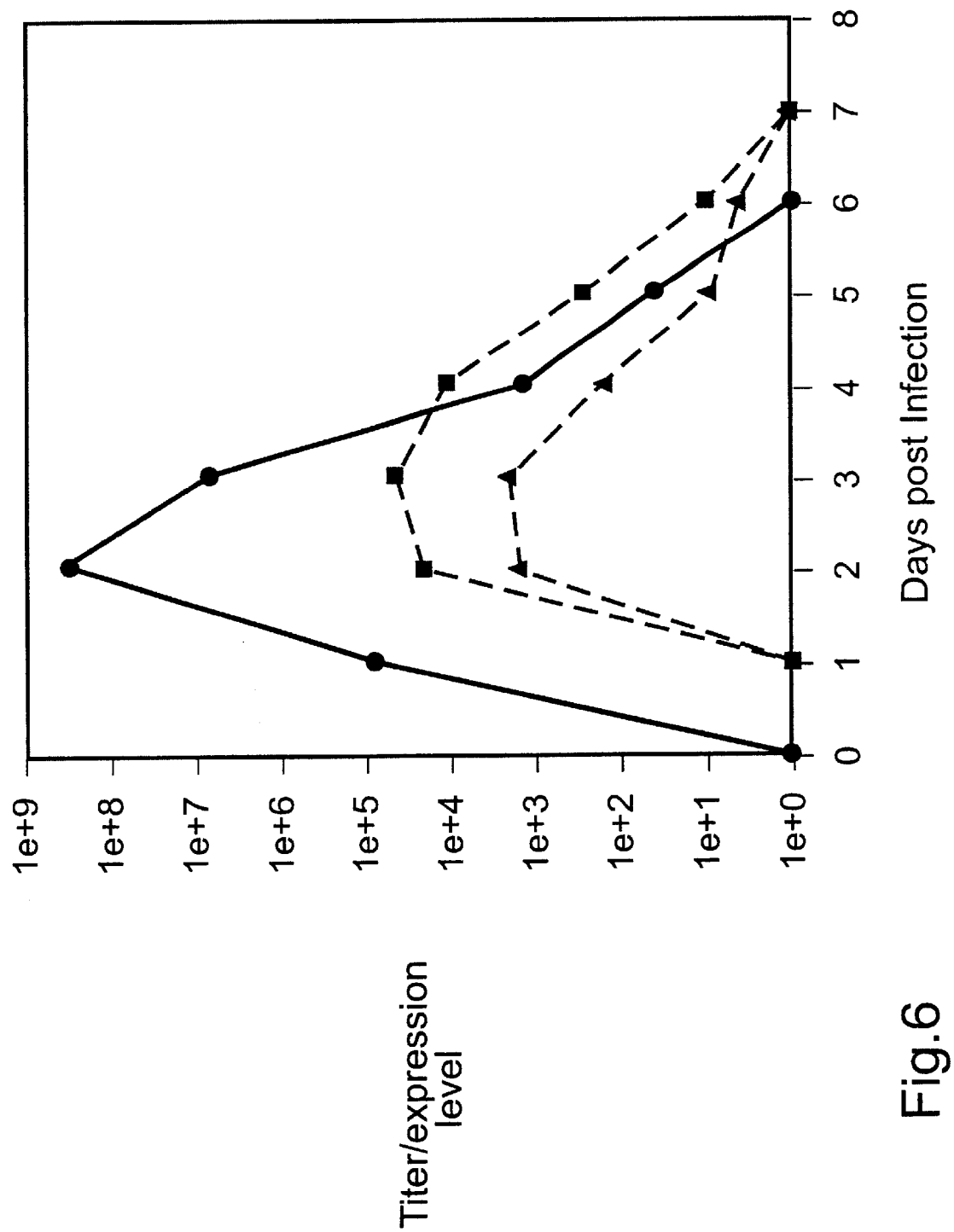
Figure 7:
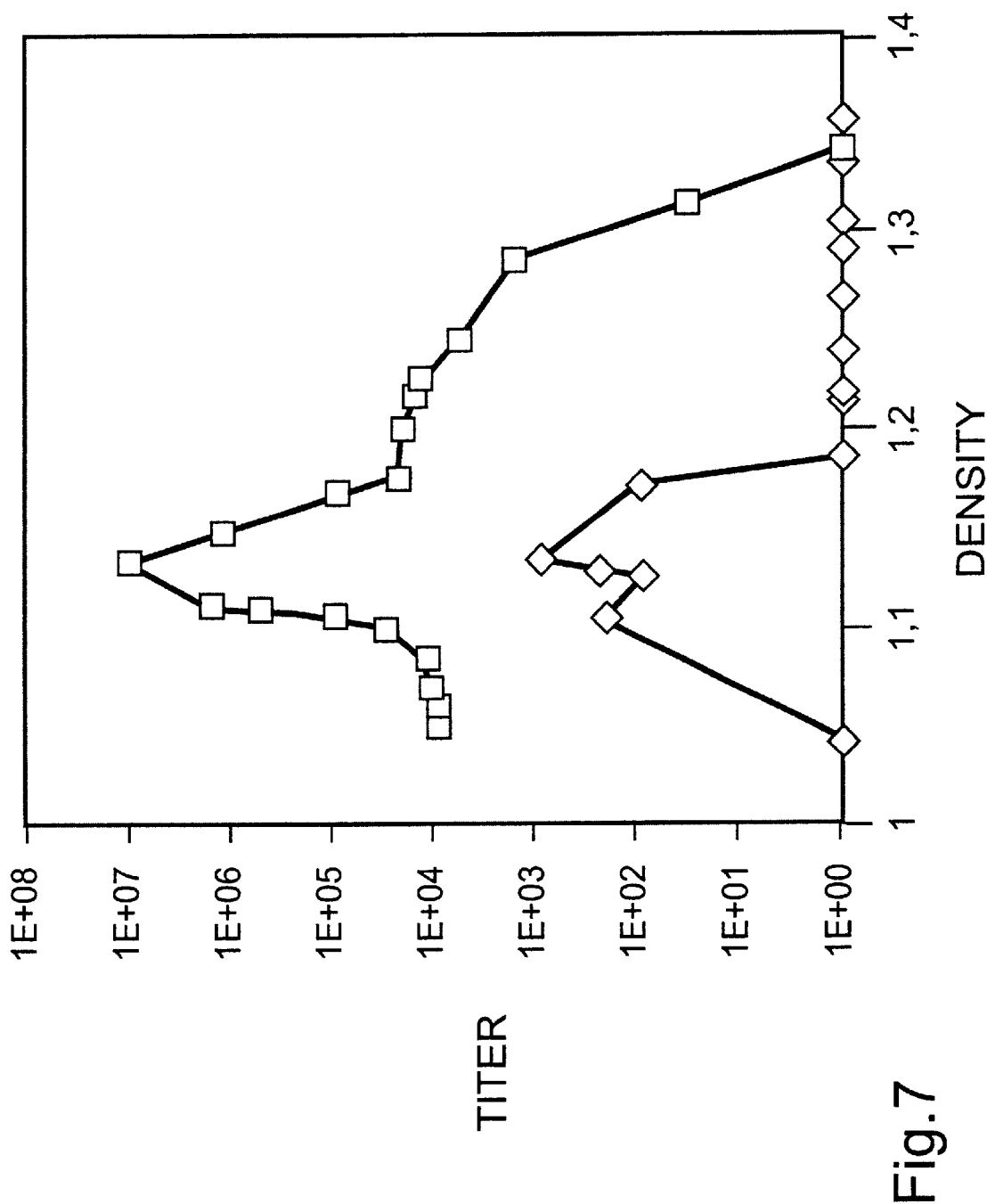

The lentiviral vector HIV-GFP is derived from the infectious DNA clone pNL4–3 of HIV and has already been described in detail (FIG. 5) (R. I. Connor et al., Virology 206 (1995) 935–944). At the beginning of env, the NdeI cleavage site was filled in and religated as a result of which the reading frame shifts and no functional envelope protein is synthesised. Further, instead of nev, the gene for the green fluorescent protein (GFP) was cloned. The titre of the LCMV-WE strain used was determined by a plaque assay on L929 which has already been described in detail (F. Lehmann-Grube et al., J. Gen. Virol. 37 (1977) 85–92). The calcium phosphate transfections were carried out on 293 with a standard protocol (Maniatis, et al., Molecular cloning, a laboratory manual; Cold Spring Harbor Laboratory Press, 1982).

Results 293-cells were infected with an m.o.i. of 0.1 of the LCMV-WE strain. After one hour transfection was carried out with HIV-GFP and after two days the supernatants were harvested and transferred to 293-cells. The titre was determined by the GFP expression in the 293-target cells by means of immunofluorescence and lay between $10^2$ and $10^3$ per ml. After transfection with HIV-GFP alone (without prior infection with LCMV), no production of infectious vector particles occurred, as expected.

Example 6

Investigation of Cell Tropism

MLV(LCMV) pseudotypes infect various human cell lines: the tropism of MLV(LCMV) pseudotypes was analysed. Several human cell lines derived from cells which are attractive targets for gene therapy such as haematopoietic progenitor cells and hepatocytes were analysed. The transfer efficiency relative to mouse fibroblasts is shown in Tab. 3. All the cell lines analysed were susceptible to MLV(LCMV) pseudotypes. Even hamster cells which are normally resistant to transduction with MLV-derived vectors could be transduced efficiently with the MLV(LCMV) pseudotypes.

TABLE 3

Host spectrum of MLV (LCMV) pseudotypes

| Cell line | Origin | Transduction efficiency |
|---|---|---|
| 293 | epithelium, human | +++ |
| K-562 | myeloid progenitor cells, human | +++ |
| TF-1 | myeloid progenitor cells, human | + |
| HUH-1 | hepatoma, human | ++ |
| Jurkat | lymphocyte, human | ++* |
| Sc-1 | fibroblast, mouse | +++ |
| CHO | epithelium, hamster | +++ |
| Cf2Th | thymus stroma, dog | +++ |

*The pseudotypes were prepared using LCMV passaged on (adapted to) lymphocytes. Pseudotypes of LCMV passaged on fibroblasts do not transduce lymphocytes.

BRIEF DESCRIPTION OF FIGURES

FIG. 1: Retroviral packaging lines The retroviral genes gag, pol and env are stably integrated into the genome of the retroviral packaging lines. Env is usually expressed separately from gag and pol. Moreover, the vector genome is expressed with the transgene and regulatory cis elements (1). The genomic RNA of the vector contains a packaging signal which was deleted on the gag, pol and env genes. In the cytoplasm, the retroviral proteins therefore package the vector genome selectively (2). A complete retroviral nucleocapsid forms (3) and is released by budding on the cell membrane (4). In so doing, retroviral envelope protein or, in the case of the pseudotypes, a foreign viral envelope protein is carried along. Outside the cell, the virus matures by proteolytic cleavage of the retroviral precursor proteins in the nucleocapsid.

FIG. 2: The genomic RNA of the LCM virus. The genome of LCMV is composed of 2 ambisense RNA molecules each with two open reading frames. The 4 genes and their orientation are given.

FIG. 3: The production of MLV(LCMV) pseudotypes. Packaging lines which produce no viral envelope proteins also release no infectious retroviral vectors. If such an env-negative packaging line is infected with LCM virus, the retroviruses can insert the LCMV glycoprotein into their coat. So-called pseudotypes are produced. Moreover, LCM wild virus is released during LCMV replication.

FIG. 4: Discrepancy between high mRNA and low protein concentration in the case of ectopic GP-C expression. 293-cells were transfected with different expression constructs for LCMV glycoprotein (Ef-1 alpha promoter, alphavirus vector from Invitrogen, CMV promoter+beta globin intron, see above: preferred expression cassettes). After 2 days, the gp-mRNA concentration in the Northern blot and the GP-1/GP-2 protein quantities on the cells were measured in parallel by continuous flow cytometry. 293-cells that were infected with LCMV wild-type were used as a control. In the case of wild virus infection, the GP-1/GP-2 protein expression was 2–3 log stages above the negative control, with a relatively weak mRNA band in the Northern blot (upper band LCMV-genomic RNA, lower band gp-mRNA). In the case of ectopic expression, the protein concentration for GP-1/GP-2 was only at most one log stage above the negative control despite a higher mRNA concentration than with wild virus infection.

FIG. 5: HIV-GFP. The infectious DNA clone of HIV pNL4-3 was cut at the beginning of the env gene with NdeI, the cleavage site was filled in and religated (s). As a result, the reading frame shifts and no functional env gene product is produced. Instead of nef, the gene for the "green fluorescent protein" (GFP) was cloned between XhoI and BamHI.

FIG. 6: Rescue of the retroviral vector MFGInsLacZ by LCMV.

The retroviral env-negative packaging cell line TELCeB was infected by LCMV with an m.o.i. of 0.01. Between day 1 and 7 after infection, the supernatants were replaced daily and the titres of the LCMV wild-type and LacZ vector were determined by a plaque assay on L-929 and by LacZ gene transfer to Sc-1. In addition, a part of the LCMV-infected TELCeB cells were stained daily with a monoclonal antibody directed against the LCMV glycoprotein GP-1 and analysed by continuous flow cytometry. The mean fluorescence is shown. O—O LCMV wild-type titre; □—□LacZ transfer units; Δ—Δ mean fluorescence of the LCMV glycoprotein GP expression.

FIG. 7: MLV(LCMV) pseudotypes retain their infectiousness after ultracentrifugation. TELCeB were infected with LCMV or amphotrophic helper virus. The supernatants were harvested and frozen. The MLV(LCMV) and amphotrophic

What is claimed is:

1. A retroviral packaging cell, which contains gag and pol genes of a retroviral vector and a nucleic acid sequence coding for the glycoproteins GP-1 and GP-2 of lymphocytic choriomeningitis virus (LCMV), wherein the gag and pol genes and said glycoproteins are expressed in said retroviral packaging cell.

2. The retroviral packaging cell according to claim 1, which also contains at least one gene from the group consisting of an env gene of a retroviral vector, regulatory retroviral genes, the gene np of LCMV coding for the nucleoprotein, the gene I of LCMV coding for RNA polymerase and the gene z of LCMV coding for a protein with an unknown function.

3. The retroviral packaging cell according to claim 1, wherein the retroviral vector is a MLV-related retroviral vector or a lentiviral vector.

4. The retroviral packaging cell according to claim 1, wherein the retroviral vector is derived from MLV, HIV, SIV or FIV.

5. The retroviral packaging cell according to claim 1 further comprising a recombinant retroviral vector containing one or more transgenes selected from the group consisting of marker genes and genes encoding therapeutic proteins, wherein the retroviral packaging cell produces recombinant retroviral virions.

6. The retroviral packaging cell according to claim 5, wherein the marker genes are neo, lacZ or EGFP.

7. The retroviral packaging cell according to claim 1, further comprising a recombinant retroviral vector containing a ribozyme, an antisense sequence or a transdominant-negative acting gene, wherein the retroviral packaging cell produces recombinant retroviral virions.

8. The retroviral packaging cell according to claim 1 which is infected with lymphocytic choriomeningitis virus (LCMV), wherein said retroviral packaging cell further comprises one or more foreign genes.

9. The retroviral packaging cell according to claim 8, wherein the retroviral vector is derived from a MLV which does not express an Env protein, and wherein LCMV is the defective mutant L(ARM).

10. The retroviral packaging cell according to claim 1, which is obtained by a transfection of a packaging cell with an expression plasmid which comprises the nucleic acid sequence coding for glycoproteins GP-1 and GP-2 of LCMV.

11. The retroviral packaging cell according to claim 1, which is obtained by a transfection of a packaging cell with an expression plasmid which comprises the nucleic acid sequence coding for glycoproteins GP-1 and GP-2 of LCMV, and at least one of the np gene of LCMV, the/gene of LCMV or the z gene of LCMV.

12. The retroviral packaging cell, which expresses pseudotyped virions which contain LCMV glycoprotein inserted in the coat of said pseudotyped virions.

13. A process for the preparation of the retroviral packaging cell according to claim 5, comprising the step of contacting LCMV, under suitable conditions, with a retroviral packaging cell that comprises the genes gag and pol of a retroviral vector and a recombinant retroviral vector containing one or more transgenes selected from the group consisting of marker genes and genes encoding therapeutic proteins, whereby the infectious recombinant retroviral virions are pseudotyped with the LCMV glycoproteins expressed by said LCMV.

14. A process for the preparation of the retroviral packaging cell according to claim 5, comprising the step of introducing a plasmid vector expressing glycoproteins GP-1 and GP-2 of LCMV into a retroviral packaging cell that comprises the genes gag and pol of a retroviral vector and a recombinant retroviral vector containing one or more transgenes selected from the group consisting of marker genes and genes encoding therapeutic proteins, whereby the infectious recombinant retroviral particles are pseudotyped with the LCMV glycoproteins.

15. A process for the preparation of recombinant retroviral pseudotype virions, comprising the steps of performing the process according to claim 13 and cultivating the resulting retroviral packaging cells under conditions which are suitable for the production of recombinant retroviral pseudotype virions.

16. A process for the preparation of recombinant retroviral pseudotype virions, comprising the steps of performing the process according to claim 14 and cultivating the resulting retroviral packaging cells under conditions which are suitable for the production of recombinant retroviral pseudotype virions.

17. A method for in vitro infection of cells and for the expression of a transgene in said cells, said method comprising contacting the cells with the retroviral packaging cells according to claim 5 or with cell culture supernatants of said retroviral packaging cells, wherein the contacting is performed under conditions which allow infection of the cells, and wherein the infected cells are cultured under conditions which allow expression of the transgene.

18. The retroviral packaging cell according to claim 5, wherein said therapeutic proteins are selected from the group consisting of a herpes simplex virus thymidine kinase (HSV-tk), a cytosine deaminase (CD) and a cytokine.

19. The retroviral packaging cell according to claim 5, wherein said therapeutic proteins are mdr-1 proteins.

* * * * *